US010547004B2

(12) United States Patent
Mitchell et al.

(10) Patent No.: US 10,547,004 B2
(45) Date of Patent: *Jan. 28, 2020

(54) ORGANIC SEMICONDUCTORS

(71) Applicant: Merck Patent GmbH, Darmstadt (DE)

(72) Inventors: William Mitchell, Chandler's Ford (GB); Changsheng Wang, Durham (GB); Mansoor D'Lavari, Bude (GB); David Sparrowe, Bournemouth (GB)

(73) Assignee: MERCK PATENT GMBH, Darmstadt (DE)

( * ) Notice: Subject to any disclaimer, the term of this patent is extended or adjusted under 35 U.S.C. 154(b) by 93 days.

This patent is subject to a terminal disclaimer.

(21) Appl. No.: 14/433,478

(22) PCT Filed: Sep. 6, 2013

(86) PCT No.: PCT/EP2013/002679
§ 371 (c)(1),
(2) Date: Apr. 3, 2015

(87) PCT Pub. No.: WO2014/053206
PCT Pub. Date: Apr. 10, 2014

(65) Prior Publication Data
US 2015/0255725 A1    Sep. 10, 2015

(30) Foreign Application Priority Data

Oct. 5, 2012 (EP) ..................... 12006904

(51) Int. Cl.
| H01L 51/00 | (2006.01) |
| C08G 61/12 | (2006.01) |
| C07D 519/00 | (2006.01) |
| B82Y 10/00 | (2011.01) |
| C07D 495/22 | (2006.01) |
| C08G 75/06 | (2006.01) |
| H01B 1/12 | (2006.01) |
| H01L 51/05 | (2006.01) |
| H01L 51/42 | (2006.01) |
| C08L 65/00 | (2006.01) |

(52) U.S. Cl.
CPC .......... *H01L 51/0036* (2013.01); *B82Y 10/00* (2013.01); *C07D 495/22* (2013.01); *C07D 519/00* (2013.01); *C08G 61/126* (2013.01); *C08G 75/06* (2013.01); *H01B 1/128* (2013.01); *H01L 51/0035* (2013.01); *H01L 51/0043* (2013.01); *C08G 61/123* (2013.01); *C08G 61/125* (2013.01); *C08G 2261/1412* (2013.01); *C08G 2261/226* (2013.01); *C08G 2261/314* (2013.01); *C08G 2261/3222* (2013.01); *C08G 2261/3223* (2013.01); *C08G 2261/3243* (2013.01); *C08G 2261/3246* (2013.01); *C08G 2261/344* (2013.01); *C08G 2261/411* (2013.01); *C08G 2261/91* (2013.01); *C08G 2261/92* (2013.01); *C08G 2261/95* (2013.01); *C08L 65/00* (2013.01); *H01L 51/0047* (2013.01); *H01L 51/0541* (2013.01); *H01L 51/0558* (2013.01); *H01L 51/4246* (2013.01); *H01L 51/4253* (2013.01); *Y02E 10/549* (2013.01)

(58) Field of Classification Search
CPC .. H01L 51/0036; C08G 2261/91; C08G 75/10
See application file for complete search history.

(56) References Cited

U.S. PATENT DOCUMENTS

| 7,816,673 | B2 | 10/2010 | Park |
| 8,623,993 | B2 | 1/2014 | Hsu |
| 8,853,679 | B2 | 10/2014 | Zuberi et al. |
| 9,017,577 | B2 | 4/2015 | Tierney |
| 9,096,716 | B2 | 8/2015 | Hsu |
| 2011/0226999 | A1* | 9/2011 | Tierney ................. C08G 61/12 252/500 |
| 2012/0184089 | A1* | 7/2012 | Zuberi ................ C07D 495/04 438/478 |

(Continued)

FOREIGN PATENT DOCUMENTS

| CN | 101200471 A | 6/2008 |
| CN | 102124044 A | 7/2011 |
| CN | 102482291 A | 5/2012 |

(Continued)

OTHER PUBLICATIONS

Chen et al., "Donor-Acceptor Random copolymers Based on a Ladder-Type Nonacyclic Unit: Synthesis, Characterization, and Photovoltaic Applications," Macromolecules (2011)44(21):8415-842, Nov. 2011.*
International Search Report dated Oct. 31, 2013 issued in corresponding PCT/EP2013/002679 application (pp. 1-3).
Notification of the First Office Action dated Mar. 10, 2016 issued in corresponding CN 201380056621.5 application (pp. 1-2).
Y.X. Xu et al., "Improved Charge Transport and Absorption Coefficient in Indacenodithieno[3,2-b]thiophene-based Ladder-Type Polymer Leading to Highly Efficient Polymer Solar Cells", Advanced Materials, vol. 24 (2012) pp. 6356-6361.
English Abstract of CN 102124044 A published Jul. 13, 2011.

(Continued)

*Primary Examiner* — Gregory Listvoyb
(74) *Attorney, Agent, or Firm* — Millen White Zelano & Branigan

(57) ABSTRACT

The invention relates to novel organic semiconducting oligomers or polymers containing alkylated dithieno[2,3-d:2', 3'-d']-s-indaceno[1,2-b:5,6-b']dithiophene units, methods for their preparation and educts or intermediates used therein, polymers, blends, mixtures and formulations containing them, the use of the oligomers, polymers, blends, mixtures and formulations as semiconductor in organic electronic (OE) devices, especially in organic photovoltaic (OPV) devices or organic photodetectors (OPD), and to OE, OPV and OPD devices comprising these oligomers, polymers, blends, mixtures or formulations.

7 Claims, 1 Drawing Sheet

(56) References Cited

U.S. PATENT DOCUMENTS

2013/0237676 A1 9/2013 Hsu et al.
2014/0158949 A1* 6/2014 Wang .................. C07D 495/22
　　　　　　　　　　　　　　　　　　　　　　　252/511

FOREIGN PATENT DOCUMENTS

| CN | 103649096 A | 3/2014 |
| TW | 201012840 A | 4/2010 |
| TW | 201309779 A | 3/2013 |
| TW | 201336887 A | 9/2013 |
| WO | 2012017184 A1 | 2/2012 |
| WO | 2013/010614 A2 | 1/2013 |

OTHER PUBLICATIONS

English Abstract of CN 102482291 A published May 30, 2012.
English Abstract of CN 103649096 A published Mar. 19, 2014.
Search Report dated Mar. 13, 2017 issued in corresponding TW 102136108 application (pp. 1).
Summary of Search Report dated Jul. 3, 2018 issued in corresponding JP 2015-534918 application (pp. 1-2).

* cited by examiner

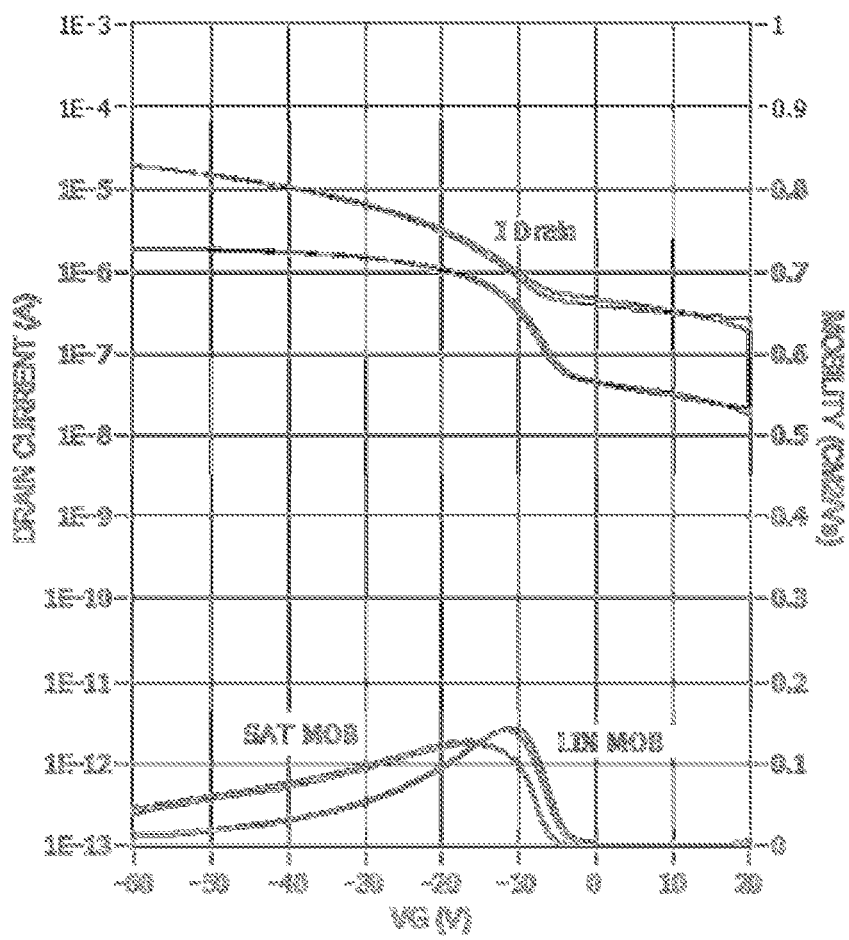

ORGANIC SEMICONDUCTORS

TECHNICAL FIELD

The invention relates to novel organic semiconducting oligomers and polymers containing alkylated dithieno[2,3-d:2',3'-d']-s-indaceno[1,2-b:5,6-b']dithiophene units, methods for their preparation and educts or intermediates used therein, blends, mixtures and formulations containing them, the use of the oligomers, polymers, blends, mixtures and formulations as semiconductors in organic electronic (OE) devices, especially in organic photovoltaic (OPV) devices or organic photodetectors (OPD), and to OE, OPV and OPD devices comprising these oligomers, polymers, blends, mixtures or formulations.

BACKGROUND

Organic semiconducting (OSC) materials are receiving growing interest mostly due to their rapid development in the recent years and the lucrative commercial prospects of organic electronics.

One particular area of importance is organic photovoltaics (OPV). Conjugated polymers have found use in OPVs as they allow devices to be manufactured by solution-processing techniques such as spin casting, dip coating or ink jet printing. Solution processing can be carried out cheaper and on a larger scale compared to the evaporative techniques used to make inorganic thin film devices. Currently, polymer based photovoltaic devices are achieving efficiencies above 8%.

In order to obtain ideal solution-processible OSC molecules two basic features are essential, firstly a rigid π-conjugated core or backbone, and secondly suitable functionality of the aromatic cores in the OSC backbone. The former extends π-π overlaps, defines the primary energy levels of the highest occupied and lowest unoccupied molecular orbitals (HOMO and LUMO), enables both charge injection and transport, and facilitates optical absorption. The latter further fine-tunes the energy levels and enables solubility and hence processability of the materials as well as π-π interactions of the molecular backbones in the solid state.

A high degree of planarity reduces the energetic disorder of OSC backbones and accordingly enhances charge carrier mobilities. In prior art most of the polymeric OSCs with high charge carries mobilities are generally composed of fused ring aromatic systems, and are semicrystalline in their solid states. Such polymers are for example indacenodithiophene-benzothiadiazole copolymers, for which it was reported by Zhang et al., *J. Am. Chem. Soc.*, 2010, 132(33), 11437 that a hole mobility of 1 $cm^2/V$ s was achieved.

Nevertheless, the structures of solubilising groups (e.g., the length, the regio-regularity, the spatial orientation of the alkyl chains etc.), have direct effects on the solubility and hence the processability of the OSC, on the planarity of the polymer backbone, on the inter-chain π-π interactions and on the HOMO-LUMO levels/bandgaps. For many applications, like e.g. OPV devices, optimisation of the electronic properties of the conjugated backbones by fine-tuning the solubilising functional groups can result in dramatic effects on the efficiencies.

Thus there is still a need for organic semiconducting (OSC) materials that are easy to synthesize, especially by methods suitable for mass production, show good structural organization and film-forming properties, exhibit good electronic properties, especially a high charge carrier mobility, good processability, especially a high solubility in organic solvents, and high stability in air. Especially for use in OPV cells, there is a need for OSC materials having a low bandgap, which enable improved light harvesting by the photoactive layer and can lead to higher cell efficiencies, compared to the polymers from prior art.

It was an aim of the present invention to provide new oligomers and polymers for use as organic semiconducting materials that do not have the drawbacks of prior art materials as described above, are easy to synthesize, especially by methods suitable for mass production, and do especially show good processability, high stability, good solubility in organic solvents, high charge carrier mobility, and a low bandgap. Another aim of the invention was to extend the pool of OSC materials available to the expert. Other aims of the present invention are immediately evident to the expert from the following detailed description.

The inventors of the present invention have found that one or more of the above aims can be achieved by providing oligomers and conjugated polymers, containing tetraalkylated dithieno[2,3-d:2',3'-d']-s-indaceno[1,2-b:5,6-b']dithiophene or derivatives thereof as represented by the following formula, wherein X is C, Si or Ge and R is alkyl:

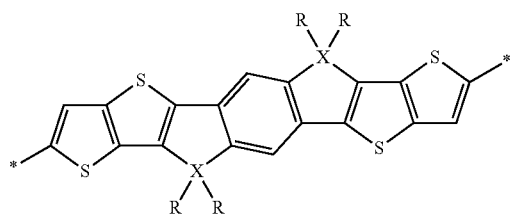

Strategically fusing additional aromatic rings along the long axis of the indacenodithiophene core unit creates numerous benefits in developing novel high performance OSC materials. Firstly, fusing additional aromatic rings increases the overall planarity and reduces the number of the potential twists of the conjugated molecular backbone. Elongation of a π-structure or monomer increases the extent of conjugation which facilitates charge transport along the polymer backbone. Secondly, increasing the proportion of sulphur atoms in the molecular backbone through fusing more thiophene rings promotes more intermolecular short contacts, which benefits charge hopping between molecules. Thirdly, the addition of fused-rings means increased proportion of ladder structure in the OSC polymer main chain, which improves the planarity of the molecular backbone. Additionally but not lastly, fusing aromatic rings can more efficiently modify the HOMO and LUMO energy levels and bandgaps of the target monomer structures compared with periphery substitutions.

By the incorporation of the electron-donating dithieno[2,3-d:2',3'-d']-s-indaceno[1,2-b:5,6-b']dithiophene unit and an electron-accepting unit into a co-polymer i.e. a "donor-acceptor" polymer, a reduction of the bandgap can be achieved, which enables improved light harvesting properties in bulk heterojunction (BHJ) photovoltaic devices. Also, by varying the substituents at the cyclopentane rings, the solubility and electronic properties of the polymers can be further optimised.

JP 2010-280623 A1 discloses compounds of the following formula

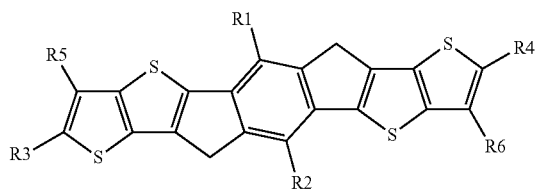

wherein R1-R6 are C1-C30 alkyl. However, these compounds represent a significantly different attempt to solublise the dithieno[2,3-d:2',3'-d']-s-indaceno[1,2-b:5,6-b']dithiophene core structure, by placing alkyl groups R1-R6 on the terminal thiophene and the central benzene rings.

GB 2472413 A and WO 2012/017184 A1 describe small molecule materials with a general formula as follows

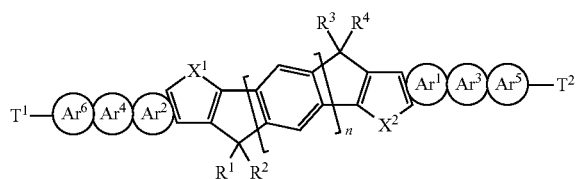

where $Ar^1$ to $Ar^6$ are independently fused heterocycles and $T^1$ and $T^2$ are terminal groups comprising both solublising chains and reactive functionalities.

Advanced Materials, 2012, in press, 'Improved Charge Transport and Absorption Coefficient in Indacenodithieno [3,2-b]thiophene-based Ladder-Type Polymer Leading to Highly Efficient Polymer Solar Cells' (Y.-X. Xu, C.-C. Chueh, H.-L. Yip, F.-Z. Ding, Y.-X. Li, C.-Z. Li, X. Li, W.-C. Chen, and A. K.-Y. Jen) discloses the following polymer:

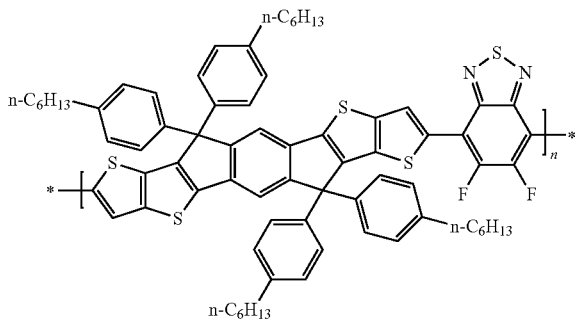

where the solubilising groups on the cyclopentadiarene rings contain 4-alkylphenyl groups.

However, there is no prior art disclosing oligomeric or polymeric materials containing dithieno[2,3-d:2',3'-d']-s-indaceno[1,2-b:5,6-b']dithiophene as claimed hereinafter.

SUMMARY

The invention relates to an oligomer or polymer comprising one or more divalent units of formula I

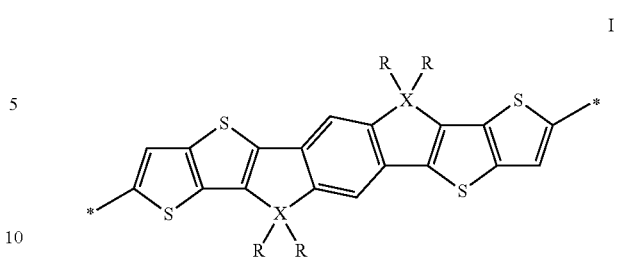

wherein R is on each occurrence identically or differently straight-chain or branched alkyl having 1 to 30 C atoms, and X is on each occurrence identically or differently C, Si or Ge.

The invention further relates to a formulation comprising one or more oligomers or polymers comprising units of formula I and one or more solvents, preferably selected from organic solvents.

The invention further relates to an organic semiconducting formulation comprising one or more oligomers or polymers comprising units of formula I, one or more organic binders, or precursors thereof, preferably having a permittivity $\in$ at 1,000 Hz and 20° C. of 3.3 or less, and optionally one or more solvents.

The invention further relates to the use of units of formula I as electron donor units in semiconducting polymers.

The invention further relates to a conjugated polymer comprising one or more repeating units, wherein said repeating units contain a unit of formula I and/or one or more groups selected from aryl and heteroaryl groups that are optionally substituted, and wherein at least one repeating unit in the polymer contains at least one unit of formula I.

The invention further relates to monomers containing a unit of formula I and further containing one or more reactive groups which can be reacted to form a conjugated polymer as described above and below.

The invention further relates to a semiconducting polymer comprising one or more units of formula I as electron donor units, and preferably further comprising one or more units having electron acceptor properties.

The invention further relates to the use of the oligomers and polymers according to the present invention as electron donor or p-type semiconductor.

The invention further relates to the use of the oligomers and polymers according to the present invention as electron donor component in semiconducting materials, formulations, blends, devices or components of devices.

The invention further relates to a semiconducting material, formulation, blend, device or component of a device comprising an oligomer or a polymer according to the present invention as electron donor component, and preferably further comprising one or more compounds or polymers having electron acceptor properties.

The invention further relates to a mixture or blend comprising one or more oligomers or polymers according to the present invention and one or more additional compounds which are preferably selected from compounds or polymers having one or more of semiconducting, charge transport, hole or electron transport, hole or electron blocking, electrically conducting, photoconducting or light emitting properties.

The invention further relates to a mixture or blend as described above and below, which comprises one or more oligomers or polymers of the present invention and one or more n-type organic semiconductor compounds or polymers, preferably selected from fullerenes or substituted fullerenes.

The invention further relates to a formulation comprising one or more oligomers or polymers, formulations, mixtures or blends according to the present invention and optionally one or more solvents, preferably selected from organic solvents.

The invention further relates to the use of oligomers, polymers, formulations, mixtures and blends of the present invention as charge transport, semiconducting, electrically conducting, photoconducting or light emitting material in optical, electrooptical, electronic, electroluminescent or photoluminescent components or devices.

The invention further relates to a charge transport, semiconducting, electrically conducting, photoconducting or light emitting material or component comprising one or more oligomers or polymers, formulations, mixtures or blends of the present invention.

The invention further relates to an optical, electrooptical or electronic component or device comprising one or more oligomers or polymers, formulations, mixtures, blends or components of the present invention.

The optical, electrooptical, electronic electroluminescent and photoluminescent components or devices include, without limitation, organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), solar cells, laser diodes, photoconductors, organic photodetectors (OPD), electrophotographic devices, electrophotographic recording devices, organic memory devices, sensor devices, charge injection layers, charge transport layers or interlayers in polymer light emitting diodes (PLEDs), organic plasmon-emitting diodes (OPEDs), Schottky diodes, planarising layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

BRIEF DESCRIPTION OF THE DRAWINGS

FIG. 1 is a transfer curve of a top gate OFET device of Example 2.

DETAILED DESCRIPTION

This invention relates to novel oligomers and homo- or co-polymers based upon dithieno[2,3-d:2',3'-d']-s-indaceno[1,2-b:5,6-b']dithiophene units solubilised with four alkyl groups. It also relates to the preparation of these semiconducting oligomers, homopolymers and copolymers through known transition metal catalysed polycondensation reactions.

The oligomers and polymers of the present invention are easy to synthesize and exhibit advantageous properties. The conjugated polymers of the present invention show good processability for the device manufacture process, high solubility in organic solvents, and are especially suitable for large scale production using solution processing methods. At the same time, the co-polymers derived from monomers of the present invention and electron accepting monomers show low bandgaps, high charge carrier mobilities, high external quantum efficiencies in BHJ solar cells, good morphology when used in p/n-type blends e.g. with fullerenes, high oxidative stability, and a long lifetime in electronic devices, and are promising materials for organic electronic OE devices, especially for OPV devices with high power conversion efficiency.

The unit of formula I is especially suitable as (electron) donor unit in p-type semiconducting oligomers, homopolymers and copolymers, in particular copolymers containing both donor and acceptor units, and for the preparation of blends of p-type and n-type semiconductors which are useful for application in bulk heterojunction photovoltaic devices.

In addition, the oligomers and polymers based upon dithieno[2,3-d:2',3'-d']-s-indaceno[1,2-b:5,6-b']dithiophene show the following advantageous properties:

i) The tetraalkylated dithieno[2,3-d:2',3'-d']-s-indaceno[1,2-b:5,6-b']dithiophene unit exhibit a co-planar structure similar to indenofluorene. Adopting a highly co-planar structure in the solid-state is beneficial for charge transport.

ii) The introduction of electron rich thieno[3,2-b]thiophene units into the tetraalkylated dithieno[2,3-d:2',3'-d']-s-indaceno[1,2-b:5,6-b']dithiophene unit raises the HOMO level of the homopolymer when compared with the indenofluorene homopolymer. This is expected to result in improved charge-injection into the polymer when applied as an organic semiconductor in transistor devices. Additionally, the HOMO level for the homopolymer is expected to be inherently lower than that of P3HT and other polythiophene materials, so that the polymer has improved oxidative stability.

iii) The optoelectronic properties of conjugated polymers vary significantly based upon the intrinsic electron density within each repeating unit and the degree of conjugation between the repeating units along the polymer backbone. By fusing additional aromatic rings along the long axis of the tetraalkylated dithieno[2,3-d:2',3'-d']-s-indaceno[1,2-b:5,6-b']dithiophene structure, the conjugation within the resultant monomers and consequently along the polymers can be extended, and the impact of potential "twists" between repeating units can be minimised. Both the features of additional aromatic rings and a reduced number of potential "twists" along polymer chains i.e. the increased rigidity of the polymer backbone, are expected to favourably reduce the reorganisation energy of the polymer and consequently increase the charge-carrier mobility.

iv) The tetraalkylated dithieno[2,3-d:2',3'-d']-s-indaceno[1,2-b:5,6-b']dithiophene unit inherently possesses C2 symmetry which is expected to permit the polymers to pack in an ordered manner and thereby result in high charge-carrier mobility.

v) Additional fine-tuning and further modification of the tetraalkylated dithieno[2,3-d:2',3'-d']-s-indaceno[1,2-b:5,6-b']dithiophene unit or co-polymerisation with appropriate co-monomer(s) can afford candidate materials for organic electronic applications.

The synthesis of the oligomers, homopolymers, and co-polymers can be achieved based on methods that are known to the skilled person and described in the literature, as will be further illustrated herein.

Above and below, the term "polymer" generally means a molecule of high relative molecular mass, the structure of which essentially comprises the multiple repetition of units derived, actually or conceptually, from molecules of low relative molecular mass (*Pure Appl. Chem.*, 1996, 68, 2291). The term "oligomer" generally means a molecule of intermediate relative molecular mass, the structure of which essentially comprises a small plurality of units derived, actually or conceptually, from molecules of lower relative molecular mass (*Pure Appl. Chem.*, 1996, 68, 2291). In a preferred sense according to the present invention a polymer means a compound having >1, i.e. at least 2 repeating units, preferably ≥5 repeating units, and an oligomer means a compound with >1 and <10, preferably <5, repeating units.

Above and below, in a formula showing a unit or a polymer, like formula I and its subformulae, an asterisk ("*") denotes a linkage to an adjacent unit or group, and in case of a polymer a link to an adjacent repeating unit or to a terminal group in the polymer chain.

The terms "repeating unit" and "monomeric unit" mean the constitutional repeating unit (CRU), which is the smallest constitutional unit the repetition of which constitutes a regular macromolecule, a regular oligomer molecule, a regular block or a regular chain (*Pure Appl. Chem.*, 1996, 68, 2291).

The term "small molecule" means a monomeric compound which typically does not contain a reactive group by which it can be reacted to form a polymer, and which is designated to be used in monomeric form. In contrast thereto, the term "monomer" unless stated otherwise means a monomeric compound that carries one or more reactive functional groups by which it can be reacted to form a polymer.

The terms "donor"/"donating" and "acceptor"/"accepting", unless stated otherwise, mean an electron donor or electron acceptor, respectively. "Electron donor" means a chemical entity that donates electrons to another compound or another group of atoms of a compound. "Electron acceptor" means a chemical entity that accepts electrons transferred to it from another compound or another group of atoms of a compound. (see also U.S. Environmental Protection Agency, 2009, Glossary of technical terms, http://www.epa.gov/oust/cat/TUMGLOSS.HTM).

The term "leaving group" means an atom or group (charged or uncharged) that becomes detached from an atom in what is considered to be the residual or main part of the molecule taking part in a specified reaction (see also *Pure Appl. Chem.*, 1994, 66, 1134).

The term "conjugated" means a compound containing mainly C atoms with $sp^2$-hybridisation (or optionally also sp-hybridisation), which may also be replaced by hetero atoms. In the simplest case this is for example a compound with alternating C—C single and double (or triple) bonds, but does also include compounds with units like 1,4-phenylene. "Mainly" means in this connection that a compound with naturally (spontaneously) occurring defects, which may lead to interruption of the conjugation, is still regarded as a conjugated compound.

Unless stated otherwise, the molecular weight is given as the number average molecular weight $M_n$ or weight average molecular weight $M_W$, which is determined by gel permeation chromatography (GPC) against polystyrene standards in eluent solvents such as tetrahydrofuran, trichloromethane (TCM, chloroform), chlorobenzene or 1,2,4-trichloro-benzene. Unless stated otherwise, 1,2,4-trichlorobenzene is used as solvent. The degree of polymerization, also referred to as total number of repeating units, n, means the number average degree of polymerization given as $n=M_n/M_U$, wherein $M_n$ is the number average molecular weight and $M_U$ is the molecular weight of the single repeating unit, see J. M. G. Cowie, *Polymers: Chemistry & Physics of Modern Materials*, Blackie, Glasgow, 1991.

The term "hydrocarbyl group" as used above and below denotes any monovalent or multivalent organic radical moiety which comprises at least one carbon atom and at least one H atom, and optionally one or more hetero atoms such as N, O, S, P, Si, Se, As, Te or Ge.

The term "hetero atom" means an atom in an organic compound that is not a H- or C-atom, and preferably means N, O, S, P, Si, Se, As, Te or Ge.

A hydrocarbyl group comprising a chain of 3 or more C atoms may be straight-chain, branched and/or cyclic, including spiro and/or fused rings.

Preferred hydrocarbyl groups include alkyl, alkoxy, aklycarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from N, O, S, P, Si, Se, As, Te and Ge.

Aryl and heteroaryl preferably denote a mono-, bi- or tricyclic aromatic or heteroaromatic group with 4 to 30 ring C atoms that may also comprise condensed rings and is optionally substituted with one or more groups L, wherein L is selected from halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, P-Sp-, optionally substituted silyl or hydrocarbyl with 1 to 40 C atoms that is optionally substituted and optionally comprises one or more hetero atoms, and is preferably alkyl, alkoxy, thiaalkyl, alkylcarbonyl, alkoxycarbonyl or alkoxycarbonyloxy with 1 to 20 C atoms that is optionally fluorinated, and R$^0$, R$^{00}$, X$^0$, P and Sp have the meanings given above and below.

Very preferred substituents L are selected from halogen, most preferably F, or alkyl, alkoxy, oxaalkyl, thioalkyl, fluoroalkyl and fluoroalkoxy with 1 to 12 C atoms or alkenyl, alkynyl with 2 to 12 C atoms.

Especially preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred rings are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene preferably 2-thiophene, selenophene, preferably 2-selenophene, thieno[3,2-b]thiophene, indole, isoindole, benzofuran, benzothiophene, benzodithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, all of which can be unsubstituted, mono- or polysubstituted with L as defined above. Further examples of heteroaryl groups are those selected from the following formulae An alkyl or alkoxyradical, i.e. where the terminal CH$_2$ group is replaced by —O—, can be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

An alkenyl group, wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4Z-heptenyl, 5-hexenyl, 6-heptenyl and the like. Groups having up to 5 C atoms are generally preferred.

An oxaalkyl group, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example. Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —C(O)O— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e. where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

A fluoroalkyl group is preferably perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$, or partially fluorinated alkyl, in particular 1,1-difluoroalkyl, all of which are straight-chain or branched.

The above-mentioned alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethyl-hexoxy, 1-methylhexoxy, 2-octyloxy, 2-oxa-3-methylbutyl, 3-oxa-4-methyl-pentyl, 4-methylhexyl, 2-hexyl, 2-octyl, 2-nonyl, 2-decyl, 2-dodecyl, 6-meth-oxyoctoxy, 6-methyloctoxy, 6-methyloctanoyloxy, 5-methylheptyloxy-carbonyl, 2-methylbutyryloxy, 2-methylvaleroyloxy, 4-methylhexanoyloxy, 2-chloropropionyloxy, 2-chloro-3-methylbutyryloxy, 2-chloro-4-methyl-valeryl-oxy, 2-chloro-3-methylvaleryloxy, 2-methyl-3-oxapentyl, 2-methyl-3-oxa-hexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In another preferred embodiment of the present invention, the hydrocarbyl groups are independently of each other selected from primary, secondary or tertiary alkyl or alkoxy with 1 to 30 C atoms, wherein one or more H atoms are optionally replaced by F, or aryl, aryloxy, heteroaryl or heteroaryloxy that is optionally alkylated or alkoxylated and has 4 to 30 ring atoms. Very preferred groups of this type are selected from the group consisting of the following formulae

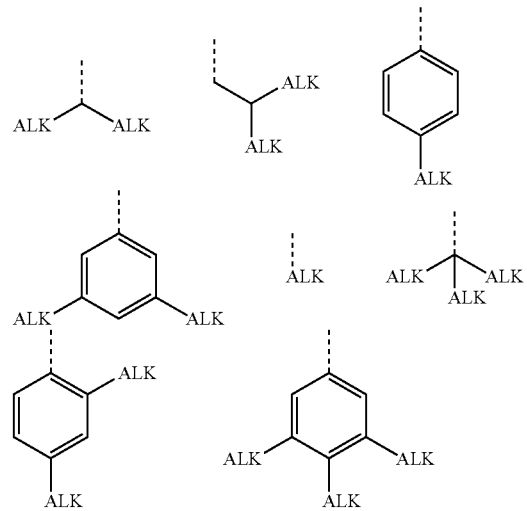

wherein "ALK" denotes optionally fluorinated, preferably linear, alkyl or alkoxy with 1 to 20, preferably 1 to 12 C-atoms, in case of tertiary groups very preferably 1 to 9 C atoms, and the dashed line denotes the link to the ring to which these groups are attached. Especially preferred among these groups are those wherein all ALK subgroups are identical.

—$CY^1$=$CY^2$— is preferably —CH=CH—, —CF=CF— or —CH=C(CN)—.

Halogen is F, Cl, Br or I, preferably F, Cl or Br.

—CO—, —C(=O)— and —C(O)— denote a carbonyl group, i.e.

The compounds, units and polymers according to the present invention may also be substituted with a polymerisable or crosslinkable reactive group, which is optionally protected during the process of forming the polymer. Particular preferred units polymers of this type are those comprising one or more units of formula I wherein one or more of $R^{1-4}$ denote or contain a group P-Sp-. These units and polymers are particularly useful as semiconductors or charge transport materials, as they can be crosslinked via the groups P, for example by polymerisation in situ, during or after processing the polymer into a thin film for a semiconductor component, to yield crosslinked polymer films with high charge carrier mobility and high thermal, mechanical and chemical stability.

Preferably the polymerisable or crosslinkable group P is selected from $CH_2$=$CW^1$—C(O)—O—, $CH_2$=$CW^1$—C(O)—,

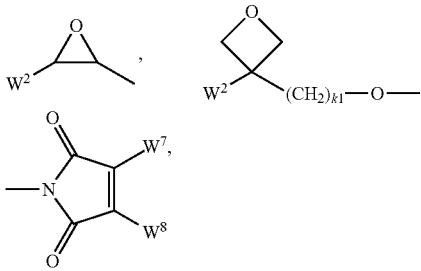

$CH_2$=$CW^2$—(O)$_{k1}$—, $CW^1$=CH—C(O)—(O)$_{k3}$—, $CW^1$=CH—C(O)—NH—, $CH_2$=$CW^1$—C(O)—NH—, $CH_3$—CH=CH—O—, ($CH_2$=CH)$_2$CH—OC(O)—, ($CH_2$=CH—$CH_2$)$_2$CH—O—C(O)—, ($CH_2$=CH)$_2$CH—O—, ($CH_2$=CH—$CH_2$)$_2$N—, ($CH_2$=CH—$CH_2$)$_2$N—C(O)—, HO—$CW^2W^3$—, HS—$CW^2W^3$—, $HW^2$N—, HO—$CW^2W^3$—NH—, $CH_2$=CH—(C(O)—O)$_{k1}$-Phe-(O)$_{k2}$—, $CH_2$=CH—(C(O))$_{k1}$-Phe-(O)$_{k2}$—, Phe-CH=CH—, HOOC—, OCN—, and $W^4W^5W^6$Si—, with $W^1$ being H, F, Cl, CN, $CF_3$, phenyl or alkyl with 1 to 5 C-atoms, in particular H, Cl or $CH_3$, $W^2$ and $W^3$ being independently of each other H or alkyl with 1 to 5 C-atoms, in particular H, methyl, ethyl or n-propyl, $W^4$, $W^5$ and $W^6$ being independently of each other Cl, oxaalkyl or oxacarbonylalkyl with 1 to 5 C-atoms, $W^7$ and $W^8$ being independently of each other H, Cl or alkyl with 1 to 5 C-atoms, Phe being 1,4-phenylene that is optionally substituted by one or more groups L as defined above, $k_1$, $k_2$ and $k_3$ being independently of each other 0 or 1, $k_3$ preferably being 1, and $k_4$ being an integer from 1 to 10.

Alternatively P is a protected derivative of these groups which is non-reactive under the conditions described for the process according to the present invention. Suitable protective groups are known to the ordinary expert and described in the literature, for example in Green, "Protective Groups in Organic Synthesis", John Wiley and Sons, New York (1981), like for example acetals or ketals.

Especially preferred groups P are $CH_2$=CH—C(O)—O—, $CH_2$=C($CH_3$)—C(O)—O—, $CH_2$=CF—C(O)—O—, $CH_2$=CH—O—, ($CH_2$=CH)$_2$CH—O—C(O)—, ($CH_2$=CH)$_2$CH—O—,

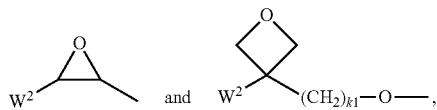

or protected derivatives thereof. Further preferred groups P are selected from the group consisting of vinyloxy, acrylate, methacrylate, fluoroacrylate, chloracrylate, oxetan and epoxy groups, very preferably from an acrylate or methacrylate group.

Polymerisation of group P can be carried out according to methods that are known to the ordinary expert and described in the literature, for example in D. J. Broer; G. Challa; G. N. Mol, *Macromol. Chem.*, 1991, 192, 59.

The term "spacer group" is known in prior art and suitable spacer groups Sp are known to the ordinary expert (see e.g. *Pure Appl. Chem.*, 2011, 73(5), 888. The spacer group Sp is preferably of formula Sp'-X', such that P-Sp- is P-Sp'-X'—, wherein Sp+ is alkylene with up to 30 C atoms which is unsubstituted or mono- or polysubstituted by F, Cl, Br, I or CN, it being also possible for one or more non-adjacent $CH_2$ groups to be replaced, in each case independently from one another, by —O—, —S—, —NH—, —$NR^0$—, —$SiR^0R^{00}$—, —C(O)—, —C(O)O—, —OC(O)—, —OC(O)—O—, —S—C(O)—, —C(O)—S—, —CH=CH— or —C≡C— in such a manner that O and/or S atoms are not linked directly to one another, X' is —O—, —S—, —C(O)—, —C(O)O—, —OC(O)—, —O—C(O)O—, —C(O)—$NR^0$—, —$NR^0$—C(O)—, —$NR^0$—C(O)—$NR^{00}$—, —$OCH_2$—, —$CH_2$O—, —$SCH_2$—, —$CH_2$S—, —$CF_2$O—, —$OCF_2$—, —$CF_2$S—, —$SCF_2$—, —$CF_2CH_2$—, —$CH_2CF_2$—, —$CF_2CF_2$—, —CH=N—, —N=CH—, —N=N—, —CH=$CR^0$—, —$CY^1$=$CY^2$—, —C≡C—, —CH=CH—C(O)O—, —OC(O)—CH=CH— or a single bond, $R^0$ and $R^{00}$ are independently of each other H or alkyl with 1 to 12 C-atoms, and $Y^1$ and $Y^2$ are independently of each other H, F, Cl or CN.

X' is preferably —O—, —S—, —$OCH_2$—, —$CH_2$O—, —$SCH_2$—, —$CH_2$S—, —$CF_2$O—, —$OCF_2$—, —$CF_2$S—, —$SCF_2$—, —$CH_2CH_2$—, —$CF_2CH_2$—, —$CH_2CF_2$—, —$CF_2CF_2$—, —CH=N—, —N=CH—, —N=N—, —CH=$CR^0$—, —$CY^1$=$CY^2$—, —C≡C— or a single bond, in particular —O—, —S—, —C≡C—, —$CY^1$=$CY^2$— or a single bond. In another preferred embodiment X' is a group that is able to form a conjugated system, such as —C≡C— or —CY$^1$=CY$^2$—, or a single bond.

Typical groups Sp' are, for example, —(CH$_2$)$_p$—, —(CH$_2$CH$_2$O)$_q$—CH$_2$CH$_2$—, —CH$_2$CH$_2$—S—CH$_2$CH$_2$— or —CH$_2$CH$_2$—NH—CH$_2$CH$_2$— or —(SiR$^0$R$^{00}$—O)$_p$—, with p being an integer from 2 to 12, q being an integer from 1 to 3 and R$^0$ and R$^{00}$ having the meanings given above.

Preferred groups Sp' are ethylene, propylene, butylene, pentylene, hexylene, heptylene, octylene, nonylene, decylene, undecylene, dodecylene, octadecylene, ethylene-oxyethylene, methyleneoxybutylene, ethylene-thioethylene, ethylene-N-methyl-iminoethylene, 1-methylalkylene, ethenylene, propenylene and butenylene for example.

Substituted aryl or heteroaryl is preferably substituted by one or more groups L, wherein L is selected from P-Sp-, F, Cl, Br, I, —OH, —CN, —NO$_2$, —NCO, —NCS, —OCN, —SCN, —C(=O)NR$^0$R$^{00}$, —C(=O)X$^0$, —C(=O)R$^0$, —NR$^0$R$^{00}$, C(=O)OH, optionally substituted aryl or heteroaryl having 4 to 20 ring atoms, or straight chain, branched or cyclic alkyl with 1 to 20, preferably 1 to 12 C atoms wherein one or more non-adjacent CH$_2$ groups are optionally replaced, in each case independently from one another, by —O—, —S—, —NR$^0$—, —SiR$^0$R$^{00}$—, —C(=O)—, —C(=O)O—, —CY$^1$=CY$^2$— or —C≡C— in such a manner that O and/or S atoms are not linked directly to one another and which is unsubstituted or substituted with one or more F or Cl atoms or OH groups, and X$^0$ is halogen, preferably F, Cl or Br, and Y$^1$, Y$^2$, R$^0$ and R$^{00}$ have the meanings given above and below.

Preferably R in formula I denotes straight-chain or branched alkyl with 1 to 20 C atoms.

X in formula I is preferably C.

The compounds according to the present invention include monomers, oligomers and polymers.

Oligomers and polymers according to the present invention preferably comprise one or more units of formula I as defined above and below.

Preferred polymers according to the present invention comprise one or more repeating units of formula II:

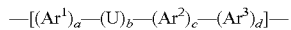  II wherein
U is a unit of formula I,
Ar$^1$, Ar$^2$, Ar$^3$ are, on each occurrence identically or differently, and independently of each other, aryl or heteroaryl that is different from U, preferably has 5 to 30 ring atoms, and is optionally substituted, preferably by one or more groups R$^S$,
R$^S$ is on each occurrence identically or differently F, Br, Cl, —CN, —NC, —NCO, —NCS, —OCN, —SCN, —C(O)NR$^0$R$^{00}$, —C(O)X$^0$, —C(O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl or hydrocarbyl with 1 to 40 C atoms that is optionally substituted and optionally comprises one or more hetero atoms, or P-Sp-,
R$^0$ and R$^{00}$ are independently of each other H or optionally substituted C$_{1-40}$ hydrocarbyl, and preferably H or alkyl with 1 to 12 C-atoms,
P is a polymerisable or crosslinkable group,
Sp is a spacer group or a single bond,
X$^0$ is halogen, preferably F, Cl or Br,
a, b and c are on each occurrence identically or differently 0, 1 or 2,
d is on each occurrence identically or differently 0 or an integer from 1 to 10,
wherein the polymer comprises at least one repeating unit of formula II wherein b is at least 1.

Further preferred polymers according to the present invention comprise, in addition to the units of formula I or II, one or more repeating units selected from monocyclic or polycyclic aryl or heteroaryl groups that are optionally substituted.

These additional repeating units are preferably selected of formula III

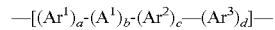  III wherein Ar$^1$, Ar$^2$, Ar$^3$, a, b, c and d are as defined in formula II, and A$^1$ is an aryl or heteroaryl group that is different from U and Ar$^{1-3}$, preferably has 5 to 30 ring atoms, is optionally substituted by one or more groups R$^S$ as defined above and below, and is preferably selected from aryl or heteroaryl groups having electron acceptor properties, wherein the polymer comprises at least one repeating unit of formula III wherein b is at least 1.

R$^S$ preferably has one of the meanings given for R$^1$.

The conjugated polymers according to the present invention are preferably selected of formula IV:

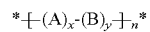  IV wherein
A is a unit of formula I or II,
B is a unit that is different from A and comprises one or more aryl or heteroaryl groups that are optionally substituted, and is preferably selected of formula III,
x is >0 and ≤1,
y is ≥0 and <1,
x+y is 1, and
n is an integer>1.

Preferred polymers of formula IV are selected of the following formulae

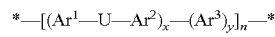  IVa

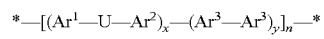  IVb

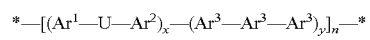  IVc

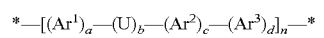  IVd

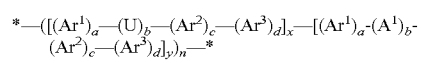  IVe wherein U, Ar$^1$, Ar$^2$, Ar$^3$, a, b, c and d have in each occurrence identically or differently one of the meanings given in formula II, A$^1$ has on each occurrence identically or differently one of the meanings given in formula III, and x, y and n are as defined in formula IV, wherein these polymers can be alternating or random copolymers, and wherein in formula IVd and IVe in at least one of the repeating units [(Ar$^1$)$_a$—(U)$_b$—(Ar$^2$)$_c$—(Ar$^3$)$_d$] and in at least one of the repeating units [(Ar$^1$)$_a$-(A$^1$)$_b$-(Ar$^2$)$_c$—(Ar$^3$)$_d$] b is at least 1.

In the polymers according to the present invention, the total number of repeating units n is preferably from 2 to 10,000. The total number of repeating units n is preferably ≥5, very preferably ≥10, most preferably ≥50, and preferably ≤500, very preferably ≤1,000, most preferably ≤2,000, including any combination of the aforementioned lower and upper limits of n.

The polymers of the present invention include homopolymers and copolymers, like statistical or random copolymers, alternating copolymers and block copolymers, as well as combinations thereof.

Especially preferred are polymers selected from the following groups:
Group A consisting of homopolymers of the unit U or (Ar¹—U) or (Ar¹—U—Ar²) or (Ar¹—U—Ar³) or (U—Ar²—Ar³) or (Ar¹—U—Ar²—Ar³), i.e. where all repeating units are identical,
Group B consisting of random or alternating copolymers formed by identical units (Ar¹—U—Ar²) and identical units (Ar³),
Group C consisting of random or alternating copolymers formed by identical units (Ar¹—U—Ar²) and identical units (A¹),
Group D consisting of random or alternating copolymers formed by identical units (Ar¹—U—Ar²) and identical units (Ar¹-A¹-Ar²), wherein in all these groups U, D¹, Ar¹, Ar² and Ar³ are as defined above and below, in groups A, B and C Ar¹, Ar² and Ar³ are different from a single bond, and in group D one of Ar¹ and Ar² may also denote a single bond.

Further preferred are copolymers selected from the group consisting of the following subformulae IV1
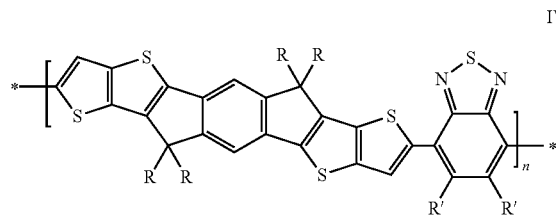

IV2
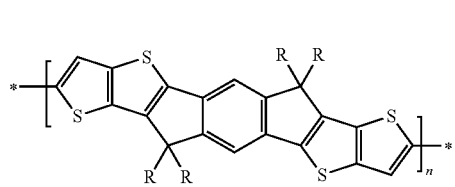

IV3
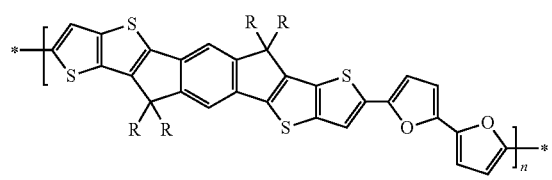

IV4
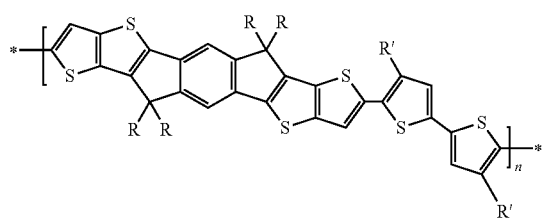

IV5
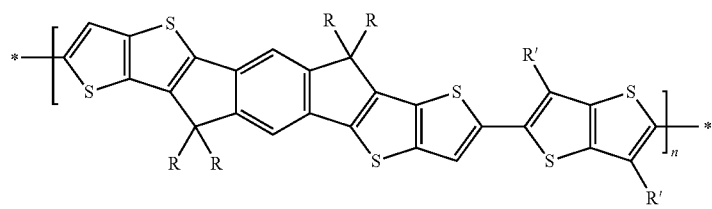

IV6
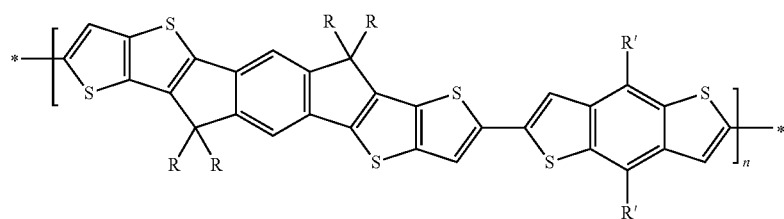

IV7
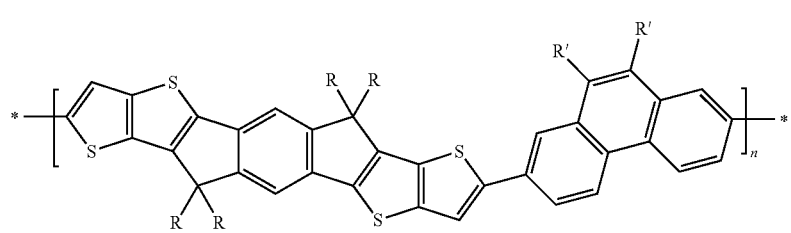

wherein R has on each occurrence identically or differently one of the meanings given in formula I and R' has on each occurrence identically or differently one of the meanings of $R^s$ given in formula II Further preferred are copolymers of formula IV1-IV7, wherein the two sp² carbon atoms in the cyclopentadiene rings are replaced by two Si atoms or by two Ge atoms.

Preferred polymers of formulae IV, IVa-IVe and IV1-IV7 are selected of formula V $$R^5\text{-chain-}R^6 \qquad \qquad V$$

wherein "chain" denotes a polymer chain of formulae IV, IVa-IVe or IV1-IV7, and $R^5$ and $R^6$ have independently of each other one of the meanings of $R^1$ as defined above, and preferably denote, independently of each other F, Br, Cl, H, —CH$_2$Cl, —CHO, —CH=CH$_2$, —SiR'R''R''', —SnR'R''R''', —BR'R'', —B(OR')(OR''), —B(OH)$_2$, —ZnCl, —MgCl, —MgBr or P-Sp-, wherein P and Sp are as defined above, and R', R'' and R''' have independently of each other one of the meanings of $R^0$ as defined above, and two of R', R'' and R''' may also form a ring together with the hetero atom to which they are attached.

In the polymers represented by formulae IV, IVa-IVe, IV1-IV7 and V, x denotes the mole fraction of units A, y denotes the mole fraction of units B, and n denotes the degree of polymerisation or total number of units A and B. These formulae includes block copolymers, random or statistical copolymers and alternating copoymers of A and B, as well as homopolymers of A for the case when x is >0 and y is 0.

Monomers according to the present invention preferably comprise a unit of formula I as defined above and below, and one or more reactive functional groups which are attached to the unit of formula I and which can be reacted to form a polymer.

Preferably the monomers are selected of formula VI $$R^9\text{—Ar}^1\text{—U—Ar}^2\text{—}R^{10} \qquad \qquad VI$$

wherein U, $Ar^1$ and $Ar^2$ have the meanings of formula II and V, or one of the preferred meanings as described above and below, and $R^9$ and $R^{10}$ independently of each other denote F, Br, Cl, —CH$_2$Cl, —CHO, —CH=CH$_2$, —SiR'R''R''', —SnR'R''R''', —BR'R'', —B(OR')(OR''), —B(OH)$_2$, —ZnCl, —MgCl, or —MgBr, wherein R', R'' and R''' have independently of each other one of the meanings of $R^0$ as defined above, and two of R', R'' and R''' may also form a ring together with the hetero atom to which they are attached.

Especially preferred are monomers of formula VI wherein $R^9$ and $R^{10}$ are, preferably independently of each other, selected from the group consisting of Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^3$)$_2$, —C≡CH, —C≡CSi(Z$^1$)$_3$, —ZnX and —Sn(Z$^4$)$_3$, wherein $Z^{1-4}$ are selected from the group consisting of alkyl and aryl, each being optionally substituted, and two groups $Z^2$ may also form a cyclic group, and X is a halogen atom.

Oligomeric compounds according to the present invention are preferably selected of formula VII

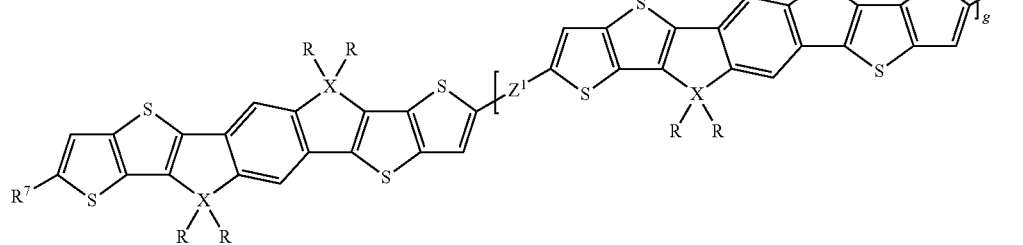

wherein R and X are as defined in formula I, $Z^1$ denotes a single bond, $(CY^1=CY^2)_h$, $(C≡C)_h$, wherein h=1 or 2, or $Ar^5$, wherein $Ar^5$ has one of the meanings of $Ar^1$ or $Ar^3$ as given in formula II or one of the preferred meanings of $Ar^1$ or $Ar^3$ as given above and below, $R^7$ and $R^8$ independently of each other denote H, F, Br, Cl, —CN, —NC, —NCO, —NCS, —OCN, —SCN, —C(O)NR$^0$R$^{00}$, —C(O)X$^0$, —C(O)R$^0$, —C(O)OR$^0$, —O—C(O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, P-Sp-, or optionally substituted silyl or hydrocarbyl with 1 to 40 C atoms that is optionally substituted and optionally comprises one or more hetero atoms, and wherein one or more C atoms are optionally replaced by a hetero atom, and $R^0$, $R^{00}$ and $X^0$ are as defined in formula II, and g is 1, 2 or 3.

Preferred oligomeric compounds of formula VII are those wherein X is C.

Further preferred oligomeric compounds of formula VII are those selected from the following formula:

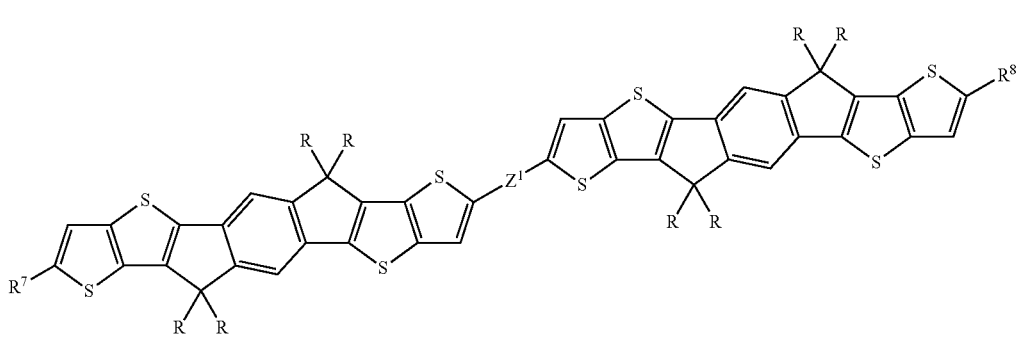

wherein R is as defined in formula VII, and Z has one of the meanings of $Z^1$ as given in formula VII.

Especially preferred are repeating units, monomers, oligomers and polymers of formulae I, II, III, IV, IVa-IVe, V, VI, VII and their subformulae, wherein one or more of $Ar^1$, $Ar^2$ and $Ar^3$ denote aryl or heteroaryl, preferably having electron donor properties, selected from the group consisting of the following formulae

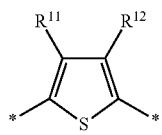 (D1)

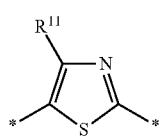 (D2)

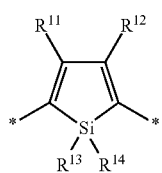 (D3)

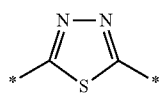 (D4)

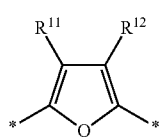 (D5)

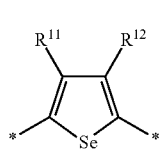 (D6)

-continued

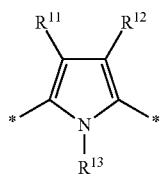 (D7)

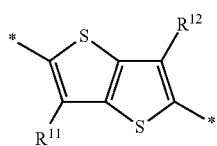 (D8)

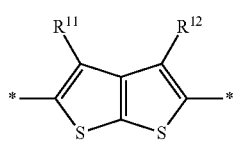 (D9)

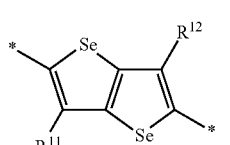 (D10)

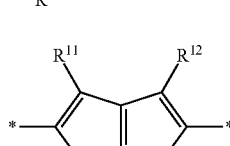 (D11)

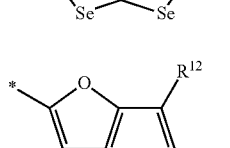 (D12)

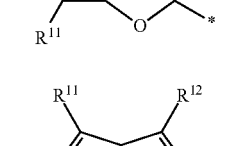 (D13)

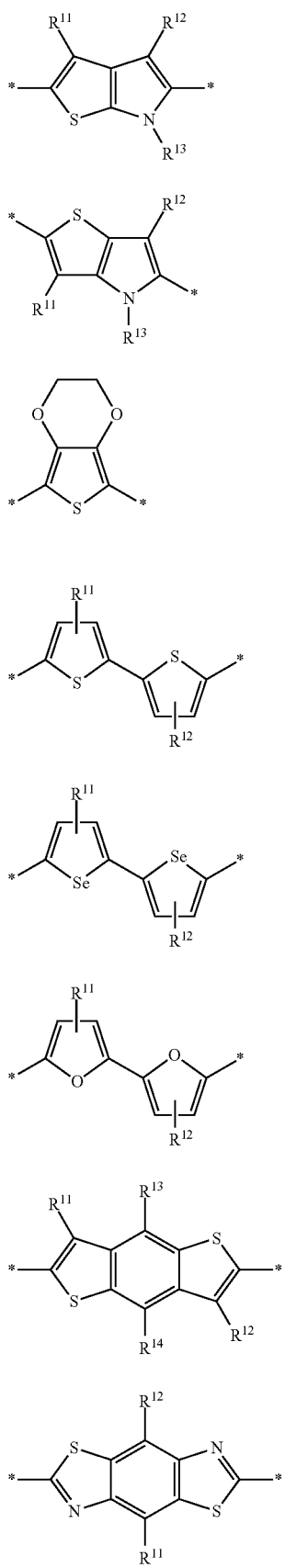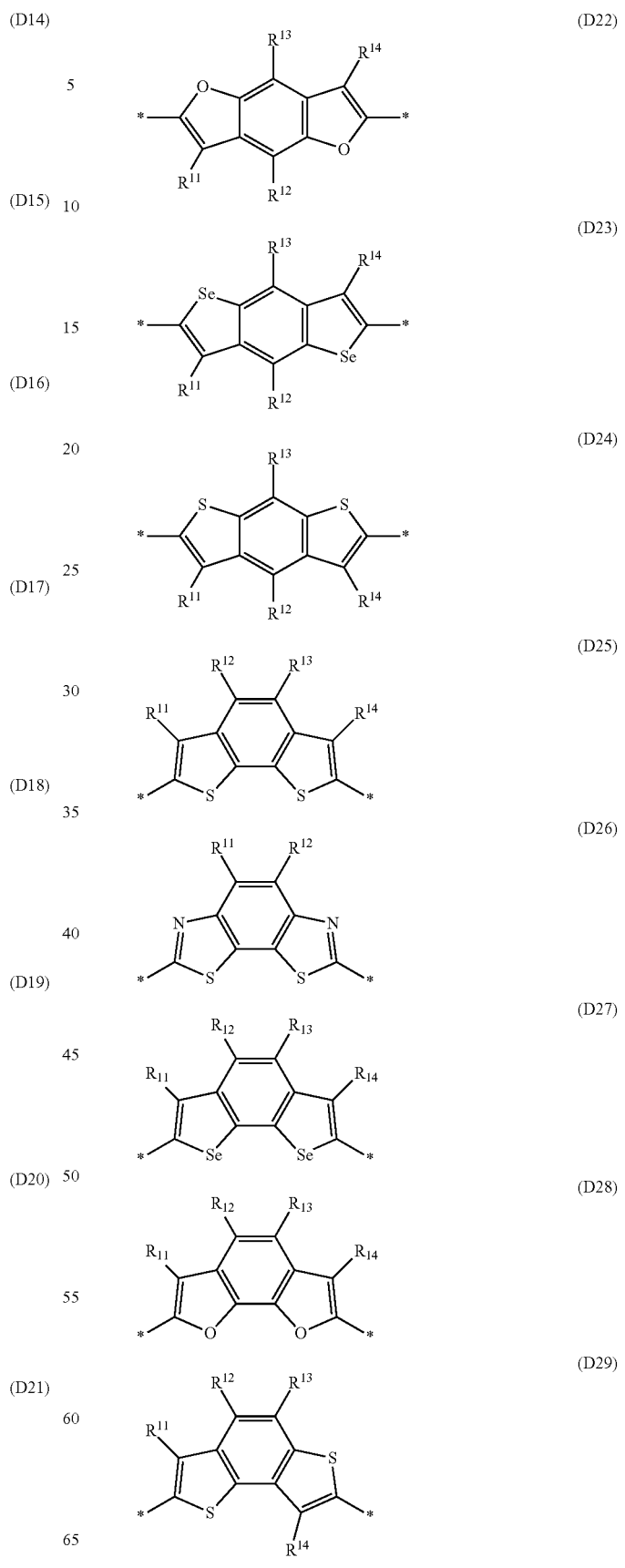

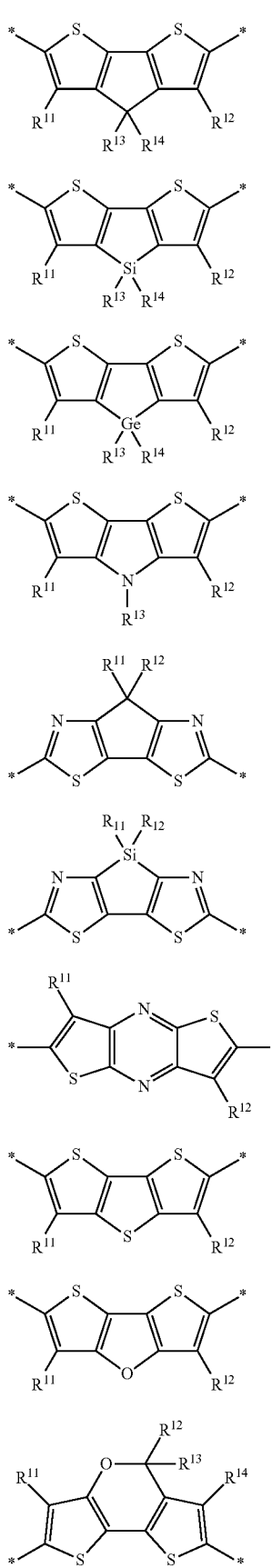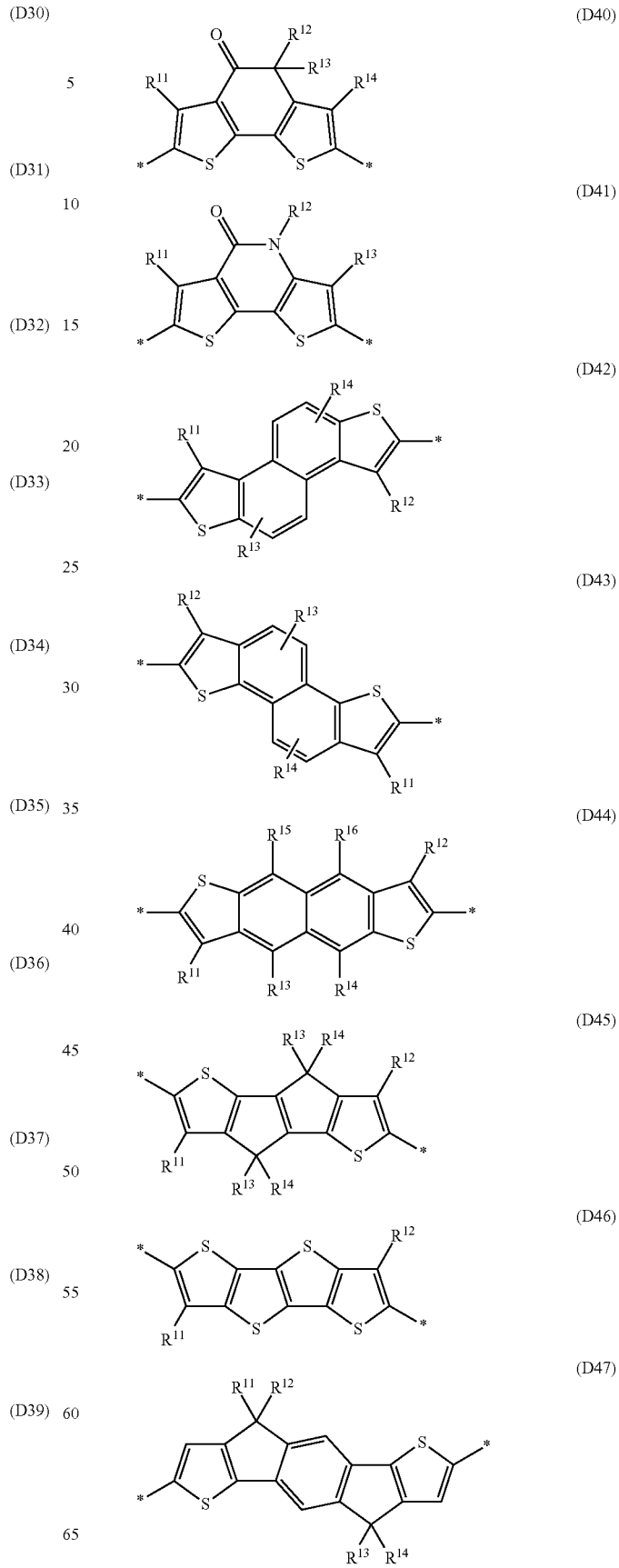

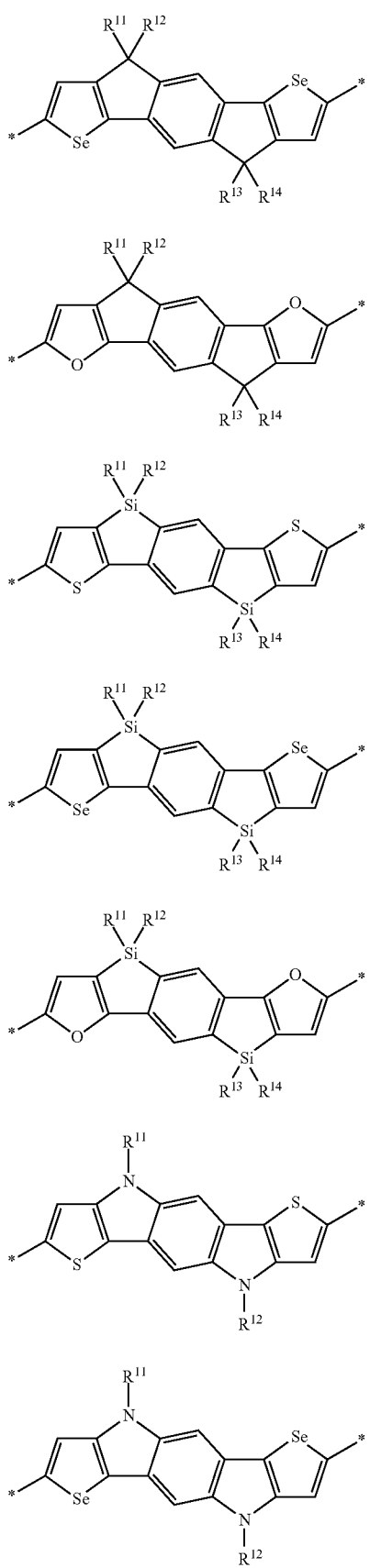
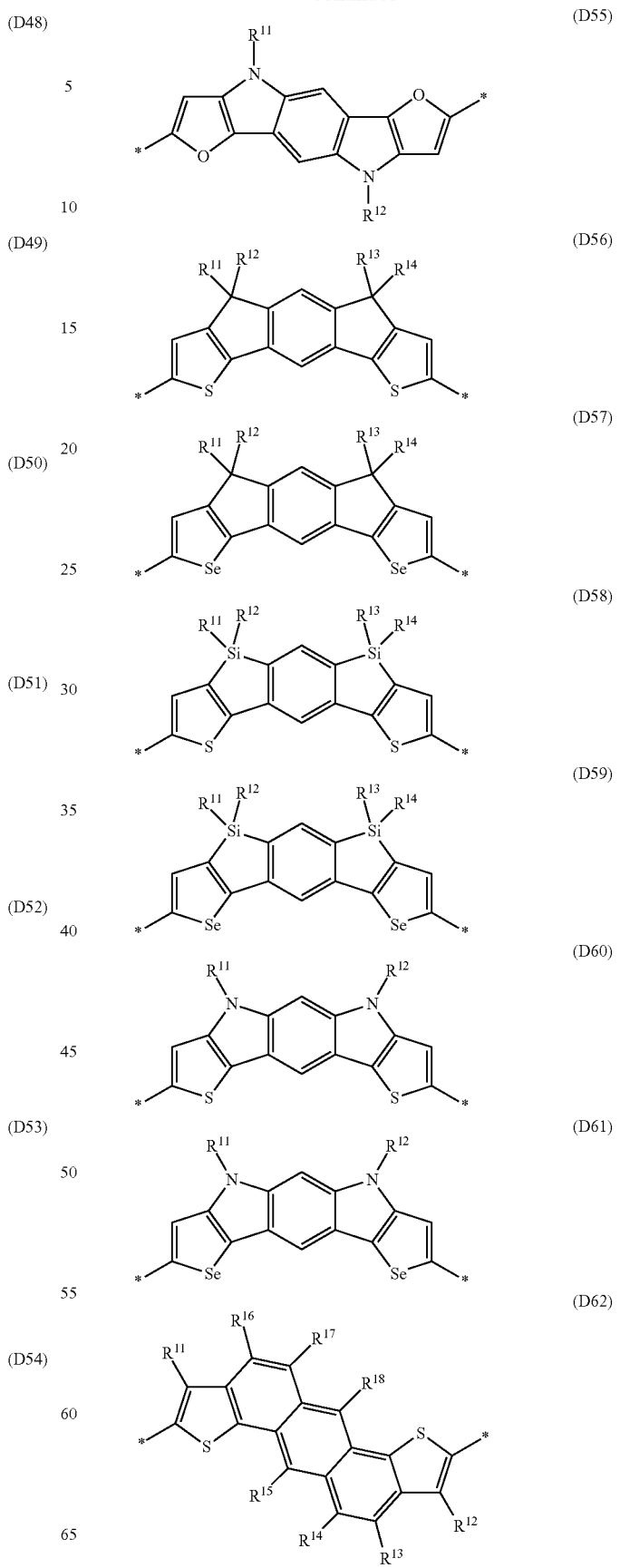

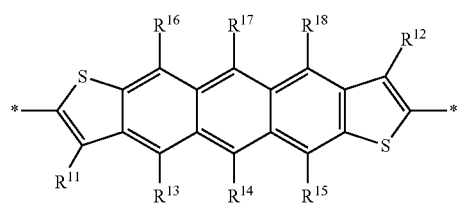
(D63)
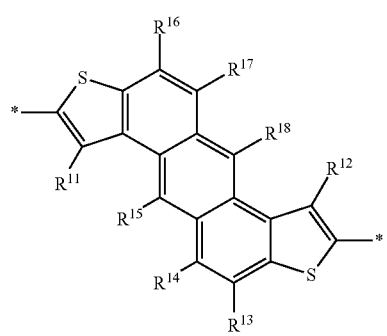
(D64)
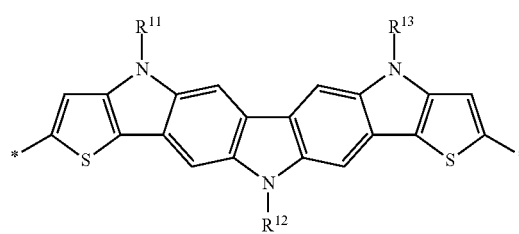
(D65)
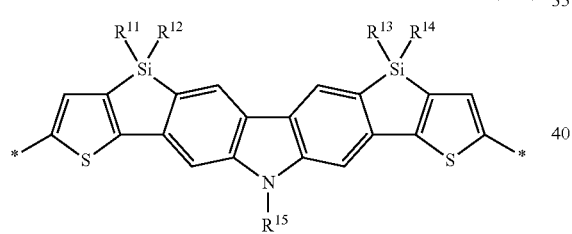
(D66)
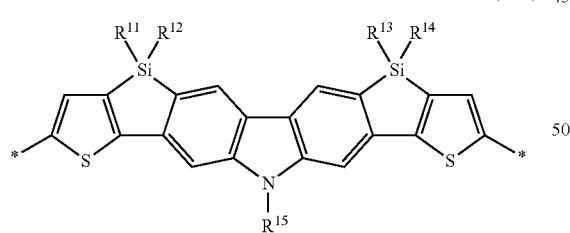
(D67)
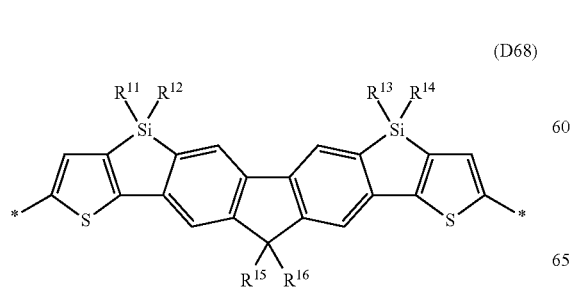
(D68)
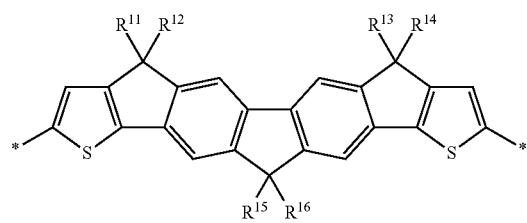
(D69)
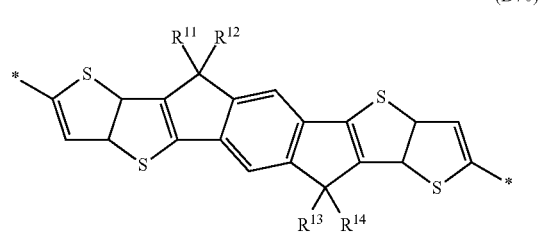
(D70)
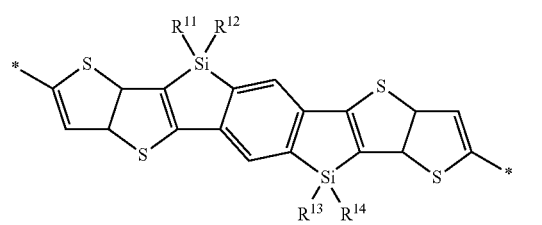
(D71)
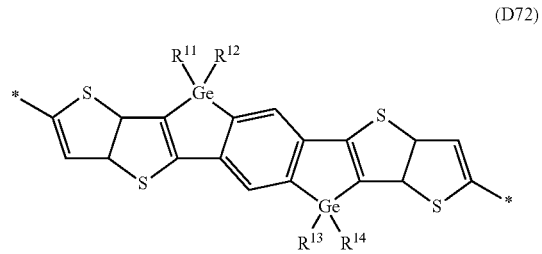
(D72)
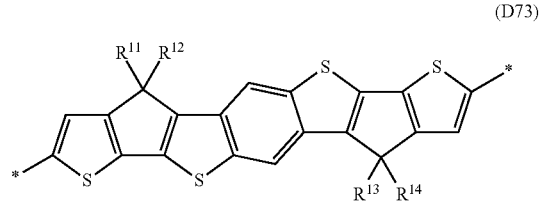
(D73)
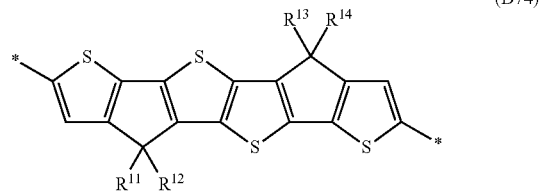
(D74)
(D75)

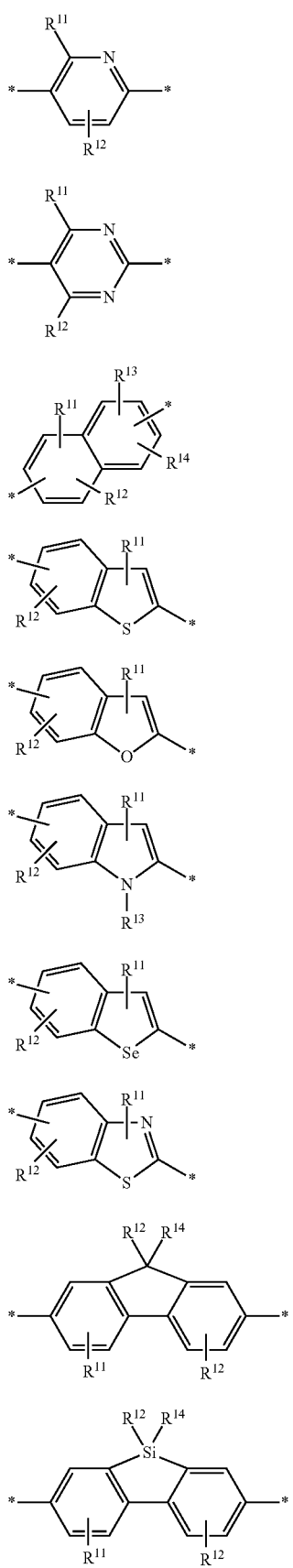
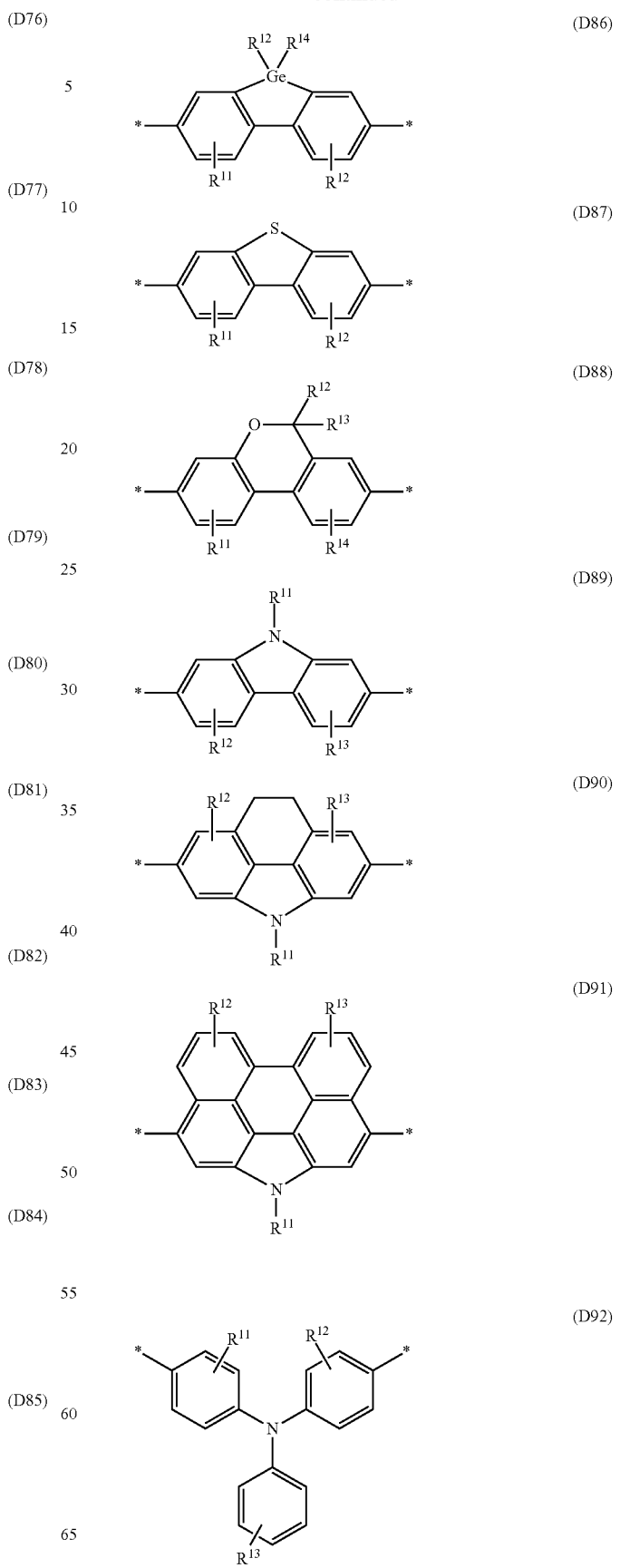

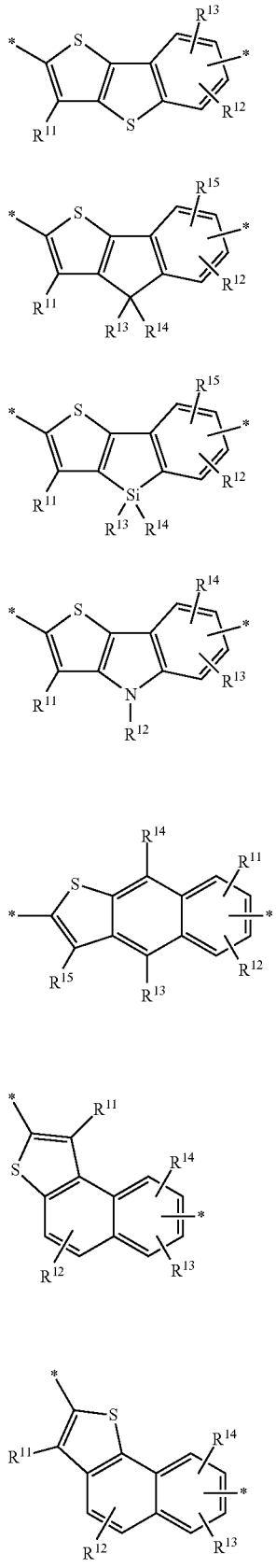
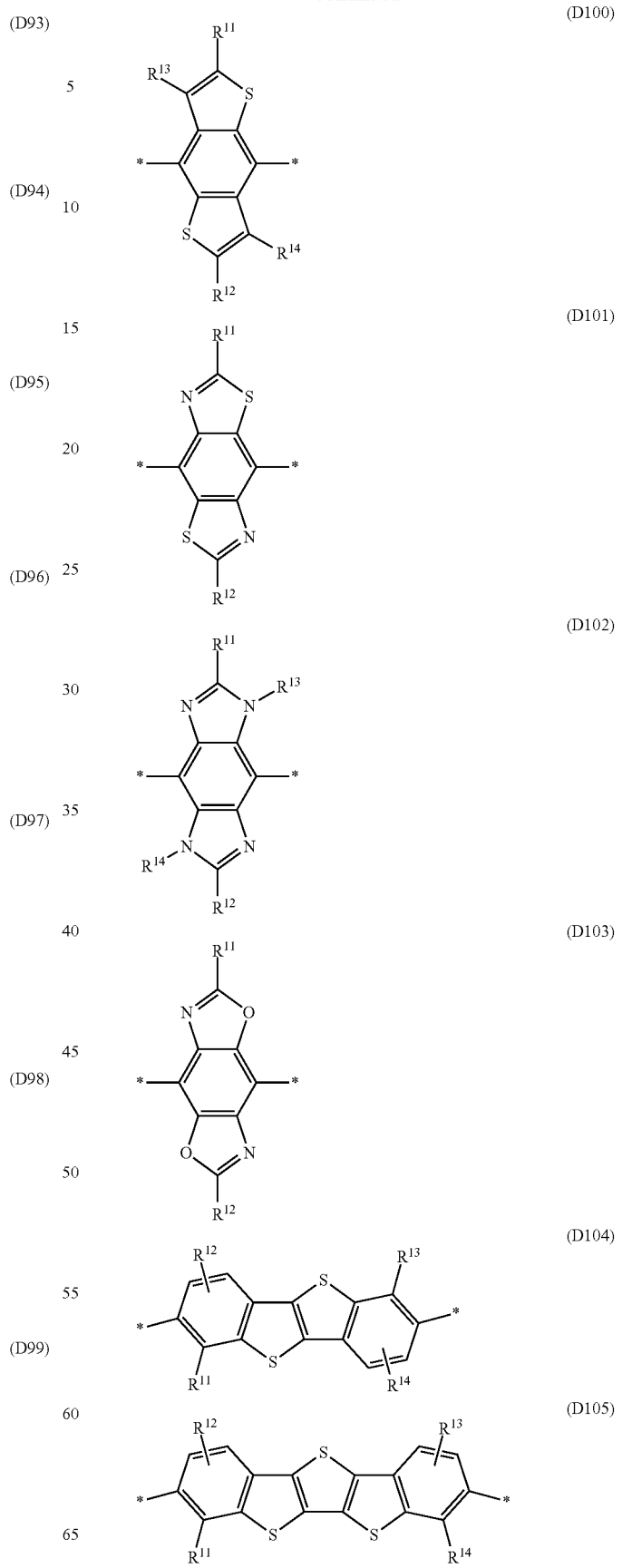

(D106) (D107) (D108) (D109) (D110) (D111) (D112) (D113) (D114) (D115) (D116) (D117) (D118) (D119)

(D120)

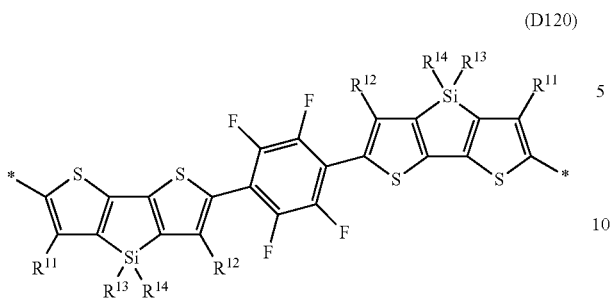

wherein $R^{11}$, $R^{12}$, $R^{13}$, $R^{14}$, $R^{15}$, $R^{16}$, $R^{17}$ and $R^{18}$ independently of each other denote H or have one of the meanings of $R^s$ as defined in formula II.

Especially preferred are repeating units, monomers, oligomers and polymers of formulae I, II, III, IV, IVa-IVe, V, VI, VII and their subformulae, wherein one or more of $Ar^3$ and $A^1$ denote aryl or heteroaryl, preferably having electron acceptor properties, selected from the group consisting of the following formulae (A1)

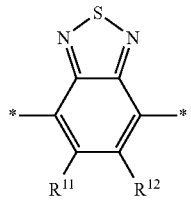

(A2)

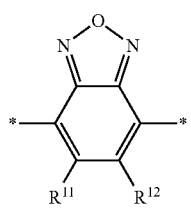

(A3)

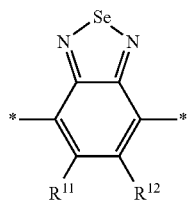

(A4)

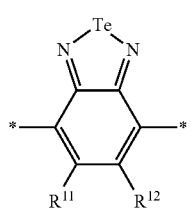

(A5)

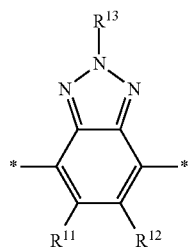

(A6)

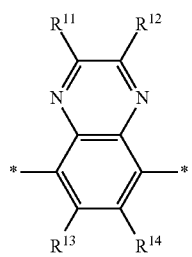

(A7)

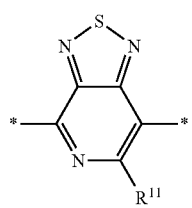

(A8)

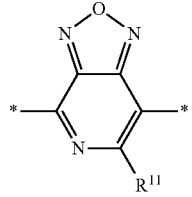

(A9)

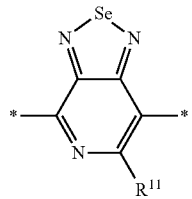

(A10)

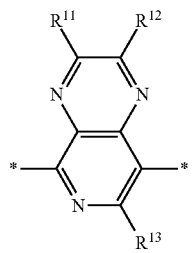

(A11)

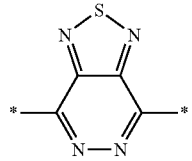

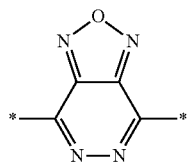
(A12)
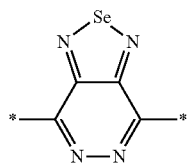
(A13)
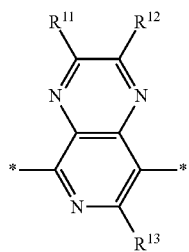
(A14)
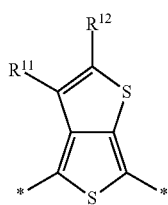
(A15)
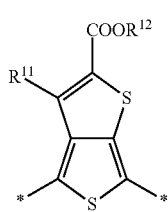
(A16)
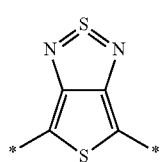
(A17)
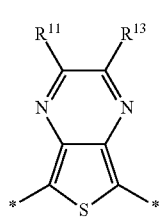
(A18)
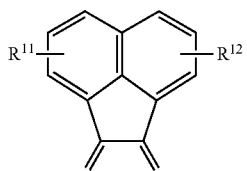
(A19)
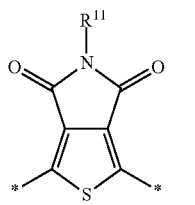
(A20)
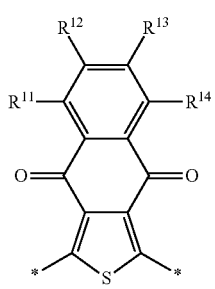
(A21)
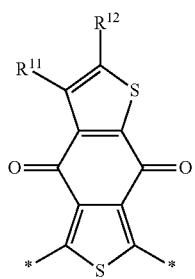
(A22)
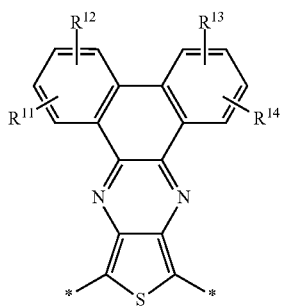
(A23)

-continued
(A24)
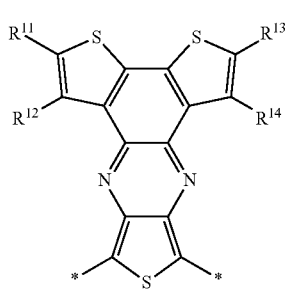
(A25)
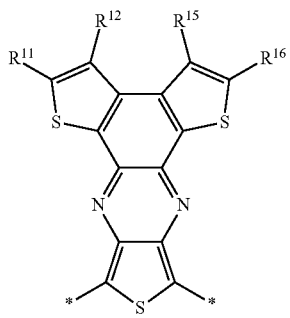
(A26)
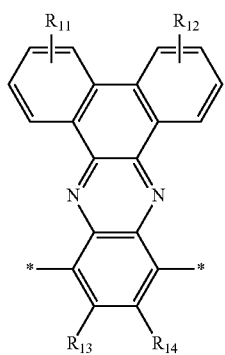
(A27)
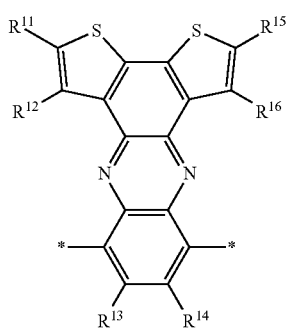
(A28)
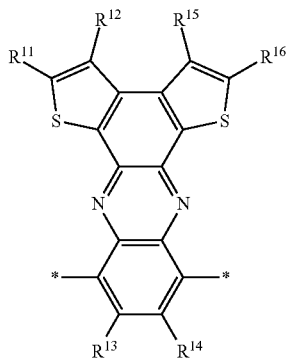
-continued
(A29)
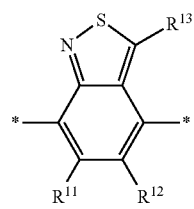
(A30)
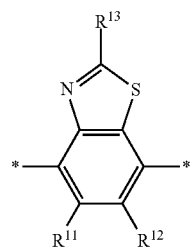
(A31)
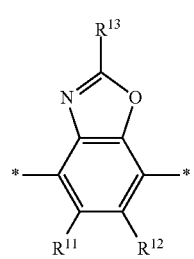
(A32)
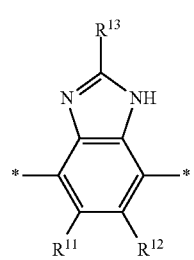
(A33)
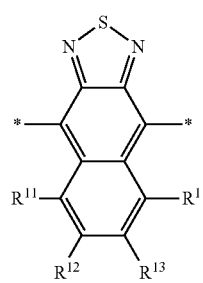
(A34)
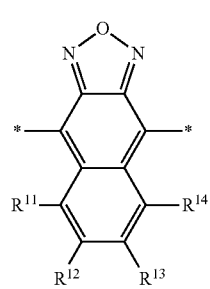

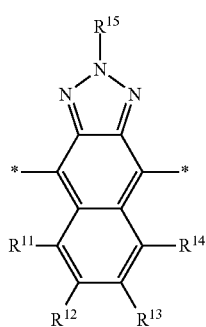
(A35)
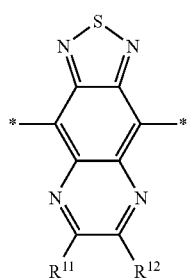
(A36)
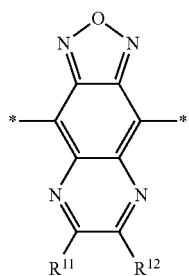
(A37)
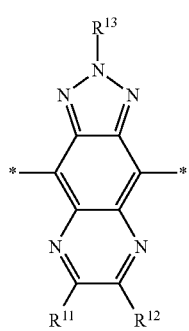
(A38)
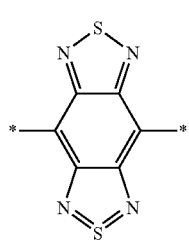
(A39)
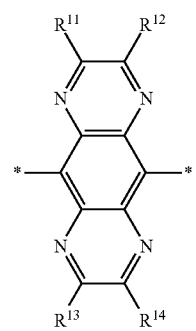
(A40)
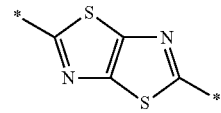
(A41)
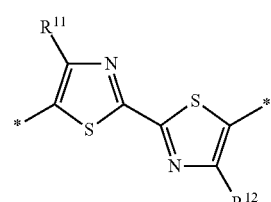
(A42)
(A43)
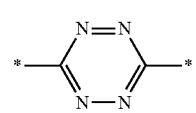
(A44)
(A45)
(A46)
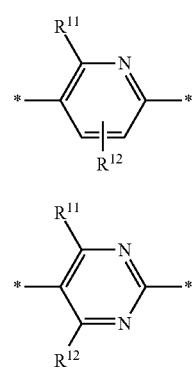
(A47)

(A48) 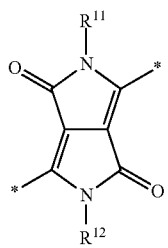
(A49) 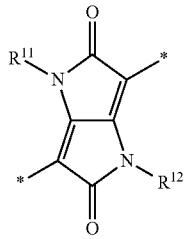
(A50) 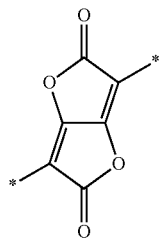
(A51) 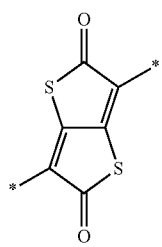
(A52) 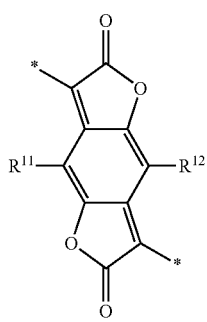
(A53) 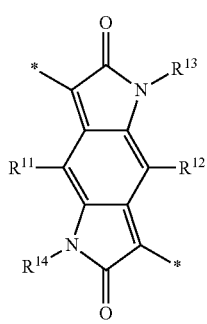
(A54) 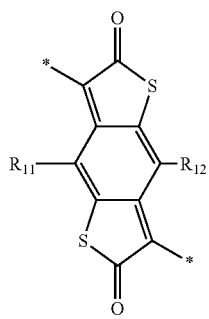
(A55) 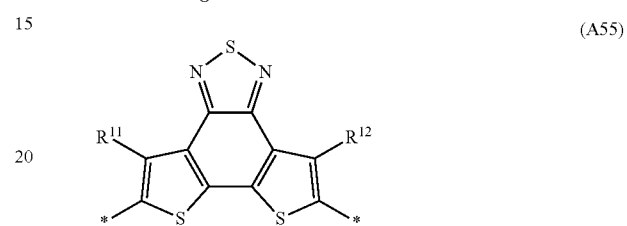
(A56) 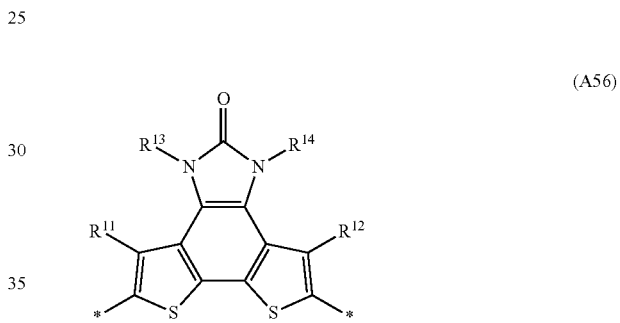
(A57) 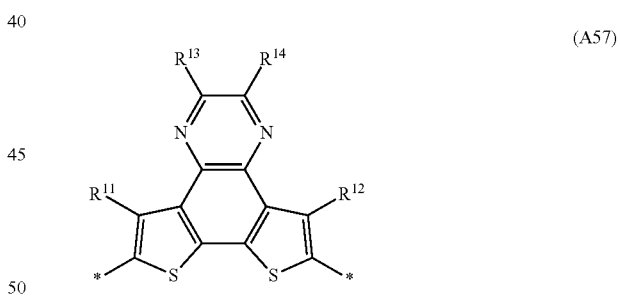
(A58) 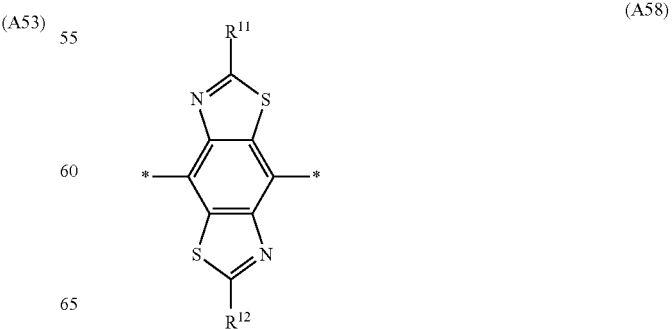

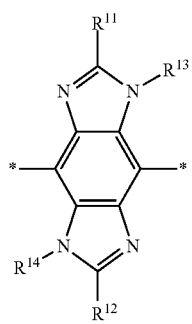 (A59)
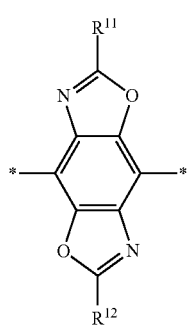 (A60)
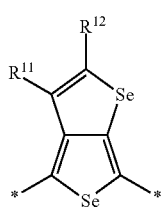 (A61)
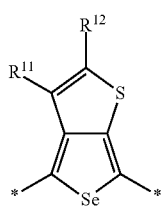 (A62)
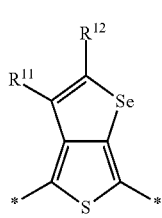 (A63)
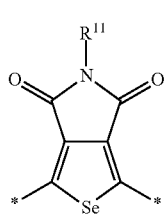 (A64)
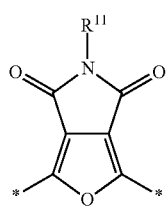 (A65)
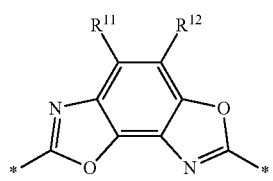 (A66)
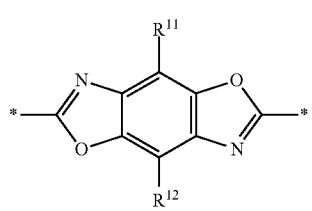 (A67)
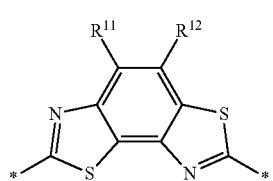 (A68)
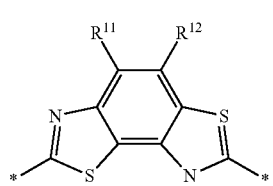 (A69)
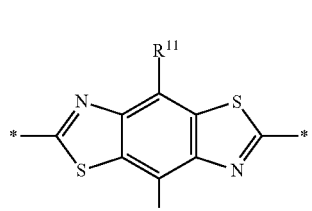 (A70)
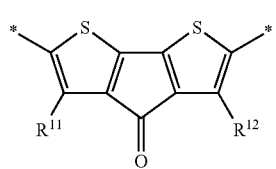 (A71)
(A72)

(A73) 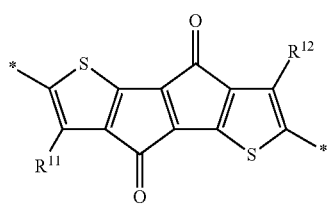
(A74) 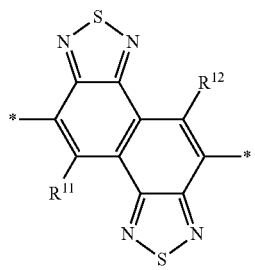
(A75) 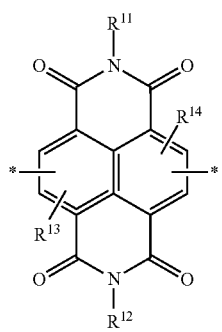
(A76) 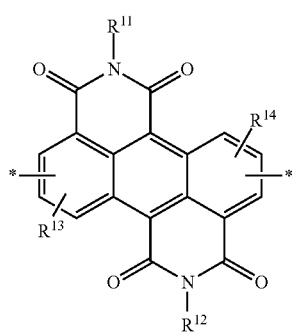
(A77) 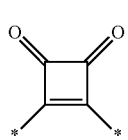
(A78) 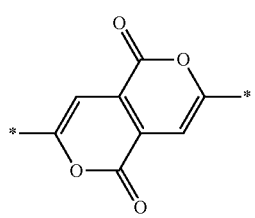
(A79) 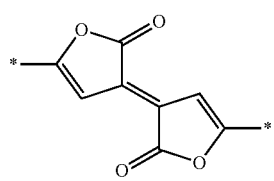
(A80) 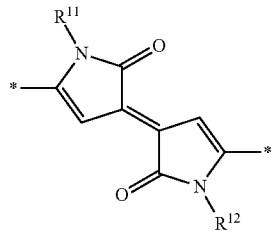
(A81) 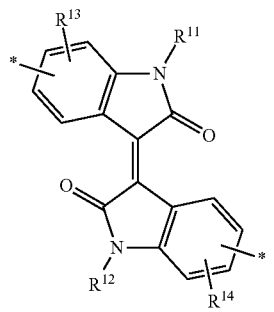
(A82) 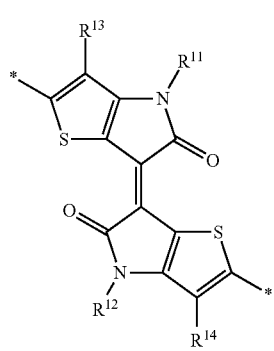
(A83) 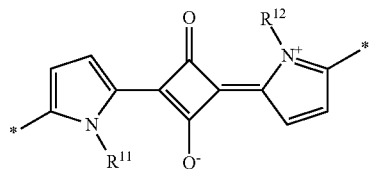

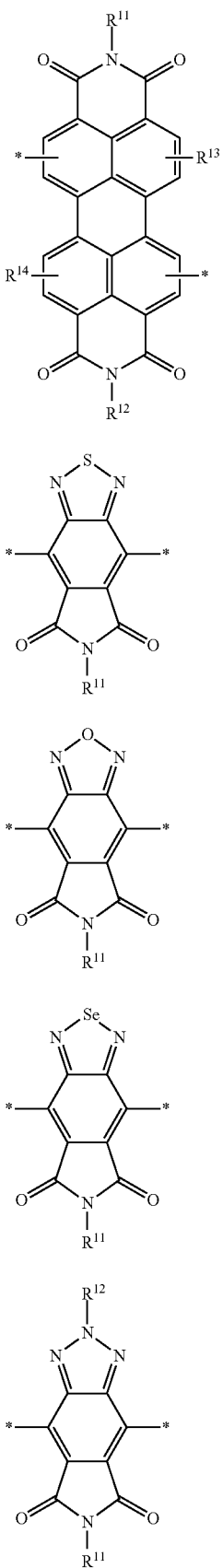

(A84)

(A85)

(A86)

(A87)

(A88)

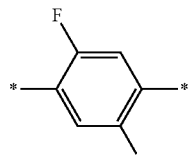

(A89)

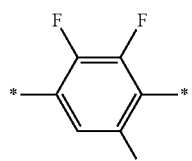

(A90)

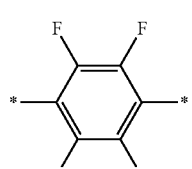

(A91)

wherein $R^{11}$, $R^{12}$, $R^{13}$, $R^{14}$, $R^{15}$ and $R^{16}$ independently of each other denote H or have one of the meanings of $R^s$ as defined in formula II.

Very preferred are repeating units, monomers, oligomers, and polymers of formulae I, IA, II, III, IV, IVa-IVe, IV1-IV14, V, VI, VII and their subformulae selected from the following list of preferred embodiments:

y is ≥0 and ≤1,
b=d=1 and a=c=0, preferably in all repeating units,
a=b=c=d=1, preferably in all repeating units,
a=b=d=1 and c=0, preferably in all repeating units,
a=b=c=1 and d=0, preferably in all repeating units,
a=c=2, b=1 and d=0, preferably in all repeating units,
a=c=2 and b=d=1, preferably in all repeating units,
X is C,
R is straight-chain or branched alkyl with 1 to 20 C atoms,
n is at least 5, preferably at least 10, very preferably at least 50, and up to 2,000, preferably up to 500.
$M_w$ is at least 5,000, preferably at least 8,000, very preferably at least 10,000, and preferably up to 300,000, very preferably up to 100,000,
$R^0$ and $R^{00}$ are selected from H or $C_1$-$C_{10}$-alkyl,
$R^5$ and $R^6$ are selected from H, halogen, —$CH_2Cl$, —CHO, —CH=$CH_2$—SiR'R"R'", —SnR'R"R'", —BR'R", —B(OR')(OR"), —B(OH)$_2$, P-Sp, $C_1$-$C_{20}$-alkyl, $C_1$-$C_{20}$-alkoxy, $C_2$-$C_{20}$-alkenyl, $C_1$-$C_{20}$-fluoroalkyl and optionally substituted aryl or heteroaryl,
$R^9$ and $R^{10}$ are, preferably independently of each other, selected from the group consisting of Cl, Br, I, O-tosylate, O-triflate, O-mesylate, O-nonaflate, —$SiMe_2F$, —$SiMeF_2$, —O—$SO_2Z^1$, —B(O$Z^2$)$_2$, —C$Z^3$=C(Z$^4$)$_2$, —C≡CH and —Sn(Z$^4$)$_3$, wherein $Z^{1-4}$ are selected from the group consisting of alkyl and aryl, each being optionally substituted, and two groups $Z^2$ may also form a cyclic group, very preferably from Br,
$R^7$ and $R^8$ denote H,
$R^7$ and/or $R^8$ denote F,
$R^S$, R' and $R^{11-18}$ are independently of each other, and on each occurrence identically or differently, selected from the group consisting of aryl, aryloxy, heteroaryl and heteroaryloxy, each of which is optionally fluorinated, alkylated or alkoxylated and has 4 to 30 ring atoms, $R^S$, R' and $R^{11-18}$ are independently of each other, and on each occurrence identically or differently, selected from the group consisting of primary alkyl, alkoxy or sulfanylalkyl with 1 to 30 C atoms, secondary alkyl, alkoxy or sulfanylalkyl with 3 to 30 C atoms, and tertiary alkyl, alkoxy or sulfanylalkyl with 4 to 30 C atoms, wherein in all these groups one or more H atoms are optionally replaced by F, $R^S$, R' and $R^{11-18}$ are independently of each other, and on each occurrence identically or differently, selected from the group consisting of alkylcarbonyl, alkoxycarbonyl and alkylcarbonyloxy, all of which are straight-chain or branched, are optionally fluorinated, and have from 1 to 30 C atoms, $R^S$, R' and $R^{11-18}$ independently of each other, and on each occurrence identically or differently, denote F, Cl, Br, I, CN, $R^9$, —C(O)—$R^9$, —C(O)—O—$R^9$, or —O—C(O)—$R^9$, —SO$_2$—$R^9$, —SO$_3$—$R^9$, wherein $R^9$ is straight-chain, branched or cyclic alkyl with 1 to 30 C atoms, in which one or more non-adjacent C atoms are optionally replaced by —O—, —S—, —C(O)—, —C(O)—O—, —O—C(O)—, —O—C(O)—O—, —SO$_2$—, —SO$_3$—, —CR$^0$=CR$^{00}$— or —C≡C— and in which one or more H atoms are optionally replaced by F, Cl, Br, I or CN, or $R^9$ is aryl or heteroaryl having 4 to 30 ring atoms which is unsubstituted or which is substituted by one or more halogen atoms or by one or more alkyl or alkoxy groups,—e and f are 0.

The polymers of the present invention can be synthesized according to or in analogy to methods that are known to the skilled person and are described in the literature. Other synthesis methods can be taken from the examples. For example, the polymers can be suitably prepared by aryl-aryl coupling reactions, such as Yamamoto coupling, Suzuki coupling, Stille coupling, Sonogashira coupling, Heck coupling or Buchwald coupling. Suzuki coupling and Yamamoto coupling are especially preferred.

The monomers which are polymerised to form the repeat units of the polymers, can be prepared according to methods which are known to the person skilled in the art.

Preferably the polymers are prepared from monomers of formula VI or its preferred embodiments as described above and below.

Another aspect of the invention is a process for preparing a polymer by coupling one or more identical or different monomeric units of formula I or monomers of formula VI with each other and/or with one or more comonomers in a polymerisation reaction, preferably in an aryl-aryl coupling reaction.

Suitable and preferred comonomers are selected from the following formulae $R^9$—Ar$^3$—$R^{10}$      C1

$R^9$-A$^1$-$R^{10}$      C2 wherein Ar$^3$ has one of the meanings of formula II or one of the preferred meanings given above and below, A$^1$ has one of the meanings of formula III or one of the preferred meanings given above and below, and $R^9$ and $R^{10}$ have one of the meanings of formula V different from H, and preferably denote reactive functional groups like for example halogen, stannyl and boronate groups as defined in formula V.

Preferred methods for polymerisation are those leading to C—C-coupling or C—N-coupling, like Suzuki polymerisation, as described for example in WO 00/53656, Yamamoto polymerisation, as described in for example in T. Yamamoto et al., *Prog. Polym. Sci.*, 1993, 17, 1153-1205 or in WO 2004/022626 A1, and Stille coupling. For example, when synthesizing a linear polymer by Yamamoto polymerisation, monomers as described above having two reactive halide groups $R^9$ and $R^{10}$ is preferably used. When synthesizing a linear polymer by Suzuki polymerisation, preferably a monomer as described above is used wherein at least one reactive group $R^9$ or $R^{10}$ is a boronic acid or boronic acid derivative group.

Suzuki polymerisation may be used to prepare homopolymers as well as statistical, alternating and block random copolymers. Statistical or block copolymers can be prepared for example from the above monomers of formula V wherein one of the reactive groups $R^9$ and $R^{10}$ is halogen and the other reactive group is a boronic acid or boronic acid derivative group. The synthesis of statistical, alternating and block copolymers is described in detail for example in WO 03/048225 A2 or WO 2005/014688 A2.

Suzuki polymerisation employs a Pd(0) complex or a Pd(II) salt. Preferred Pd(0) complexes are those bearing at least one phosphine ligand such as Pd(Ph$_3$P)$_4$. Another preferred phosphine ligand is tris(ortho-tolyl)phosphine, i.e. Pd(o-Tol)$_3$. Preferred Pd(II) salts include palladium acetate, i.e. Pd(OAc)$_2$. Suzuki polymerisation is performed in the presence of a base, for example sodium carbonate, potassium phosphate or an organic base such as tetraethylammonium carbonate. Yamamoto polymerisation employs a Ni(0) complex, for example bis(1,5-cyclooctadienyl) nickel(0).

As alternatives to halogens as described above, leaving groups of formula —O— SO$_2$Z$^1$ can be used wherein Z$^1$ is as described above. Particular examples of such leaving groups are tosylate, mesylate and triflate.

Especially suitable and preferred synthesis methods of the repeating units, monomers, and polymers of formula I, II, III, IV, V and VI are illustrated in the synthesis schemes shown below, wherein R and X are as defined in formula I.

The synthesis of the unfunctionalised monomer is exemplarily shown in Scheme 1.

Scheme 1

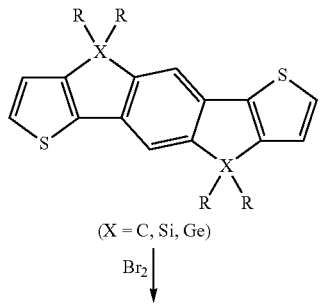

(X = C, Si, Ge)

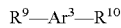

53
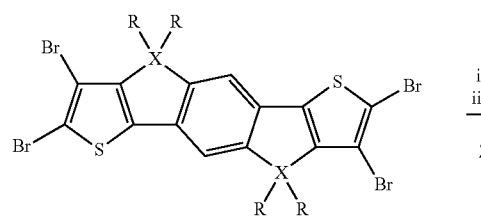
-continued
54
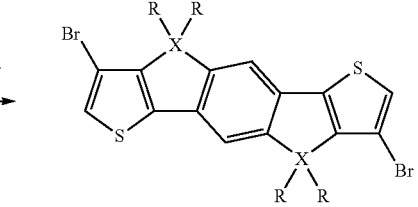
i) Lithiation
ii) H+
or
Zn/HOAc
i) Lithiation
ii) DMF
i) LDA
ii) DMF
Pd₂dba₃/Xantphos
HSCH₂COOEt/DIPEA
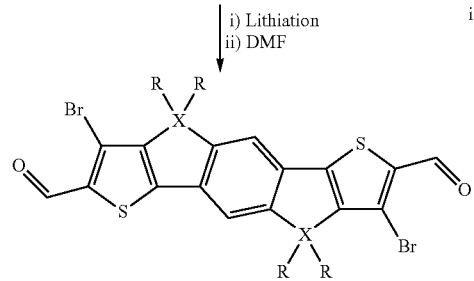
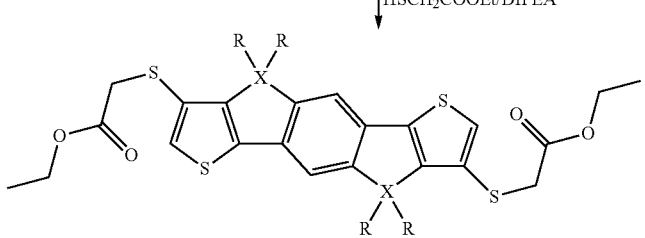
K₂CO₃/CuO/DMF
HSCH₂COOEt
NaOH
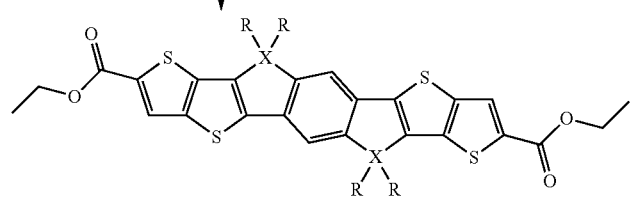
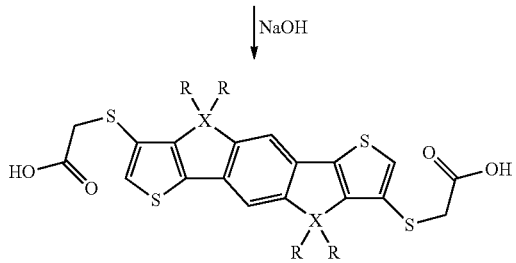
NaOH
i) Oxalyl chloride   iii) NaBH₄
ii) AlCl₃              iv) HCl
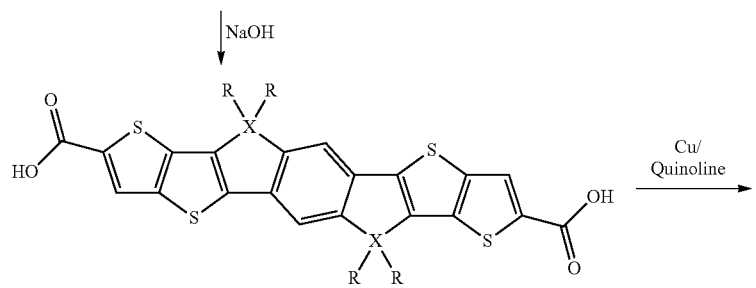
Cu/
Quinoline
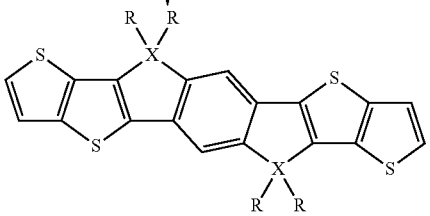
A synthesis scheme for the functionalisation of the monomer is exemplarily shown in Scheme 2.
Scheme 2
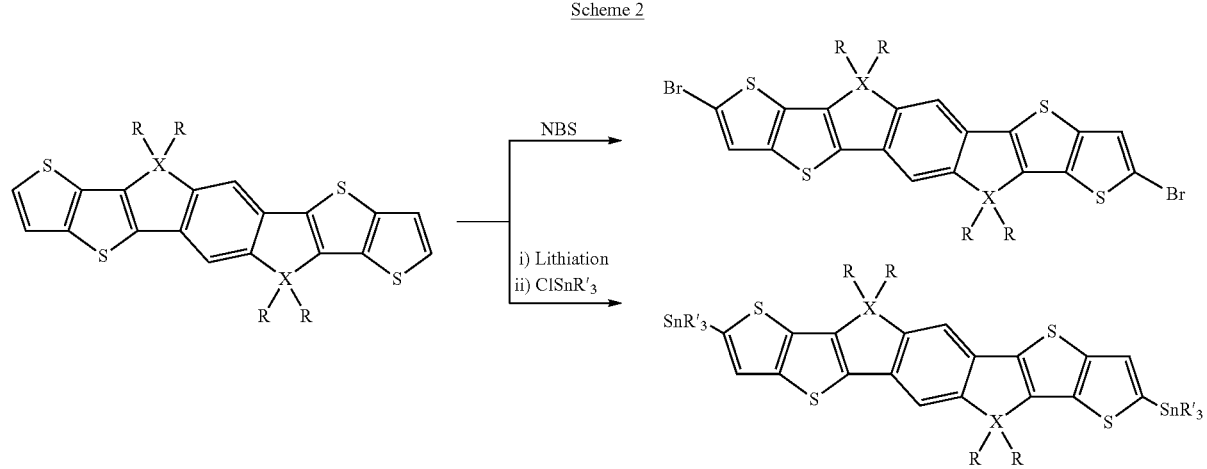

A synthesis scheme for the homopolymerisation of the monomer is exemplarily shown in Scheme 3.
Scheme 3
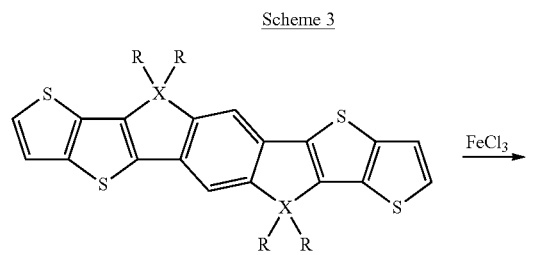
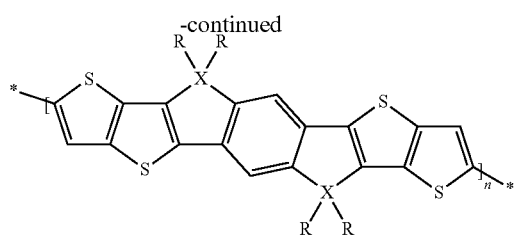
A synthesis scheme for the co-polymerisation of the monomer is exemplarily shown in Scheme 4 (alternating co-polymers) and Scheme 5 (statistical block co-polymers).
Scheme 4
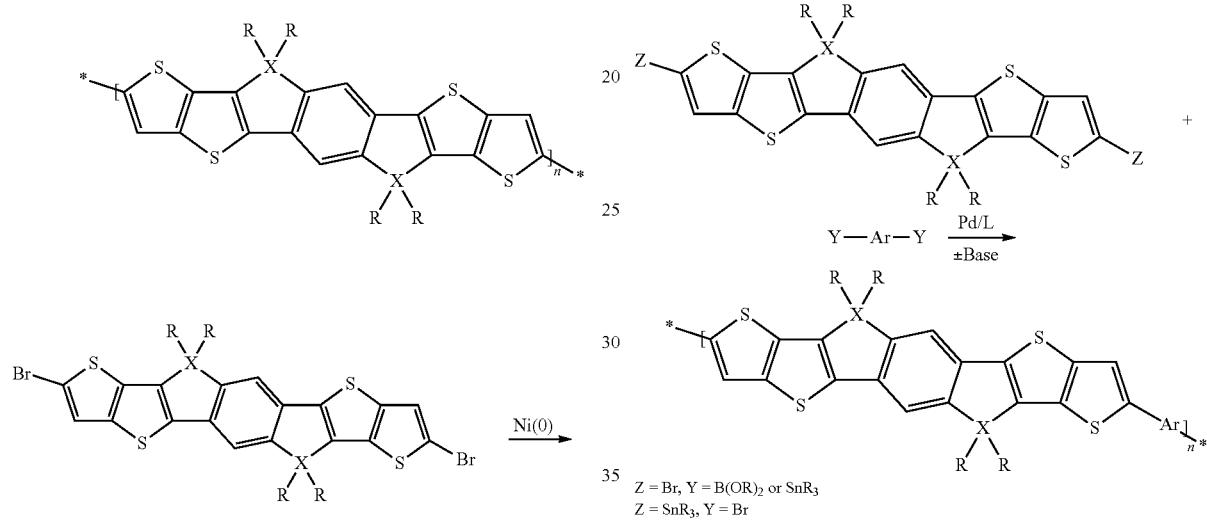
Z = Br, Y = B(OR)$_2$ or SnR$_3$
Z = SnR$_3$, Y = Br
Scheme 5
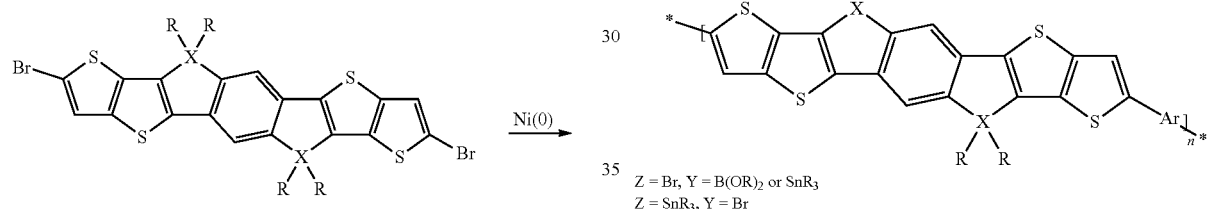
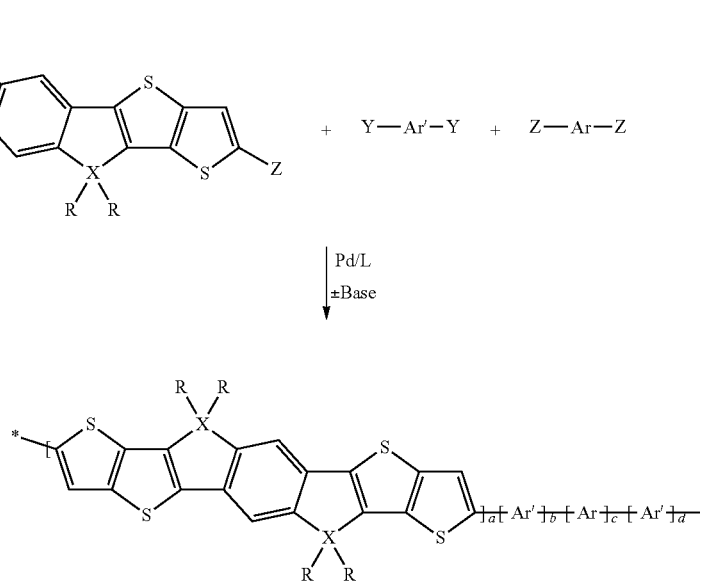
Z = Br, Y = B(OR)$_2$ or SnR$_3$
Z = SnR$_3$, Y = Br The novel methods of preparing monomers and polymers as described above and below are another aspect of the invention.

The oligomers and polymers according to the present invention can also be used in mixtures or polymer blends, for example together with monomeric compounds or together with other polymers having charge-transport, semiconducting, electrically conducting, photoconducting and/or light emitting semiconducting properties, or for example with polymers having hole blocking or electron blocking properties for use as interlayers or charge blocking layers in OLED devices. Thus, another aspect of the invention relates to a polymer blend comprising one or more polymers according to the present invention and one or more further polymers having one or more of the above-mentioned properties. These blends can be prepared by conventional methods that are described in prior art and known to the skilled person. Typically the polymers are mixed with each other or dissolved in suitable solvents and the solutions combined.

Another aspect of the invention relates to a formulation comprising oligomers, polymers, mixtures or polymer blends as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetra-methyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, dimethylformamide, 2-chloro-6fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzo-nitrile, 2,5-dimethylanisole, 2,4-dimethylanisole, benzonitrile, 3,5-dimethyl-anisole, N,N-dimethylaniline, ethyl benzoate, 1-fluoro-3,5-dimethoxy-benzene, 1-methylnaphthalene, N-methylpyrrolidinone, 3-fluorobenzo-trifluoride, benzotrifluoride, benzotrifluoride, diosane, trifluoromethoxy-benzene, 4-fluorobenzotrifluoride, 3-fluoropyridine, toluene, 2-fluoro-toluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluorobenzene, 3-chlorofluorobenzene, 1-chloro-2,5-difluorobenzene, 4-chlorofluorobenzene, chloro-benzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents and solvent mixtures with high boiling temperatures are preferred. For spin coating alkylated benzenes like xylene and toluene are preferred.

Examples of especially preferred solvents include, without limitation, dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetraline, decaline, indane, methyl benzoate, ethyl benzoate, mesitylene and/or mixtures thereof.

The concentration of the oligomers or polymers in the solution is preferably 0.1 to 10% by weight, more preferably 0.5 to 5% by weight. Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., *Journal of Paint Technology*, 1966, 38 (496), 296". Solvent blends may also be used and can be identified as described in "*Solvents*, W. H. Ellis, Federation of Societies for Coatings Technology, p 9-10, 1986". Such a procedure may lead to a blend of 'non' solvents that will dissolve both the polymers of the present invention, although it is desirable to have at least one true solvent in a blend.

The oligomers and polymers according to the present invention can also be used in patterned OSC layers in the devices as described above and below. For applications in modern microelectronics it is generally desirable to generate small structures or patterns to reduce cost (more devices/unit area), and power consumption. Patterning of thin layers comprising a polymer according to the present invention can be carried out for example by photolithography, electron beam lithography or laser patterning.

For use as thin layers in electronic or electrooptical devices the compounds, polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, dip coating, curtain coating, brush coating, slot dye coating or pad printing.

Ink-jet printing is particularly preferred when high resolution layers and devices needs to be prepared. Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the compounds or polymers should be first dissolved in a suitable solvent. Solvents must fulfil the requirements stated above and must not have any detrimental effect on the chosen print head. Additionally, solvents should have boiling points>100° C., preferably >140° C. and more preferably >150° C. in order to prevent operability problems caused by the solution drying out inside the print head. Apart from the solvents methoned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a oligomer or polymer according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the oligomer or polymer, which reduces or prevents clogging of the jets and separation of the components during spraying. The solvent(s) may include those selected from the following list of examples: dodecylbenzene, 1-methyl-4-tert-butylbenzene, terpineol limonene, isodurene, terpinolene, cymene, diethylbenzene. The solvent may be a solvent mixture, that is a combination of two or more solvents, each solvent preferably having a boiling point>100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The polymer blends and formulations according to the present invention can additionally comprise one or more further components or additives selected for for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The oligomers and polymers to the present invention are useful as charge transport, semiconducting, electrically conducting, photoconducting or light emitting materials in optical, electrooptical, electronic, electroluminescent or photoluminescent components or devices. In these devices, the polymers of the present invention are typically applied as thin layers or films.

Thus, the present invention also provides the use of the semiconducting oligomers, polymer, polymers blend, formulation or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising an oligomer, polymer, polymer blend or formulation according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising an oligomer, polymer, polymer blend, formulation or organic semiconducting layer according to the present invention. Especially preferred devices are OFETs, TFTs, ICs, logic circuits, capacitors, RFID tags, OLEDs, OLETs, OPEDs, OPVs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs and OPV devices, in particular bulk heterojunction (BHJ) OPV devices. In an OFET, for example, the active semiconductor channel between the drain and source may comprise the layer of the invention. As another example, in an OLED device, the charge (hole or electron) injection or transport layer may comprise the layer of the invention.

For use in OPV devices the oligomer or polymer according to the present invention is preferably used as photoactive layer. This implies the use in a formulation that comprises or contains, more preferably consists essentially of, very preferably exclusively of, a p-type (electron donor) semiconductor and an n-type (electron acceptor) semiconductor. The p-type semiconductor is constituted by a compound, preferably a polymer according to the present invention. The n-type semiconductor can be an inorganic material such as zinc oxide or cadmium selenide, or an organic material such as a fullerene derivate, for example (6,6)-phenyl-butyric acid methyl ester derivatized methano $C_{60}$ fullerene, also known as "PCBM" or "$C_{60}$PCBM", as disclosed for example in G. Yu, J. Gao, J. C. Hummelen, F. Wudl, A. J. Heeger, *Science,* 1995, 270, 1789 and having the structure shown below, or an structural analogous compound with e.g. a $C_{70}$ fullerene group ($C_{70}$PCBM), or a polymer (see for example Coakley, K. M. and McGehee, M. D. *Chem. Mater.,* 2004, 16, 4533).

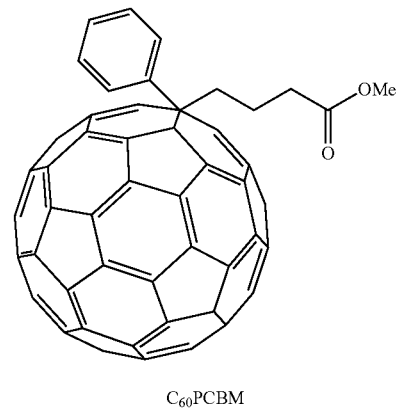

$C_{60}$PCBM

A blend or mixture of a polymer according to the present invention with a $C_{60}$ or $C_{70}$ fullerene or modified fullerene like $C_{60}$PCBM or $C_{70}$PCBM is the preferred material combination to be used in formulations for OPV devices. Preferably the ratio polymer:fullerene is from 5:1 to 1:5 by weight, more preferably from 1:1 to 1:3 by weight, most preferably 1:1 to 1:2 by weight. A polymeric binder may also be included, from 5 to 95% by weight. Examples of binder include polystyrene (PS), polypropylene (PP) and polymethylmethacrylate (PMMA).

To produce thin layers in BHJ OPV devices the oligomers, polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letterpress printing, screen printing, gravure printing, doctor blade coating, roller printing, reverse-roller printing, offset lithography printing, dry offset lithography printing, flexographic printing, web printing, spray coating, dip coating, curtain coating, brush coating, slot dye coating or pad printing. For the fabrication of OPV devices and modules area printing method compatible with flexible substrates are preferred, for example slot dye coating, spray coating and the like.

Suitable solutions or formulations containing the blend or mixture of a polymer according to the present invention with a $C_{60}$ or $C_{70}$ fullerene or modified fullerene like PCBM must be prepared. In the preparation of formulations, suitable solvent must be selected to ensure full dissolution of both component, p-type and n-type and take into account the boundary conditions (for example rheological properties) introduced by the chosen printing method.

Organic solvent are generally used for this purpose. Typical solvents can be aromatic solvents, halogenated solvents or chlorinated solvents, including chlorinated aromatic solvents. Examples include, but are not limited to chlorobenzene, 1,2-dichlorobenzene, chloroform, 1,2-dichloroethane, dichloromethane, carbon tetrachloride, toluene, cyclohexanone, ethylacetate, tetrahydrofuran, anisole, morpholine, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetraline, decaline, indane, methyl benzoate, ethyl benzoate, mesitylene and combinations thereof.

The OPV device can for example be of any type known from the literature (see e.g. Waldauf et al., *Appl. Phys. Lett.*, 2006, 89, 233517).

A first preferred OPV device according to the invention comprises the following layers (in the sequence from bottom to top):
  optionally a substrate,
  a high work function electrode, preferably comprising a metal oxide, like for example ITO, serving as anode,
  an optional conducting polymer layer or hole transport layer, preferably comprising an organic polymer or polymer blend, for example of PEDOT:PSS (poly(3,4-ethylenedioxythiophene): poly(styrene-sulfonate), or TBD (N,N'-dyphenyl-N—N'-bis(3-methylphenyl)-1,1'biphenyl-4,4'-diamine) or NBD (N,N'-dyphenyl-N—N'-bis(1-napthylphenyl)-1,1'biphenyl-4,4'-diamine),
  a layer, also referred to as "active layer", comprising a p-type and an n-type organic semiconductor, which can exist for example as a p-type/n-type bilayer or as distinct p-type and n-type layers, or as blend or p-type and n-type semiconductor, forming a BHJ,
  optionally a layer having electron transport properties, for example comprising LiF,
  a low work function electrode, preferably comprising a metal like for example aluminum, serving as cathode,
  wherein at least one of the electrodes, preferably the anode, is transparent to visible light, and
  wherein the p-type semiconductor is a polymer according to the present invention.

A second preferred OPV device according to the invention is an inverted OPV device and comprises the following layers (in the sequence from bottom to top):
  optionally a substrate,
  a high work function metal or metal oxide electrode, comprising for example ITO, serving as cathode,
  a layer having hole blocking properties, preferably comprising a metal oxide like $TiO_x$ or $Zn_x$,
  an active layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ,
  an optional conducting polymer layer or hole transport layer, preferably comprising an organic polymer or polymer blend, for example of PEDOT:PSS or TBD or NBD,
  an electrode comprising a high work function metal like for example silver, serving as anode,
  wherein at least one of the electrodes, preferably the cathode, is transparent to visible light, and
  wherein the p-type semiconductor is a polymer according to the present invention.

In the OPV devices of the present invent invention the p-type and n-type semiconductor materials are preferably selected from the materials, like the polymer/fullerene systems, as described above When the active layer is deposited on the substrate, it forms a BHJ that phase separate at nanoscale level. For discussion on nanoscale phase separation see Dennler et al, *Proceedings of the IEEE*, 2005, 93 (8), 1429 or Hoppe et al, *Adv. Func. Mater,* 2004, 14(10), 1005. An optional annealing step may be then necessary to optimize blend morphology and consequently OPV device performance.

Another method to optimize device performance is to prepare formulations for the fabrication of OPV(BHJ) devices that may include high boiling point additives to promote phase separation in the right way. 1,8-octanedithiol, 1,8-diiodooctane, nitrobenzene, chloronaphthalene, and other additives have been used to obtain high-efficiency solar cells. Examples are disclosed in J. Peet, et al, *Nat. Mater,* 2007, 6, 497 or Fréchet et al. *J. Am. Chem. Soc.,* 2010, 132, 7595-7597.

The oligomers, polymers, formulations and layers of the present invention are also suitable for use in an OFET as the semiconducting channel. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises an oligomer, polymer, polymer blend, formulation or organic semiconducting layer according to the present invention.

Other features of the OFET are well known to those skilled in the art.

OFETs where an OSC material is arranged as a thin film between a gate dielectric and a drain and a source electrode, are generally known, and are described for example in U.S. Pat. No. 5,892,244, U.S. Pat. No. 5,998,804, U.S. Pat. No. 6,723,394 and in the references cited in the background section. Due to the advantages, like low cost production using the solubility properties of the compounds according to the invention and thus the processability of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:

a source electrode,
a drain electrode,
a gate electrode,
a semiconducting layer,
one or more gate insulator layers,
optionally a substrate.
wherein the semiconductor layer preferably comprises an oligomer, polymer, polymer blend or formulation as described above and below.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetery value, like stamps, tickets, shares, cheques etc.

Alternatively, the materials according to the invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Müller et al, *Synth. Metals,* 2000, 111-112, 31-34, Alcala, *J. Appl. Phys.,* 2000, 88, 7124-7128 and the literature cited therein.

According to another use, the materials according to this invention, especially those showing photoluminescent properties, may be employed as materials of light sources, e.g. in display devices, as described in EP 0 889 350 A1 or by C. Weder et al., *Science,* 1998, 279, 835-837.

A further aspect of the invention relates to both the oxidised and reduced form of the compounds according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids (e.g., HF, HCl, $HNO_3$, $H_2SO_4$, $HClO_4$, $FSO_3H$ and $ClSO_3H$), organic acids, or amino acids, transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MOCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(NO_3)_3.6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the oligomer and polymers of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The oligomer and polymers and formulations according to the present invention may also be suitable for use in organic plasmon-emitting diodes (OPEDs), as described for example in Koller et al., *Nat. Photonics,* 2008, 2, 684.

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 2003/0021913 A1.

According to another use the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.*, 1999, 96, 12287; D. Wang, X. Gong, P. S. Heeger, F. Rininsland, G. C. Bazan and A. J. Heeger, *Proc. Natl. Acad. Sci. U.S.A.*, 2002, 99, 49; N. DiCesare, M. R. Pinot, K. S. Schanze and J. R. Lakowicz, *Langmuir*, 2002, 18, 7785; D. T. McQuade, A. E. Pullen, T. M. Swager, *Chem. Rev.*, 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

Above and below, unless stated otherwise percentages are percent by weight and temperatures are given in degrees Celsius (° C.).

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

The invention will now be described in more detail by reference to the following examples, which are illustrative only and do not limit the scope of the invention.

Example 1

2,3,7,8-Tetrabromo-4,9-dihydro-4,4,9,9-tetrahexadecyl-s-indaceno[1,2-b:5,6-b']dithiophene

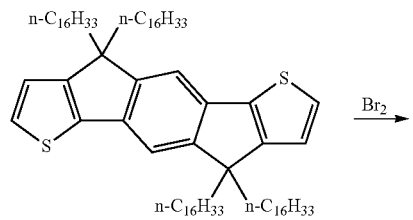

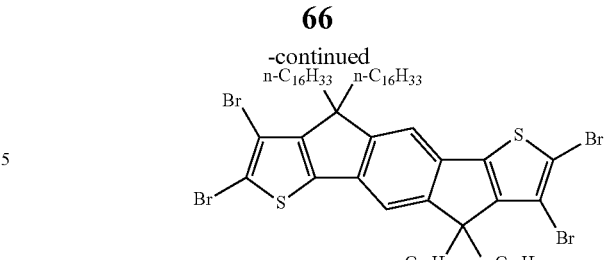

To a solution of 4,9-dihydro-4,4,9,9-tetrahexadecyl-s-indaceno[1,2-b:5,6-b']dithiophene (16.0 g, 13.7 mmol) in chloroform (1200 cm$^3$) and acetic acid (500 cm$^3$) is added slowly bromine (7.0 cm$^3$, 140 mmol). After addition, the mixture is stirred in the dark at 60° C. for 17 hours. The mixture is allowed to cool to 23° C., further bromine (2 cm$^3$, 39 mmol) added and the mixture heated at 60° C. for 4 hours. The mixture is allowed to cool to 23° C. and saturated aqueous sodium metabisulfite (500 cm$^3$) added. The product is extracted with dichloromethane (2×500 cm$^3$). The combined organics are dried over anhydrous magnesium sulfate, filtered and the solvent removed in vacuo. The crude material is passed through a silica plug (dichloromethane) and the filtrate concentrated, in vacuo, to about 600 cm$^3$ and methanol (200 cm$^3$) added. The solid is collected by filtration to give 2,3,7,8-tetrabromo-4,9-dihydro-4,4,9,9-tetrahexadecyl-s-indaceno[1,2-b:5,6-b']dithiophene (14.5 g, 71%) as a yellow solid. $^1$H-NMR (300 MHz, CDCl$_3$) 0.44-1.36 (124H, m, CH$_3$ and CH$_2$), 1.80-1.97 (4H, m, CH$_2$), 2.26-2.39 (4H, m, CH$_2$), 7.17 (2H, s, ArH).

3,8-Dibromo-4,9-dihydro-4,4,9,9-tetrahexadecyl-s-indaceno[1,2-b:5,6-b']dithiophene-2-carbaldehyde

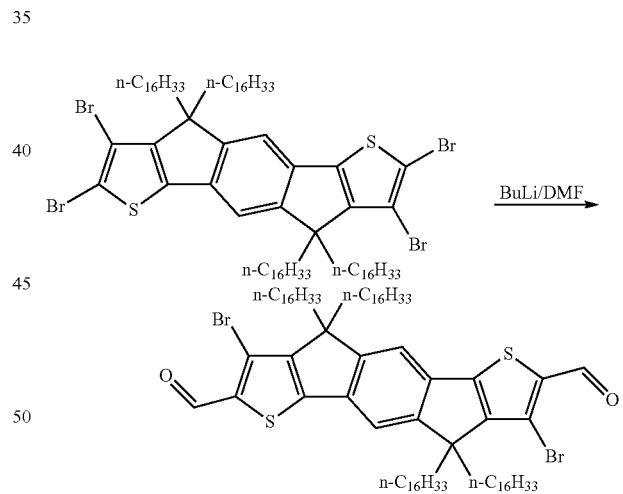

To a mixture of 2,3,7,8-tetrabromo-4,9-dihydro-4,4,9,9-tetrahexadecyl-s-indaceno[1,2-b:5,6-b']dithiophene (10.8 g, 7.3 mmol) and anhydrous tetrahydrofuran (900 cm$^3$) at 0° C. is added dropwise over 75 minutes n-butyllithium (7.3 cm$^3$, 18 mmol). After addition, the mixture is stirred at 0° C. for 30 minutes. Anhydrous N,N-dimethylformamide (3.4 cm$^3$, 44 mmol) is added all at once and the mixture allowed to warm to 23° C. over 2 hours. Water (500 cm$^3$) is added and the product extracted with dichloromethane (2×500 cm$^3$). The combined organics are dried over anhydrous magnesium sulfate, filtered and the solvent removed in vacuo. The crude is purified by column chromatography (gradient from 40-60 petrol to 1:1 40-60 petrol:dichloromethane) followed by recrystillisation (dichloromethane/methanol) to give 3,8-dibromo-4,9-dihydro-4,4,9,9-tetrahexadecyl-s-indaceno[1,2-b:5,6-b']dithiophene-2-carbaldehyde (7.32 g, 73%) as a dark yellow solid. $^1$H-NMR (300 MHz, CDCl$_3$) 0.46-1.35 (124H, m, CH$_3$ and CH$_2$), 1.89-2.07 (4H, m, CH$_2$), 2.33-2.52 (4H, m, CH$_2$), 7.43 (2H, s, ArH), 10.02 (2H, s, CHO).

5,11-Dihydro-5,5,11,11-tetrahexadecyl-dithieno[2,3-d:2',3'-d']-s-indaceno[1,2-b:5,6-b']dithiophene-2-carboxylic acid ethyl ester

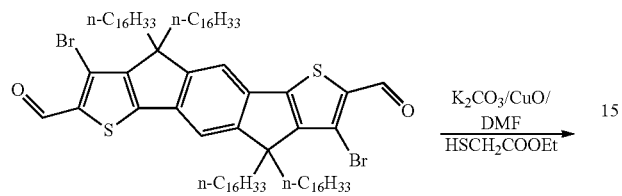

(2×500 cm$^3$). The combined organics are dried over anhydrous magnesium sulfate, filtered and the solvent removed in vacuo. The crude is purified by column chromatography (gradient from 40-60 petrol to 1:1 40-60 petrol:dichloromethane) to give 5,11-dihydro-5,5,11,11-tetrahexadecyl-dithieno[2,3-d:2',3'-d']-s-indaceno[1,2-b:5,6-b']dithiophene-2-carboxylic acid ethyl ester (3.08 g, 57%) as a yellow solid. $^1$H-NMR (300 MHz, CDCl$_3$) 0.62-1.33 (124H, m, CH$_3$ and CH$_2$), 1.42 (6H, t, CH$_3$, J 7.2), 1.93-2.20 (8H, m, CH$_2$), 4.40 (4H, q, CH$_2$, J 7.2), 7.37 (2H, s, ArH), 8.07 (2H, s, ArH).

5,11-Dihydro-5,5,11,11-tetrahexadecyl-dithieno[2,3-d:2',3'-d']-s-indaceno[1,2-b:5,6-b']dithiophene-2-carboxylic acid

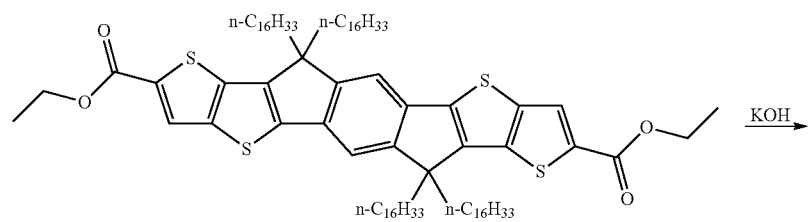

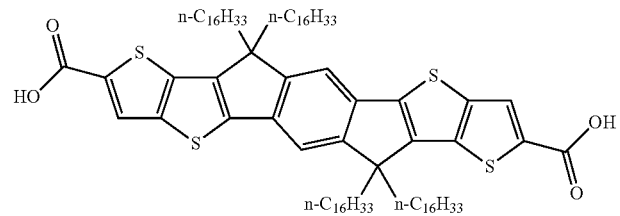

-continued

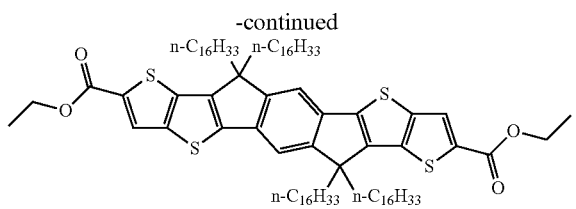

To a mixture of potassium carbonate (2.1 g, 15 mmol), 3,8-dibromo-4,9-dihydro-4,4,9,9-tetrahexadecyl-s-indaceno[1,2-b:5,6-b']dithiophene-2-carbaldehyde (5.24 g, 3.8 mmol) and anhydrous N,N-dimethylformamide (280 cm$^3$) at 60° C. is added dropwise ethylthioglycolate (0.83 cm$^3$, 7.6 mmol). After addition, the mixture is stirred at 60° C. for 17 hours. After allowing to cool to 23° C., water (500 cm$^3$) is added and the product extracted with dichloromethane A mixture of 5,11-dihydro-5,5,11,11-tetrahexadecyl-dithieno[2,3-d:2',3'-d']-s-indaceno[1,2-b:5,6-b']dithiophene-2-carboxylic acid ethyl ester (2.5 g, 1.8 mmol), potassium hydroxide (395 mg, 7 mmol), tetrabutylammonium bromide (125 mg), tetrahydrofuran (50 cm$^3$), methanol (10 cm$^3$) and water (10 cm$^3$) is heated at reflux for 17 hours. The mixture is allowed to cool to 23° C. and 5 M aqueous hydrochloric acid (300 cm$^3$) added. The organics are extracted with dichloromethane (3×200 cm$^3$) and the solvent removed in vacuo. The crude solid is washed with dichloromethane (4×100 cm$^3$) and ethyl acetate (2×50 cm$^3$) to give 5,11-dihydro-5,5,11,11-tetrahexadecyl-dithieno[2,3-d:2',3'-d']-s-indaceno[1,2-b:5,6-b']dithiophene-2-carboxylic acid (2.15 g, 90%) as a yellow solid. $^1$H-NMR (300 MHz, CDCl$_3$) 0.67-1.33 (124H, m, CH$_3$ and CH$_2$), 1.94-2.25 (8H, m, CH$_2$), 7.41 (2H, s, ArH), 8.16 (2H, s, ArH).

5,11-Dihydro-5,5,11,11-tetrahexadecyl-dithieno[2,3-d:2',3'-d']-s-indaceno[1,2-b:5,6-b']dithiophene

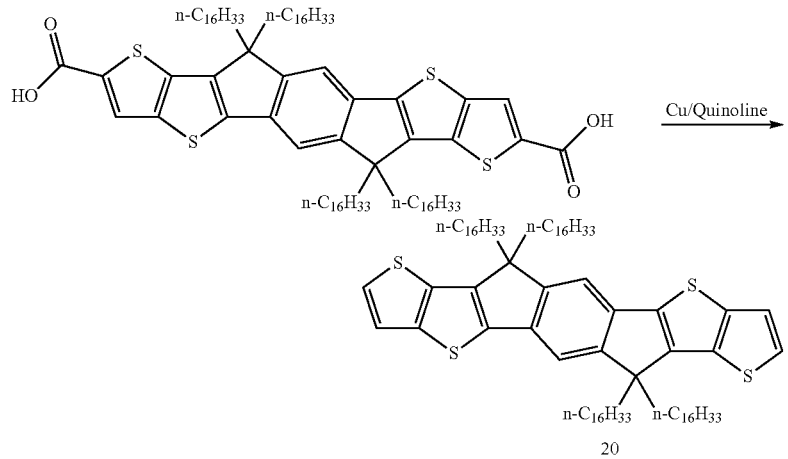

To a suspension of copper powder (80 mg, 1.3 mmol) in quinoline (40 cm$^3$) at 230° C. is added 5,11-dihydro-5,5,11,11-tetrahexadecyl-dithieno[2,3-d:2',3'-d']-s-indaceno[1,2-b:5,6-b']dithiophene-2-carboxylic acid (2.15 g, 1.6 mmol) and the mixture heated at 230° C. for 2 hours. The mixture is allowed to cool to 23° C., dichloromethane (300 cm$^3$) added and the organics washed with 1 M aqueous hydrochloric acid (3×400 cm$^3$) and water (300 cm$^3$). The organics are dried over anhydrous magnesium sulfate, filtered and the solvent removed in vacuo. The crude is filtered through a plug of silica (40-60 petrol) to give a solid which is washed with dichloromethane and methanol. Further purification by recrystallisation (dichloromethane) gives 5,11-dihydro-5,5,11,11-tetrahexadecyl-dithieno[2,3-d:2',3'-d']-s-indaceno[1,2-b:5,6-b']dithiophene (1.38, 68%) as a yellow crystalline solid. $^1$H-NMR (300 MHz, CDCl$_3$) 0.70-1.32 (124H, m, CH$_3$ and CH$_2$), 1.91-2.18 (8H, m, CH$_2$), 7.30 (2H, s, ArH), 7.32-7.34 (4H, m, ArH).

3,9-Dibromo-5,11-dihydro-5,5,11,11-tetrahexadecyl-dithieno[2,3-d:2',3'-d']-s-indaceno[1,2-b:5,6-b']dithiophene

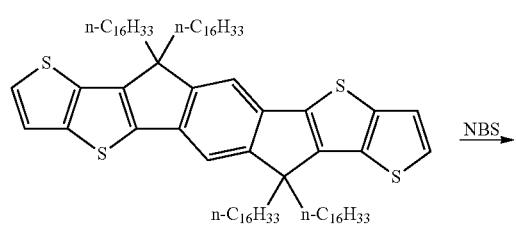

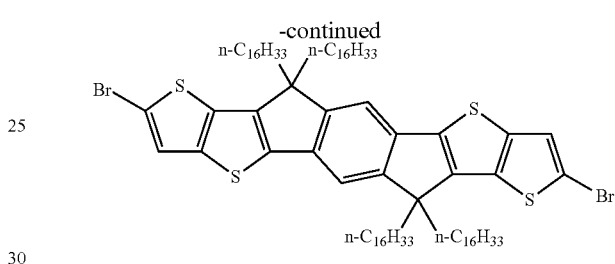

To a solution of 5,11-dihydro-5,5,11,11-tetrahexadecyl-dithieno[2,3-d:2',3'-d']-s-indaceno[1,2-b:5,6-b']dithiophene (1.34 g, 1.05 mmol) in chloroform (120 cm$^3$) and acetic acid (23 cm$^3$) is added N-bromosuccinimide (415 mg, 2.31 mmol) and the mixture stirred at 23° C., with the exclusion of light, for 5 hours. Water (300 cm$^3$) is added and the product extracted with dichloromethane (2×200 cm$^3$). The combined organics are dried over anhydrous magnesium sulfate, filtered and the solvent removed in vacuo. The crude is passed through a plug of silica (warm 40-60 petrol) followed by recrystallisation (dichloromethane/methanol) to give 3,9-dibromo-5,11-dihydro-5,5,11,11-tetrahexadecyl-dithieno[2,3-d:2',3'-d']-s-indaceno[1,2-b:5,6-b']dithiophene (1.07 g, 71%) as a yellow crystalline solid. $^1$H-NMR (300 MHz, CDCl$_3$) 0.68-1.36 (124H, m, CH$_3$ and CH$_2$), 1.87-2.12 (8H, m, CH$_2$), 7.28 (2H, s, ArH), 7.33 (2H, s, ArH).

Poly{3,9-[5,11-dihydro-5,5,11,11-tetrahexadecyl-dithieno[2,3-d:2',3'-d']-s-indaceno[1,2-b:5,6-b']dithiophene]-alt-[2,5-thieno[3,2-b]thiophene]} (Polymer 1)

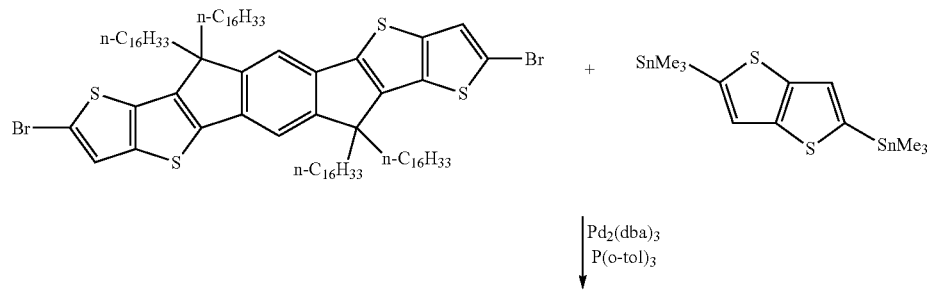

-continued

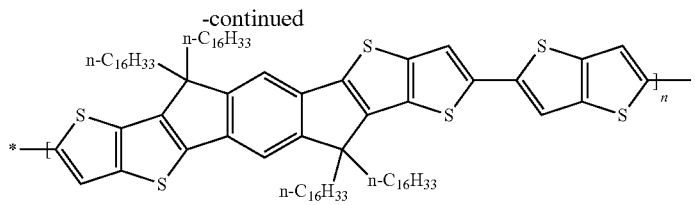

Nitrogen gas is bubbled through a mixture of 3,9-dibromo-5,11-dihydro-5,5,11,11-tetrahexadecyl-dithieno[2,3-d:2',3'-d']-s-indaceno[1,2-b:5,6-b']dithiophene (717.0 mg, 0.500 mmol), 2,5-bis-trimethylstannanyl-thieno[3,2-b]thiophene (232.9 mg, 0.500 mmol), tris(dibenzylideneacetone)dipalladium(0) (5.4 mg, 0.008 mmol), tri-o-tolyl-phosphine (11.7 mg, 0.04 mmol), anhydrous toluene (8 cm$^3$) and anhydrous N,N-dimethylformamide (2 cm$^3$) for one hour. The reaction mixture is then heated in a pre-heated oil bath at 110° C. for 30 minutes before further toluene (8 cm$^3$) is added. Bromobenzene (0.05 cm$^3$) is added and the mixture heated at 110° C. for 20 minutes. Tributyl-phenyl-stannane (0.20 cm$^3$) is then added and the mixture heated at 110° C. for 20 minutes. The mixture allowed to cool slightly and poured into stirred methanol (100 cm$^3$) and the polymer precipitate collected by filtration. The crude polymer is subjected to sequential Soxhlet extraction; acetone, cyclohexane and chloroform. The chloroform extract is poured into methanol (400 cm$^3$) and the polymer precipitate collected by filtration to give poly{3,9-[5,11-dihydro-5,5,11,11-tetrahexadecyl-dithieno[2,3-d:2',3'-d']-s-indaceno[1,2-b:5,6-b']dithiophene]-alt-[2,5-thieno[3,2-b]thlophene]} (600 mg, 85%) as a red solid. GPC (trichlorobenzene, 140° C.) $M_n$=253,000 g/mol, $M_w$=936,000 g/mol.

Example 2

Transistor Fabrication and Measurement

Top-gate thin-film organic field-effect transistors (OFETs) were fabricated on glass substrates with photolithographically defined Au source-drain electrodes. A 7 mg/cm$^3$ solution of the organic semiconductor in dichlorobenzene was spin-coated on top (an optional annealing of the film is carried out at 100° C., 150° C. or 200° C. for between 1 and 5 minutes) followed by a spin-coated fluoropolymer dielectric material (Lisicon® D139 from Merck, Germany). Finally a photolithographically defined Au gate electrode was deposited. The electrical characterization of the transistor devices was carried out in ambient air atmosphere using computer controlled Agilent 4155C Semiconductor Parameter Analyser. Charge carrier mobility in the saturation regime ($u_{sat}$) was calculated for the compound. Field-effect mobility was calculated in the saturation regime ($V_d$>($V_g$−$V_0$)) using equation (1):

$$\left(\frac{dI_d^{sat}}{dV_g}\right)_{V_d} = \frac{WC_i}{L}\mu^{sat}(V_g - V_0) \quad (1)$$

where W is the channel width, L the channel length, $C_i$ the capacitance of insulating layer, $V_g$ the gate voltage, $V_0$ the turn-on voltage, and $\mu_{sat}$ is the charge carrier mobility in the saturation regime. Turn-on voltage ($V_0$) was determined as the onset of source-drain current.

The mobility ($\mu_{sat}$) for polymer 1 in a top-gate OFET is 0.13 cm$^2$/Vs.

FIG. 1 shows the transfer characteristics and the charge carrier mobility of a top-gate OFET prepared as described above, wherein polymer 1 is used as the organic semiconductor.

The invention claimed is:

1. An oligomer or polymer comprising one or more divalent units of formula I

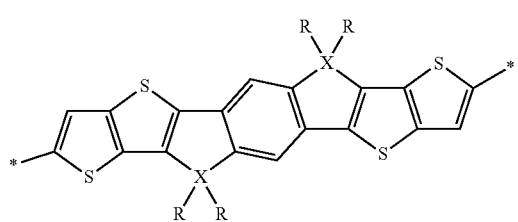

wherein R is, on each occurrence identically or differently, straight-chain or branched alkyl having 1 to 20 C atoms,
and X is on each occurrence identically or differently is Si or Ge.

2. The polymer according to claim 1, according to formula IV:

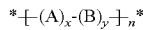

wherein
A is a unit of formula I or Formula II

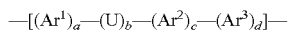

wherein
U is a unit of formula I,
Ar$^1$, Ar$^2$, Ar$^3$ are, on each occurrence identically or differently, and independently of each other, aryl or heteroaryl that is different from U, and is optionally substituted, by one or more groups R$^S$,
R$^S$ is on each occurrence identically or differently F, Br, Cl, —CN, —NC, —NCO, —NCS, —OCN, —SCN, —C(O)NR$^0$R$^{00}$, —C(O)X$^0$, —C(O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl or hydrocarbyl with 1 to 40 C atoms that is optionally substituted and optionally comprises one or more hetero atoms, or P-Sp-,
R$^0$ and R$^{00}$ are independently of each other H or optionally substituted C$_{1-40}$ hydrocarbyl,
P is a polymerisable or crosslinkable group,
Sp is a spacer group or a single bond,
X$^0$ is halogen,
a, b, c are on each occurrence identically or differently 0, 1 or 2, d is on each occurrence identically or differently 0 or an integer from 1 to 10, B is a unit that is different from A and comprises one or more aryl or heteroaryl groups that are optionally substituted, x is >0 and ≤1, y is ≥0 and <1, x+y is 1, and n is an integer>1.

3. The polymer according to claim 1, comprising a divalent unit that is selected from the following formulae

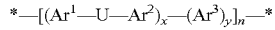    IVa

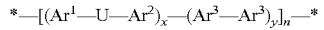    IVb

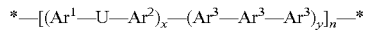    IVc

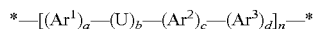    IVd

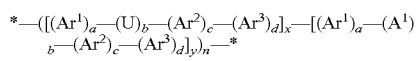    IVe wherein U, is a unit or formula I, and $Ar^1$, $Ar^2$, $Ar^3$ are, on each occurance identically or differently, and independently of each other, aryl or heteroaryl that is different from U, is optionally substituted, by one or more groups $R^S$, $R^0$ and $R^{00}$ are independently of each other H or optionally substituted $C_{1-40}$ hydrocarbyl, P is a polymerisable or crosslinkable group, Sp is a spacer group or a single bond, $X^0$ is halogen, a, b, c are on each occurrence identically or differently 0, 1 or 2, d is on each occurence identically or different 0 or an integer from 1 to 10, $A^1$ is on each occurrence identically or differently, an aryl or heteroaryl group that is different from U and $Ar^{1-3}$, has 5 to 30 ring atoms, is optionally substituted by one or more groups $R^S$ which is on each occurence identically or differently F, Br, Cl, -CN, -NC, -NCO, -NCS, -OCN, -SCN, -C(O)$NR^0R^{00}$, -C(O)$X^0$, -C(O)$R^0$, -$NH_2$, -$NR^0R^{00}$, SH, -$SR^0$, -$SO_3H$, -$SO_2R^0$, -OH, -$NO_2$, -$CF_3$, -$SF_5$, optionally substituted silyl or hydrocarbyl with 1 to 40 C atoms that is optionally substituted and optionally comprises one or more hetero atoms, or P-Sp-, and is selected from aryl or heteroaryl groups having electron donor properties, and x is >0 and ≤1, y is ≥0 and <1, x+y is 1, and n is an integer >1, wherein these polymers can be alternating or random copolymers, and wherein formula IVd and IVe in at least one of the repeating units $[(Ar^1)_a—(U)_b—(Ar^2)_c—(Ar^3)_d]$ and in at least one of the repeating units $[(Ar^1)_a—(A^1)_b—(Ar^2)_c—(Ar^3)_d]$ b is at least 1.

4. An oligomer of formula VII

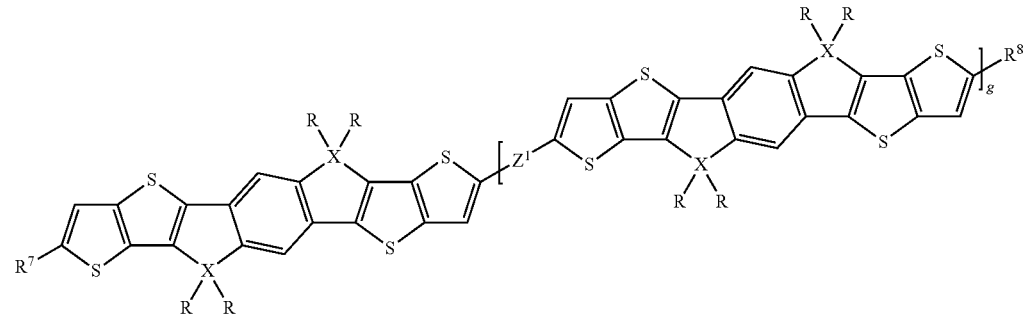    VII wherein,

R is, on each occurrence identically or differently, straight-chain or branched alkyl having 1 to 20 C atoms, and X is on each occurrence identically or differently is Si or Ge $Z^1$ denotes a single bond, $(CY^1=CY^2)_h$, $(C≡C)_h$, wherein h=1 or 2, or $Ar^5$, $Y^1$ and $Y^2$ are independently of each other H, F, Cl or CN and $Ar^5$ is aryl or heteroaryl that is different from Formula I, has 5 to 30 ring atoms and is optionally substituted, $R^7$ and $R^8$ independently of each other denote H, F, Br, Cl, -CN, -NC, -NCO, -NCS, -OCN, -SCN, -C(O)$NR^0R^{00}$, -C(O)$X^0$, -C(O)$R^0$, -C(O)$OR^0$, -O-C(O)$R^0$, -$NH_2$, -$NR^0R^{00}$, -SH, -$SR^0$, -$SH_3H$, -$SO_2R^0$, -OH, -$NO_2$, -$CF_3$, -$SF_5$, P-Sp-, or optionally substituted silyl or hydrocarbyl with 1 to 40 C atoms that is optionally substituted and optionally comprises one or more hetero atoms, and wherein one or more C atoms are optionally replaced by a hetero atom, and R and $R^{00}$ are independently of each other H or optionally substituted $C_{140}$ hydrocarbyl, and $X^0$ is halogen, and g is 1, 2 or 3, P is a polymerisable or crosslinkable group, Sp is a spacer group or a single bond.

5. A polymer according to claim 1, of formula V $R^5$-chain-$R^6$    V wherein "chain" is a polymer chain selected from formulas IV, IVa-IVe and IV1-IV5

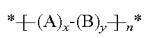    IV

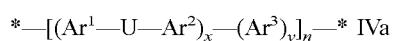    IVa

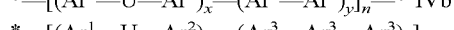    IVb

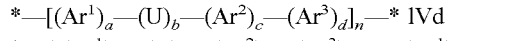    IVC

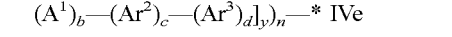    IVd

    IVe

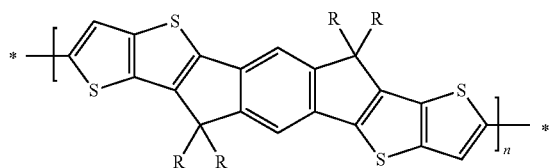

IV2

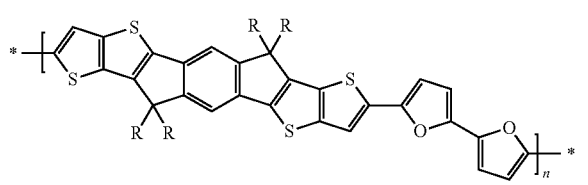

IV3

A is a unit of Formula I or Formula II

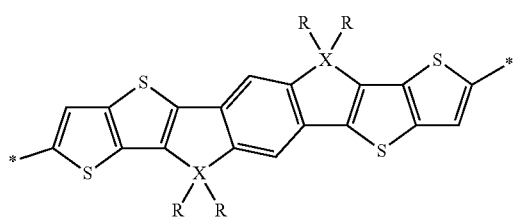

I

I wherein R is, on each occurrence identically or differently, straight-chain or branched alkyl having 1 to 20 C atoms, and X is on each occurrence identically or differently is Si or Ge —[(Ar¹)ₐ—(U)ᵦ—(Ar²)꜀—(Ar³)ᵈ]—II U is a unit of formula I, Ar¹, Ar², Ar³ are, on each occurrence identically or differently, and independently of each other, aryl or heteroaryl that is different from U, is optionally substituted, by one or more groups $R^S$, $R^S$ is on each occurrence identically or differently F, Br, Cl, -CN, -NC, -NCO, -NCS, -OCN, -SCN, -C(O)NR°R°°, -C(O)X°, -C(O)R°, -NH₂, -NR°R°°, -SH, -SR°, -SO₃H, -SO₂R°, -OH, -NO₂, -CF₃, -SF₅, optionally substituted silyl or hydrocarbyl with 1 to 40 C atoms that is optionally substituted and optionally comprises one or more hetero atoms, or P-Sp-, R° and R°° are independently of each other H or optionally substituted $C_{1-40}$ hydrocarbyl, P is a polymerisable or crosslinkable group, Sp is a spacer group or a single bond, X° is halogen, a, b, c are on each occurrence identically or differently 0, 1 or 2, d is on each occurrence identically or differently 0 or an integer from 1 to 10, B is a unit that is different from A and comprises one or more aryl or heteroaryl groups that are optionally substituted, x is >0 and ≤1, y is ≥0 and <1, x+y is 1, and n is an integer >1

A¹ is on each occurrence identically or differently an aryl or heteroaryl group that is different from U and Ar¹⁻³, has 5 to 30 ring atoms, is optionally substituted by one or more groups $R^S$ and is selected from aryl or heteroaryl groups having electron donor properties, wherein in formula IVd and IVe in at least one of the repeating units [(Ar¹)ₐ—(U)ᵦ—(Ar²)꜀—(Ar³)ᵈ] and in at least one of the repeating units [(Ar¹)ₐ—(A¹)ᵦ—(Ar²)꜀—(Ar³)ᵈ] b is at least 1, R is, on each occurrence identically or differently, straight-chain or branched alkyl having 1 to 20 C atoms and R' is on each occurrence identically or differently F, Br, Cl, -CN, -NC, -NCO, -NCS, -OCN, -SCN, -C(O)NR°R°°, -C(O)X°, -C(O)R°, -NH₂, -NR°R°°, -SH, -SR°, -SO₃H, -SO₂R°, -OH, -NO₂, -CF₃, -SF₅, optionally substituted silyl or hydrocarbyl with 1 to 40 C atoms that is optionally substituted and optionally comprises one or more hetero atoms, or P-Spand $R^5$ and $R^6$ denote independently of each other F, Br, Cl, H, -CH₂Cl, -CHO, -CH=CH₂, -SiR'R''R''', -SnR'R''R''', -BR'R'', -B(OR')(OR''), -B(OH)₂, -ZnCl, -MgCl, -MgBr or P-Sp-, R', R'' and R''' have independently of each other one of the meanings of R°, and two of R', R'' and R''' may also form a ring together with the hetero atom to which they are attached.

6. The polymer according to claim 5, wherein one or more of Ar¹, Ar² and Ar³ denote aryl or heteroaryl selected from the group consisting of the following formulae

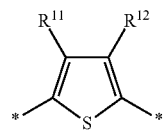

(D1)

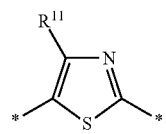

(D2)

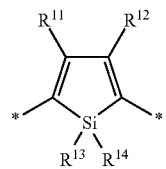

(D3)

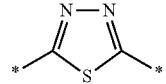

(D4)

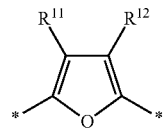

(D5)

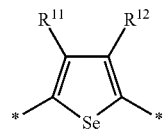

(D6)

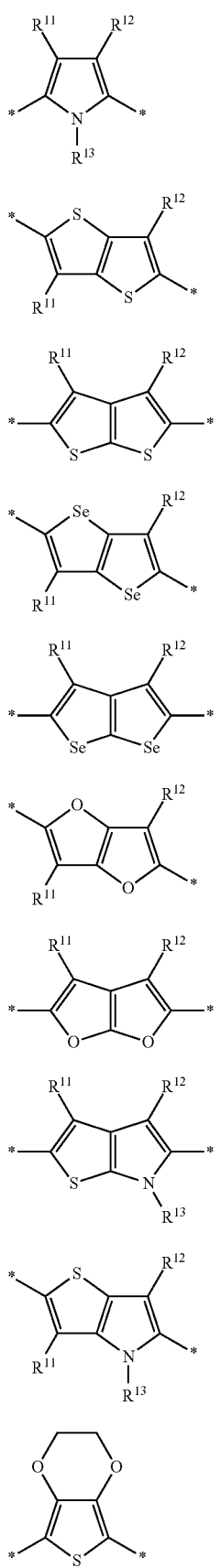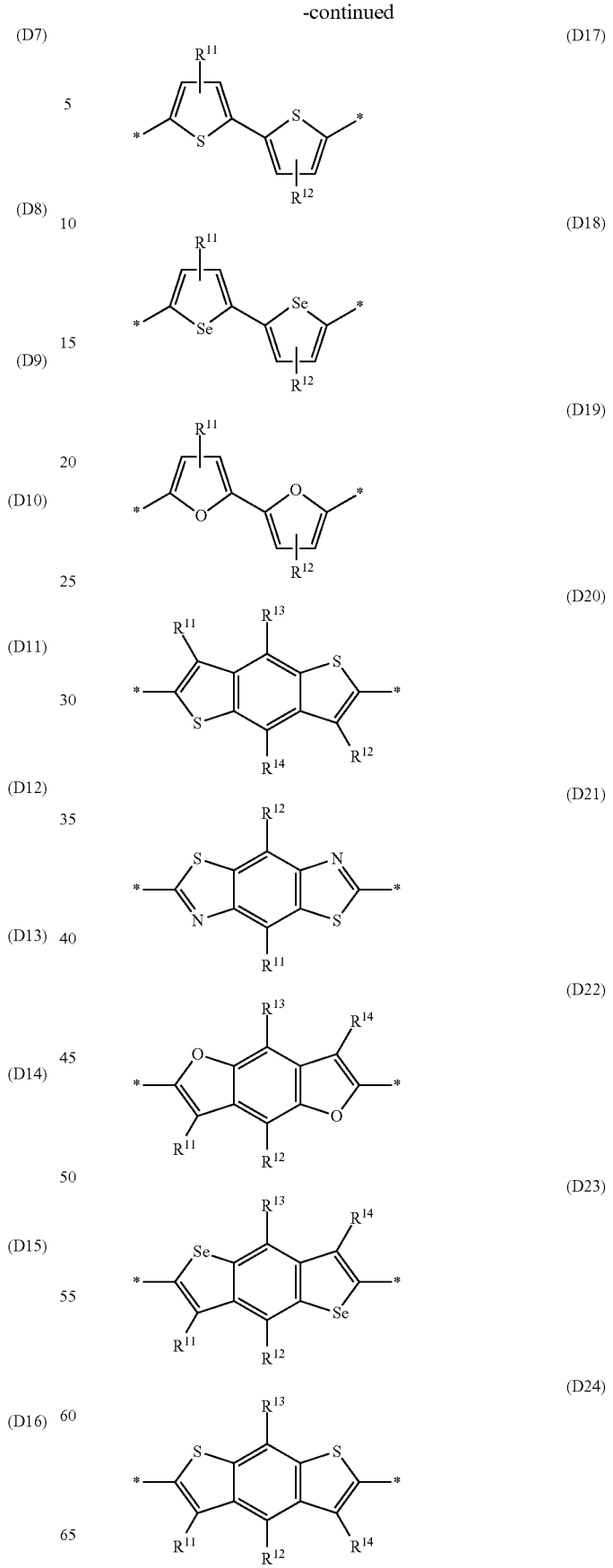

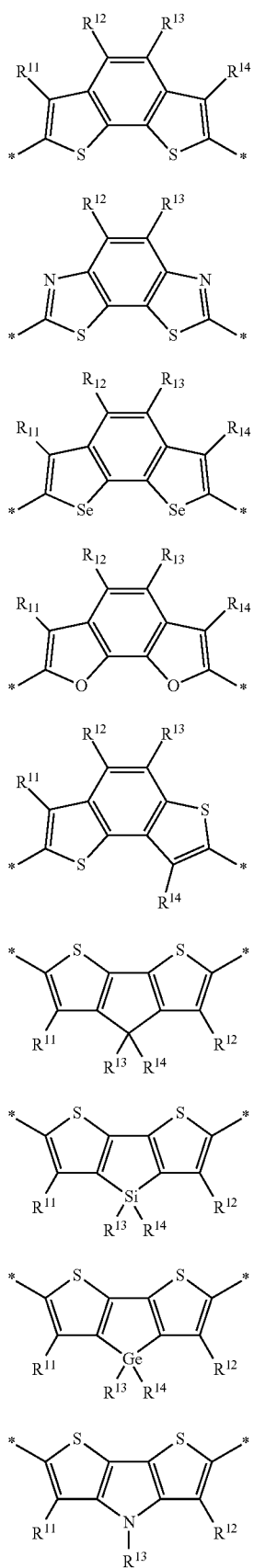
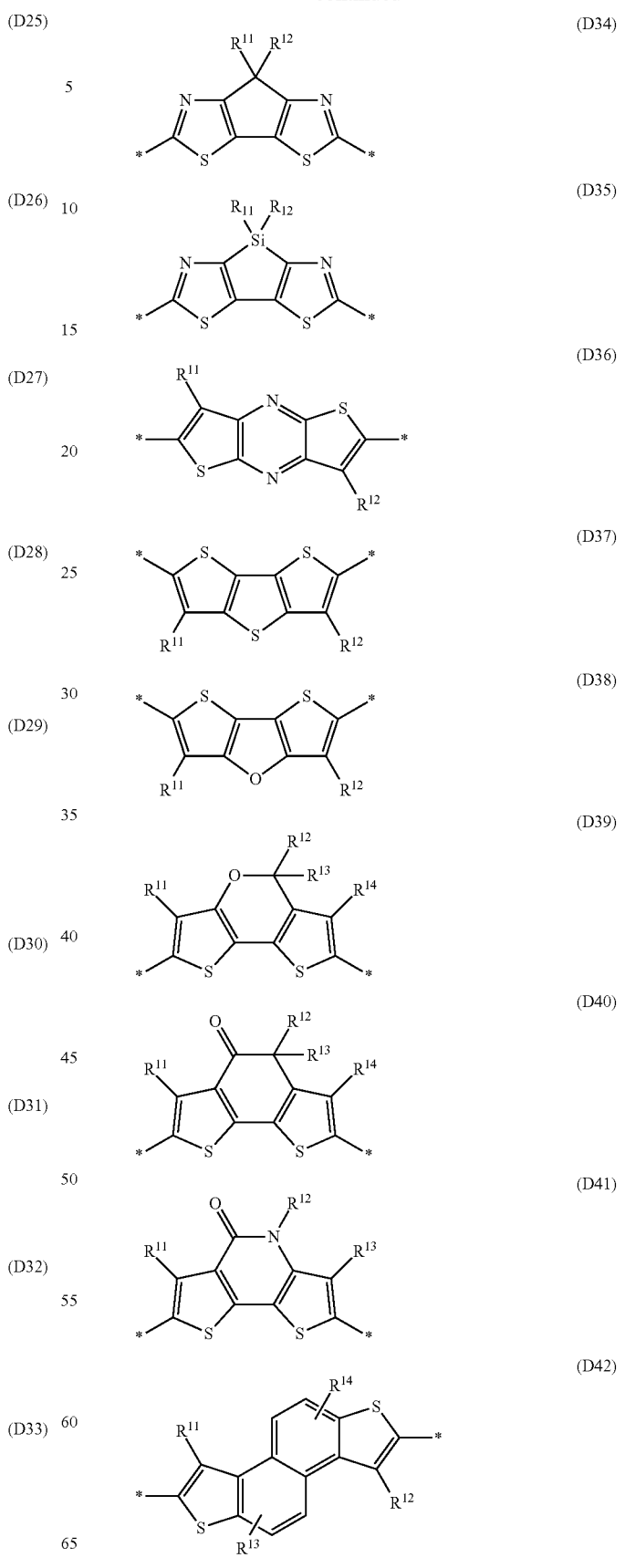

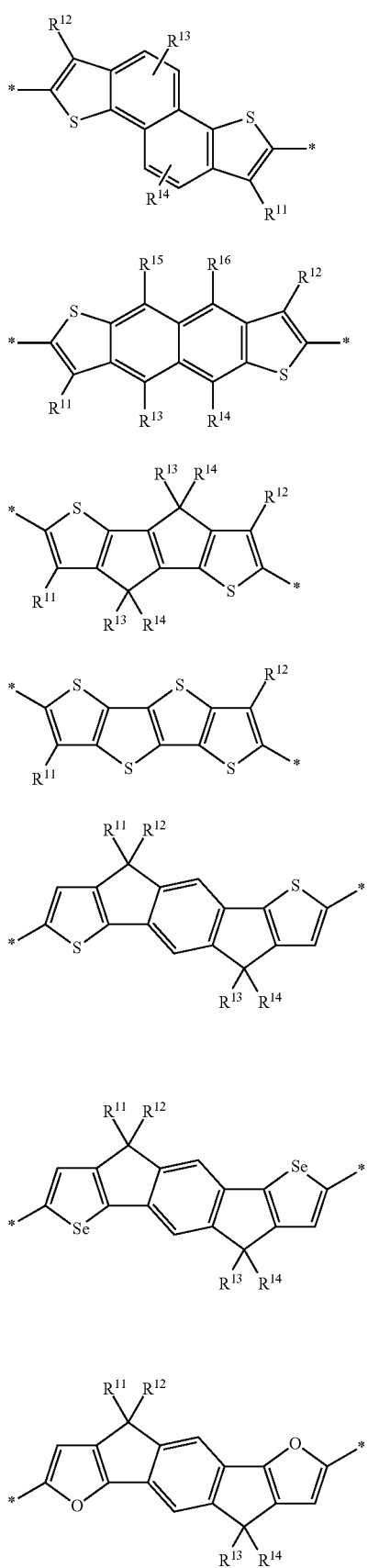
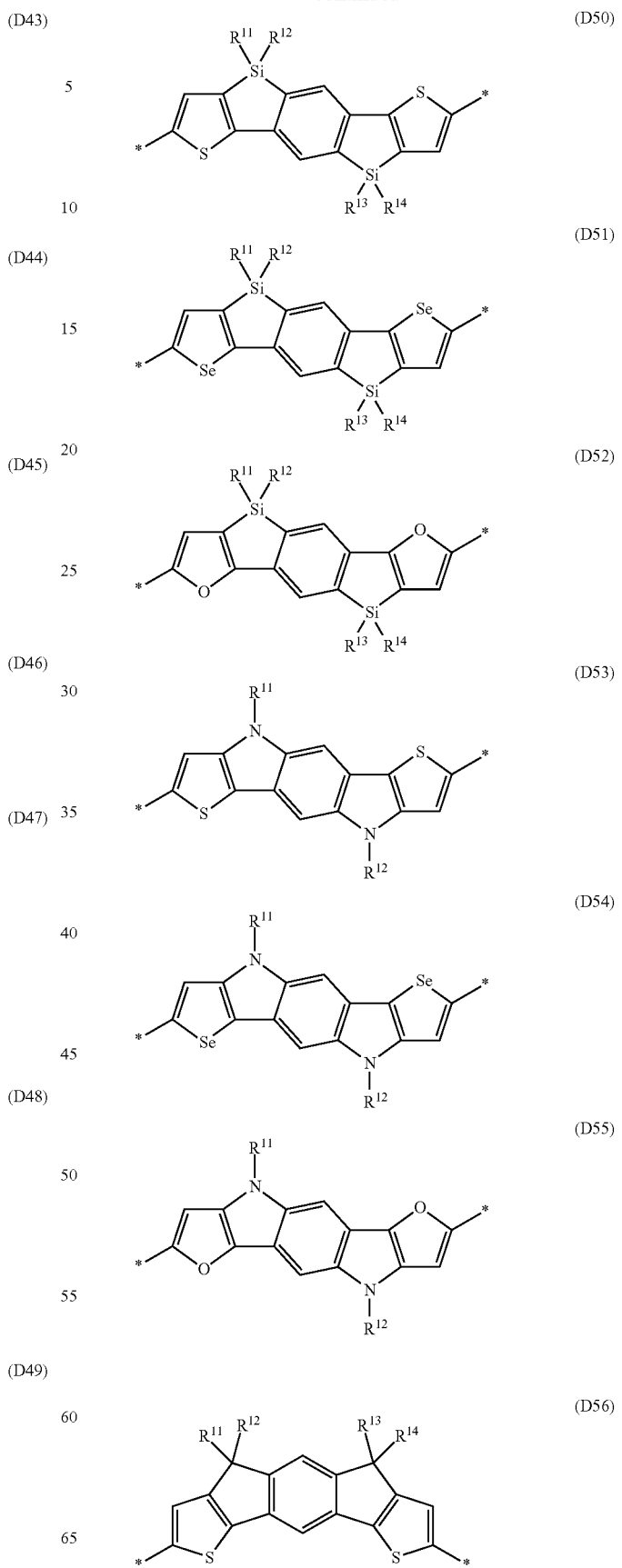

(D57) 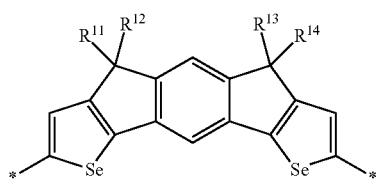
(D58) 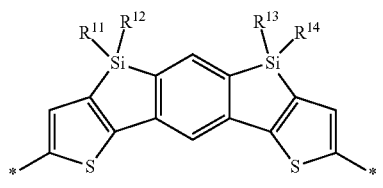
(D59) 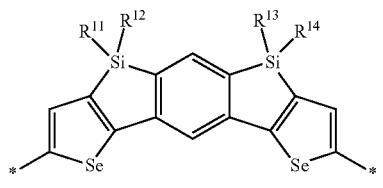
(D60) 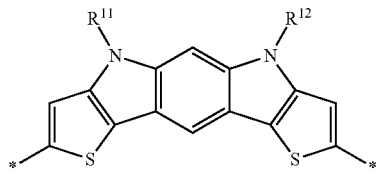
(D61) 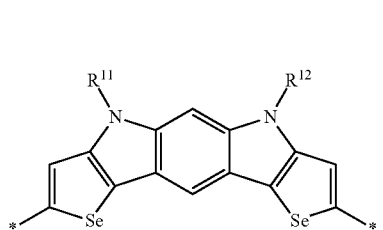
(D62) 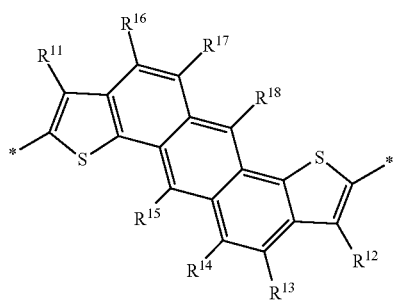
(D63) 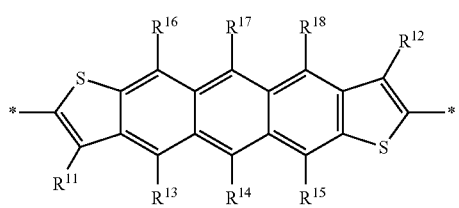
(D64) 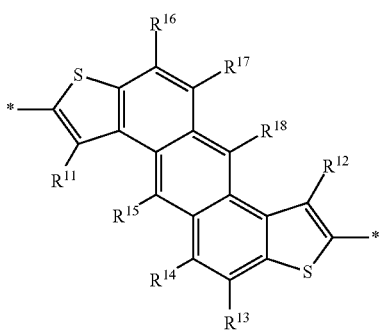
(D65) 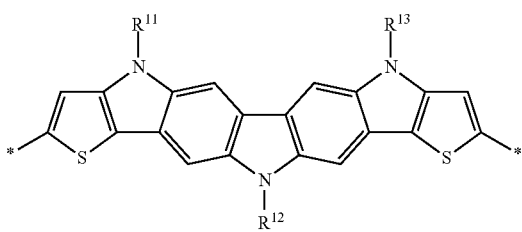
(D66) 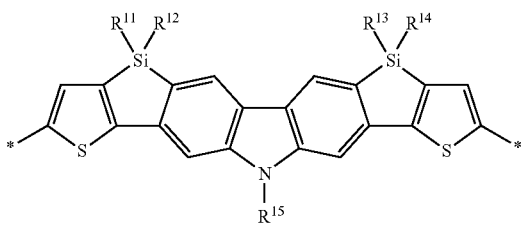
(D67) 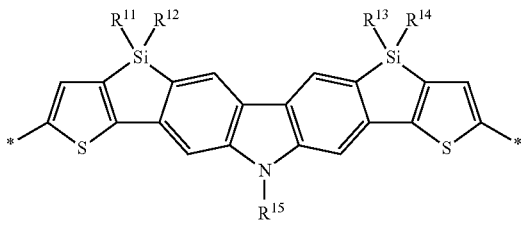
(D68) 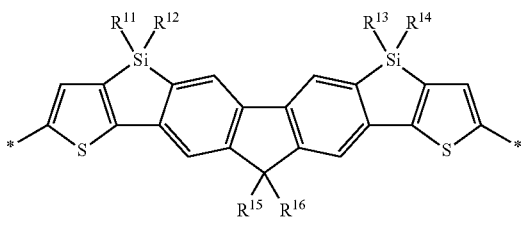
(D69) 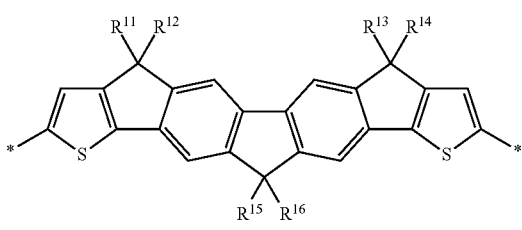

(D70)
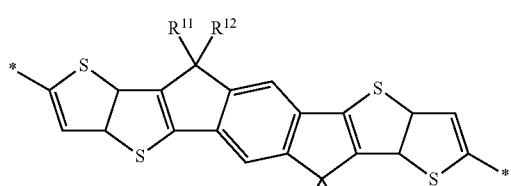
(D71)
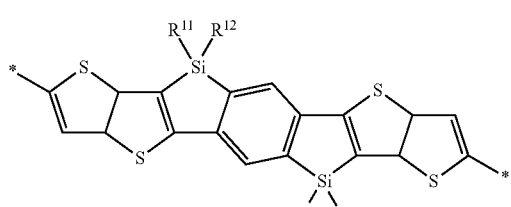
(D72)
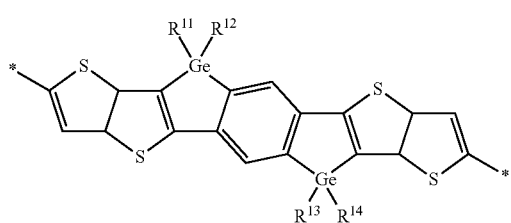
(D73)
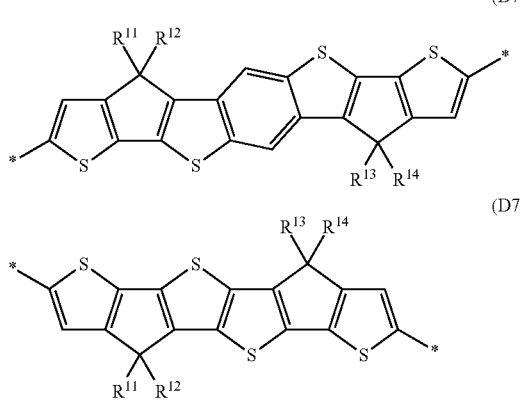
(D74)
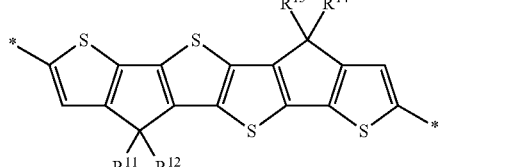
(D75)
(D76)
(D77)
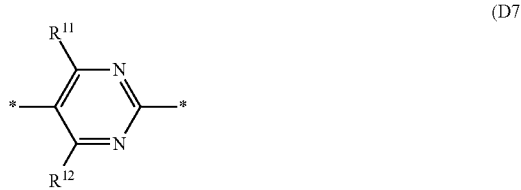
(D78)
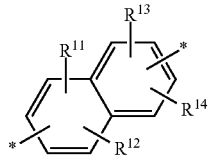
(D79)
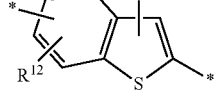
(D80)
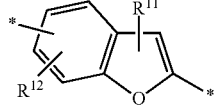
(D81)
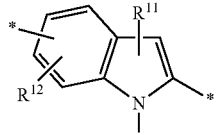
(D82)
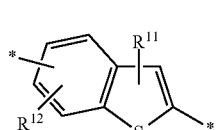
(D83)
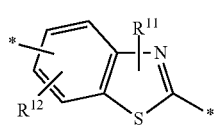
(D84)
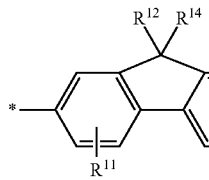
(D85)
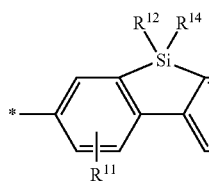
(D86)
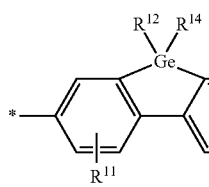
(D87)
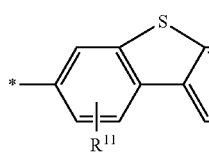

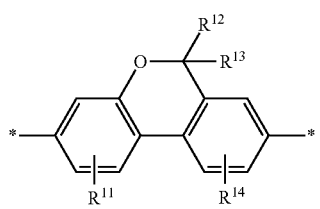
(D88)
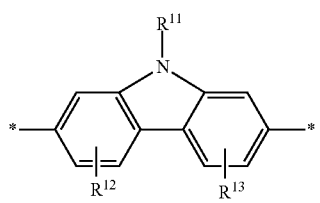
(D89)
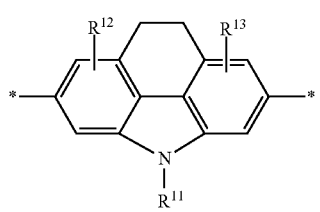
(D90)
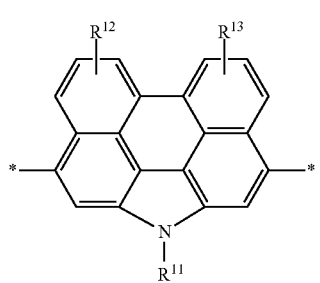
(D91)
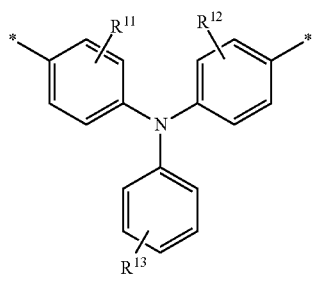
(D92)
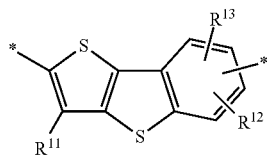
(D93)
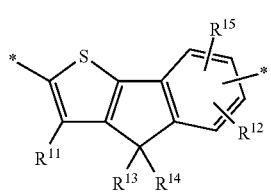
(D94)
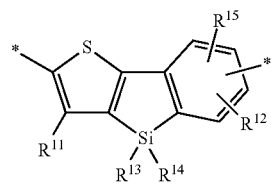
(D95)
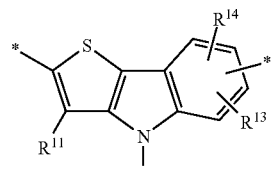
(D96)
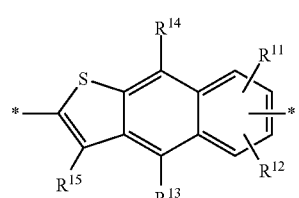
(D97)
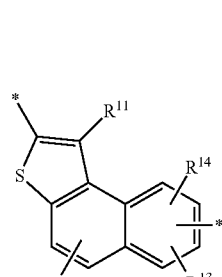
(D98)
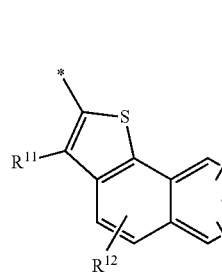
(D99)
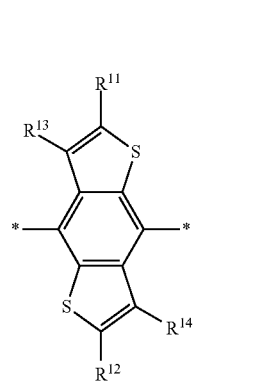
(D100)

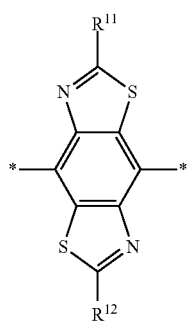
(D101)
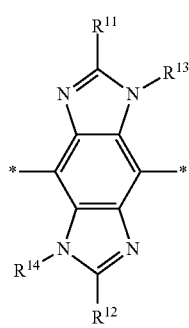
(D102)
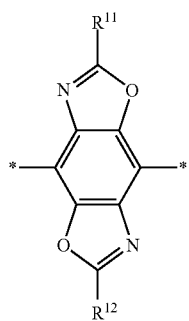
(D103)
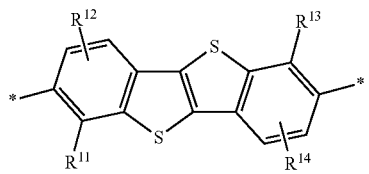
(D104)
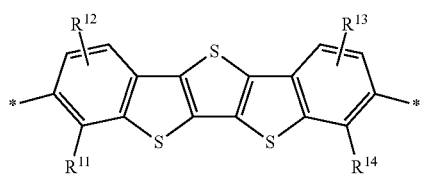
(D105)
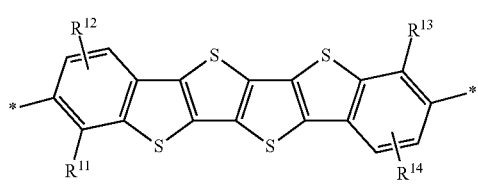
(D106)
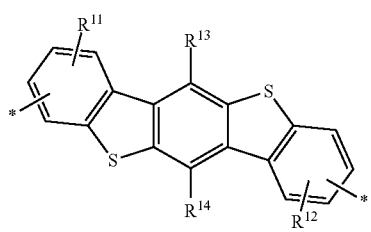
(D107)
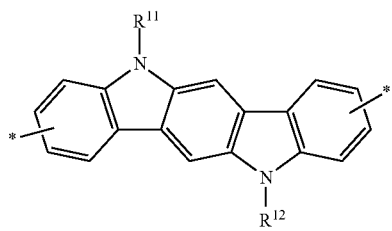
(D108)
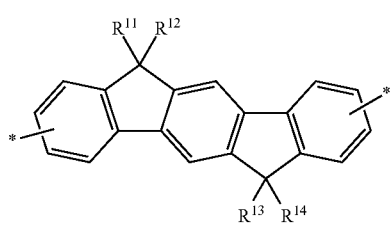
(D109)
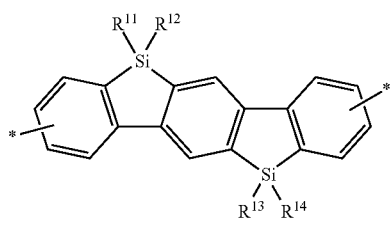
(D110)
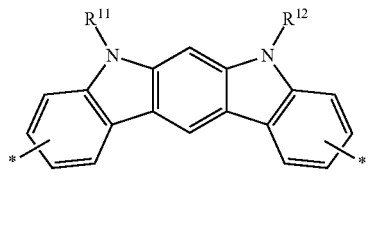
(D111)
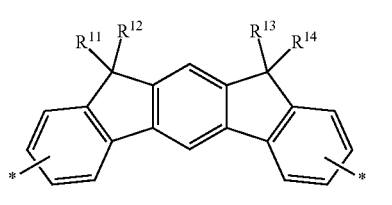
(D112)
(D113)

-continued (D114)
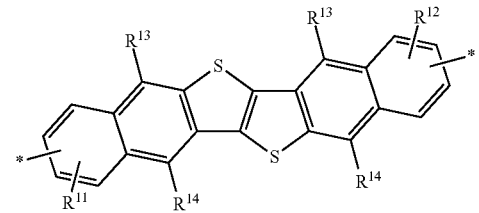

(D115)
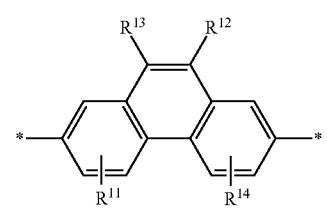

(D116)
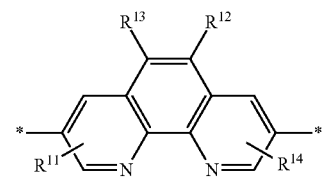

(D117)
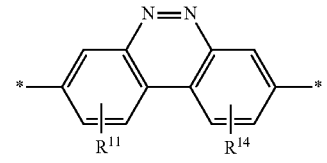

(D118)
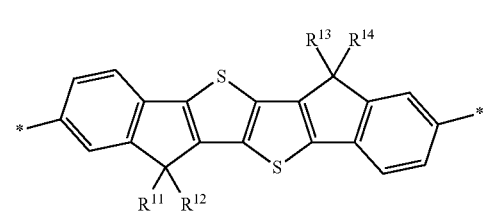

(D119)
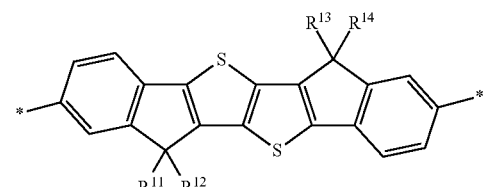

(D120)
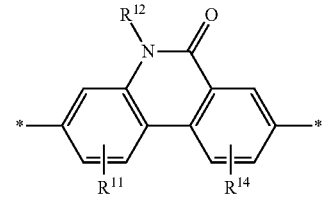

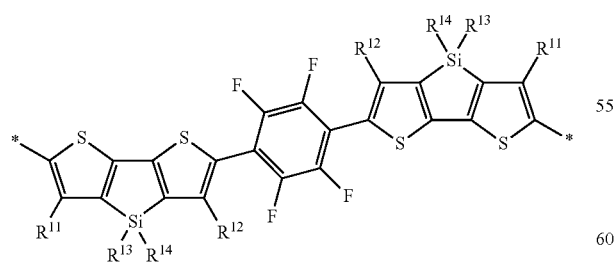

wherein $R^{11}$, $R^{12}$, $R^{13}$, $R^{14}$, $R^{15}$, $R^{16}$, $R^{17}$ and $R^{18}$ independently of each other denote H or on each occurrence identically or differently F, Br, Cl, -CN, -NC, -NCO, -NCS, -OCN, -SCN, -C(O)NR°R°°, -C(O)X°, -C(O)R°, -NH$_2$, -NR°R°°, -SH, -SR°, -SO$_3$H, -SO$_2$R°, -OH, -NO$_2$, -CF$_3$, -SF$_5$, optionally substituted silyl or hydrocarbyl with 1 to 40 C atoms that is optionally substituted and optionally comprises one or more hetero atoms, or P-Sp-, R° and R°° are independently of each other H or optionally substituted $C_{1-40}$ hydrocarbyl, P is a polymerisable or crosslinkable group, Sp is a spacer group or a single bond, X° is halogen.

7. The polymer according to claim 5, wherein one or more of the units $Ar^3$ and $A^1$ denote aryl or heteroaryl selected from the group consisting of the following formulae (A1)
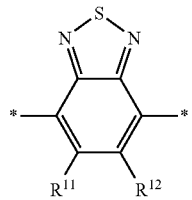

(A2)
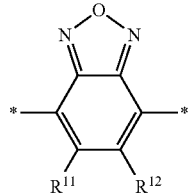

(A3)
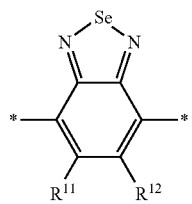

(A4)
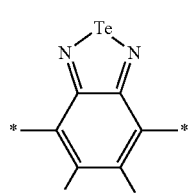

(A5)
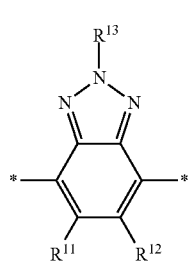

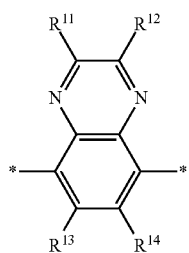 (A6)
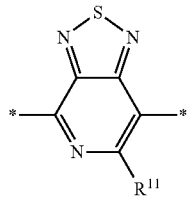 (A7)
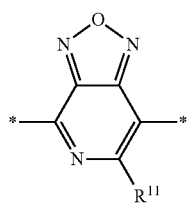 (A8)
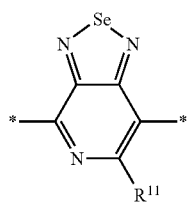 (A9)
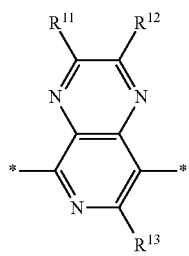 (A10)
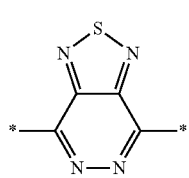 (A11)
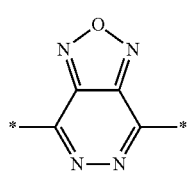 (A12)
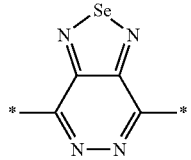 (A13)
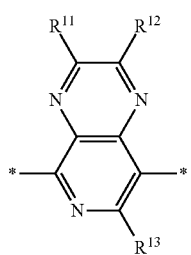 (A14)
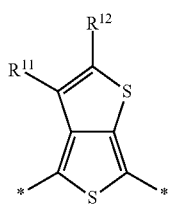 (A15)
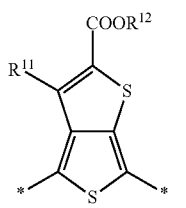 (A16)
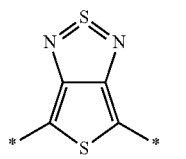 (A17)
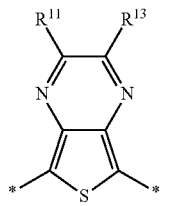 (A18)
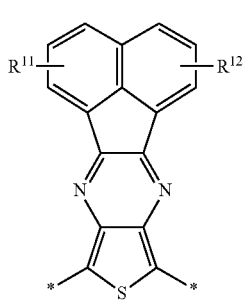 (A19)

95
-continued
(A20)
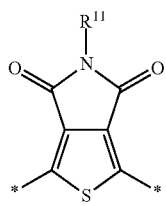
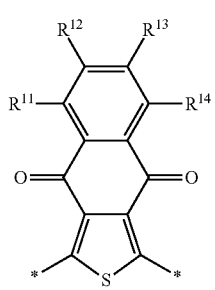
(A21)
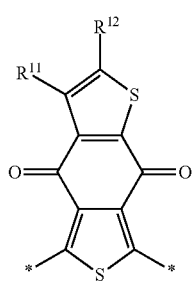
(A22)
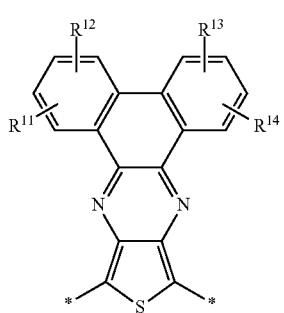
(A23)
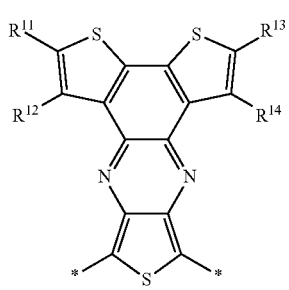
(A24)
96
-continued
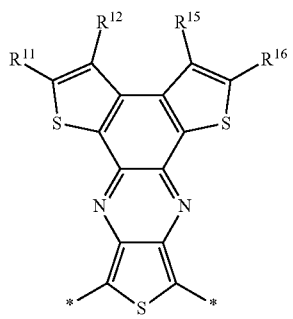
(A25)
(A26)
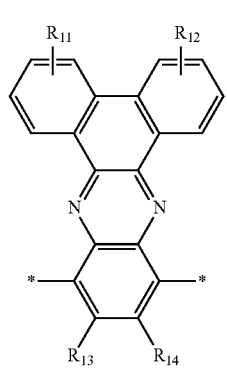
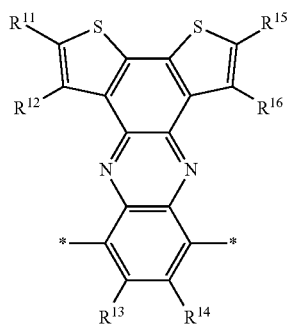
(A27)
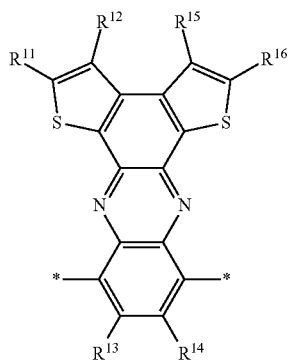
(A28)
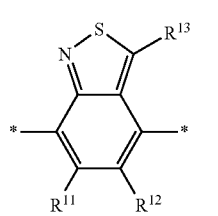
(A29)

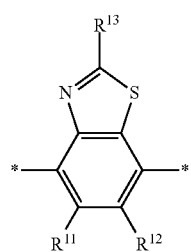 (A30)
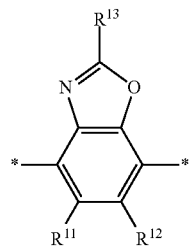 (A31)
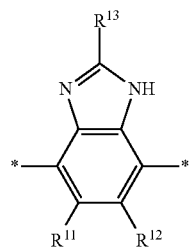 (A32)
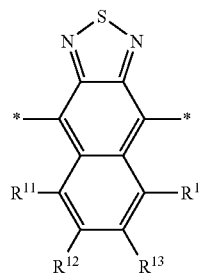 (A33)
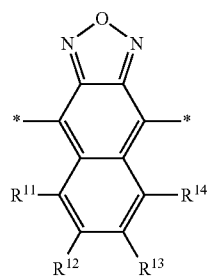 (A34)
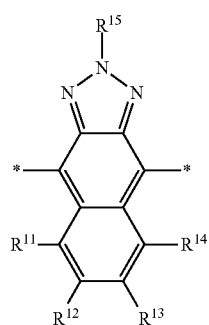 (A35)
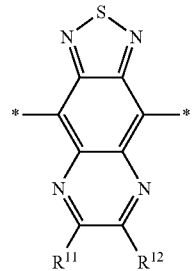 (A36)
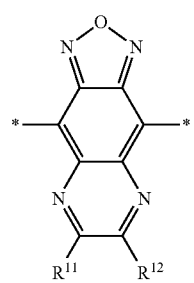 (A37)
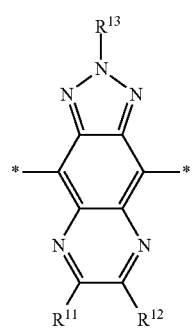 (A38)
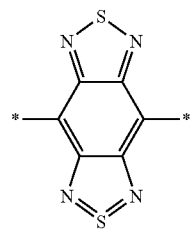 (A39)
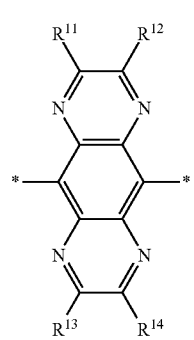 (A40)
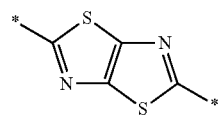 (A41)

-continued
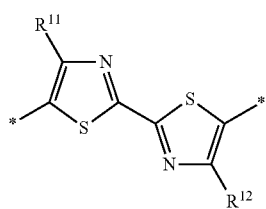
(A42)
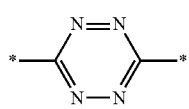
(A43)
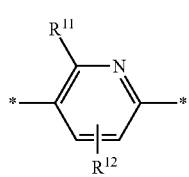
(A44)
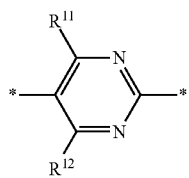
(A45)
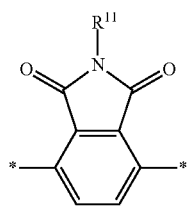
(A46)
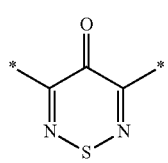
(A47)
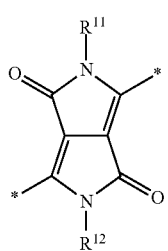
(A48)
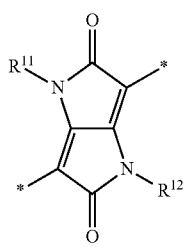
(A49)
-continued
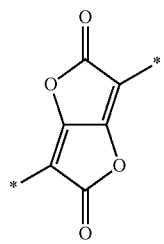
(A50)
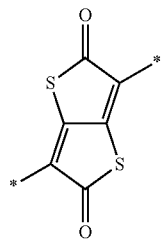
(A51)
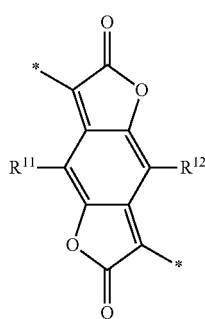
(A52)
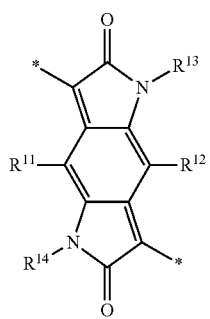
(A53)
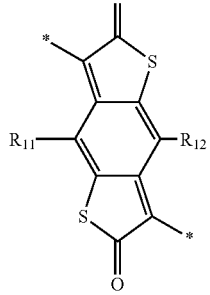
(A54)

-continued
(A55) 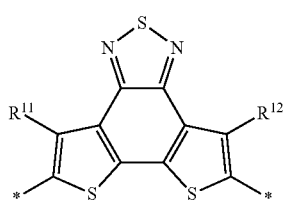
(A56) 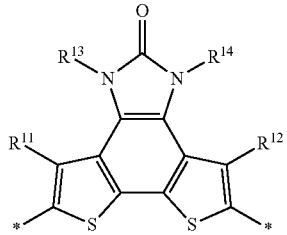
(A57) 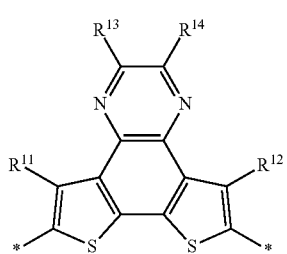
(A58) 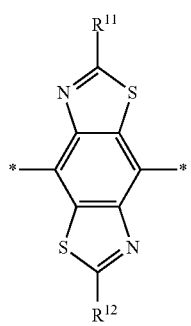
(A59) 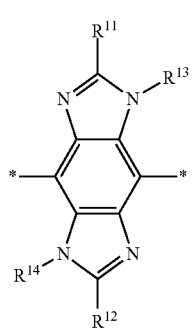
-continued
(A60) 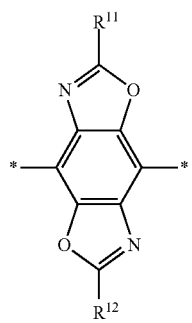
(A61) 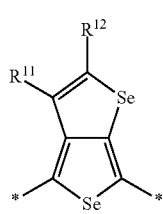
(A62) 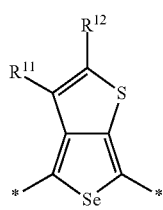
(A63) 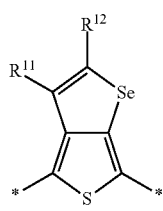
(A64) 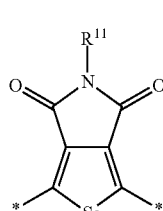
(A65) 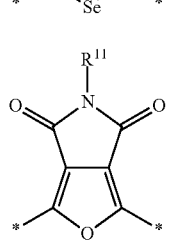
(A66) 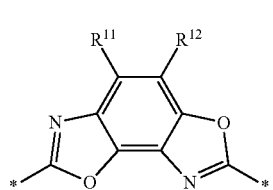

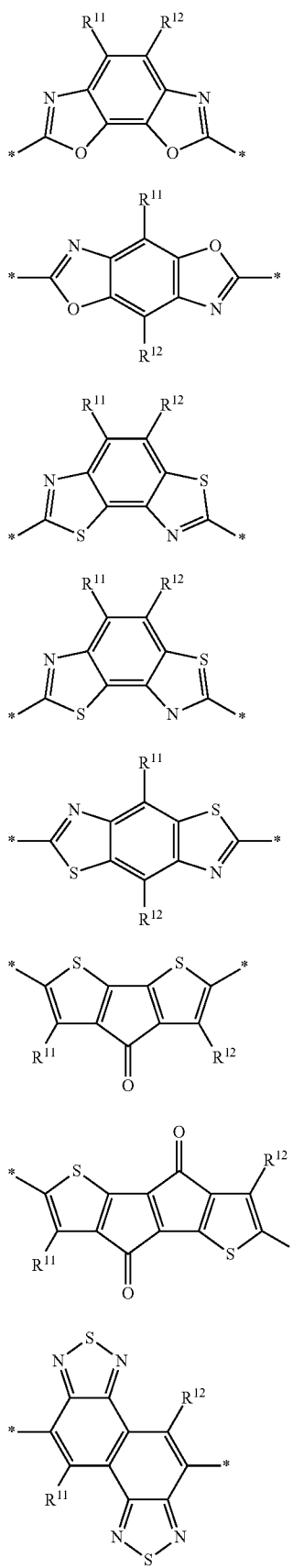
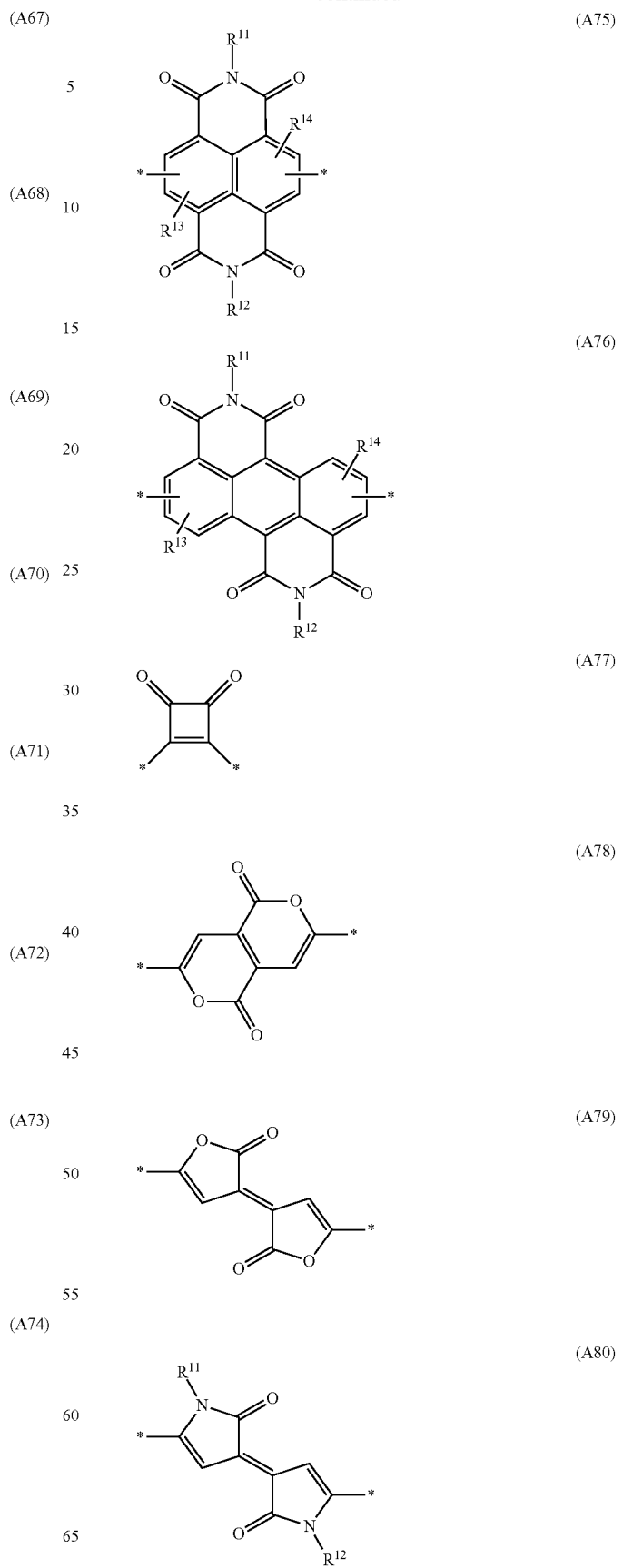

-continued (A81) 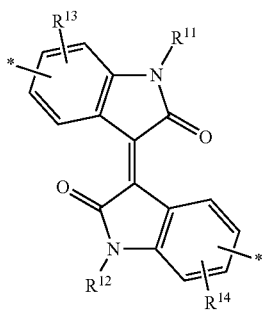

(A82) 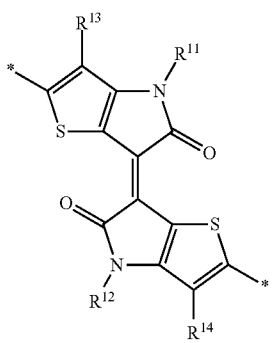

(A83) 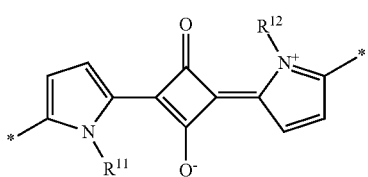

(A84) 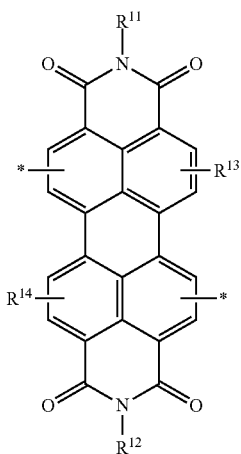

(A85) 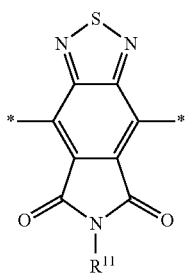

-continued (A86) 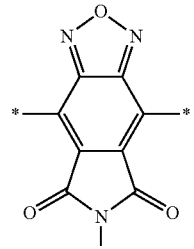

(A87) 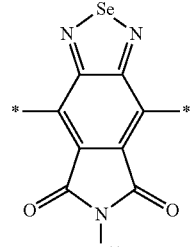

(A88) 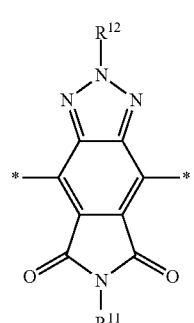

(A89) 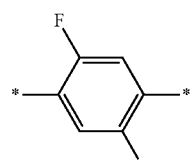

(A90) 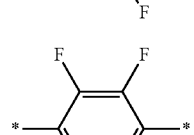

(A91) 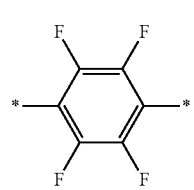

wherein $R^{11}$, $R^{12}$, $R^{13}$, $R^{14}$, $R^{15}$ and $R^{16}$ independently of each other denote H or on each occurrence identically or differently F, Br, Cl, -CN, -NC, -NCO, -NCS, -OCN, -SCN, -C(O)NR$^0$R$^{00}$, -C(O)X$^0$, -C(O)R$^0$, -NH$_2$, -NR$^0$R$^{00}$, -SH, -SR$^0$, -SO$_3$H, -SO$_2$R$^0$, -OH, -NO$_2$, -CF$_3$, -SF$_5$, optionally substituted silyl or hydrocarbyl with 1 to 40 C atoms that is optionally substituted and optionally comprises one or more hetero atoms, or P-Sp-, $R^o$ and $R^{oo}$ are independently of each other H or optionally substituted $C_{1-40}$ hydrocarbyl,
P is a polymerisable or crosslinkable group,
Sp is a spacer group or a single bond,
$X^o$ is halogen.

* * * * *